US008575094B2

(12) United States Patent
Wadman et al.

(10) Patent No.: US 8,575,094 B2
(45) Date of Patent: *Nov. 5, 2013

(54) USE OF TYPE-B LANTIBIOTIC-BASED COMPOUNDS HAVING ANTIMICROBIAL ACTIVITY

(75) Inventors: Sjoerd Nicolaas Wadman, Welwyn Garden City (GB); Michael John Dawson, Welwyn Garden City (GB); Jesus Cortes Bargallo, Welwyn Garden City (GB)

(73) Assignee: Novacta Biosystems Limited, Hertfordshire (GB)

( * ) Notice: Subject to any disclaimer, the term of this patent is extended or adjusted under 35 U.S.C. 154(b) by 567 days.

This patent is subject to a terminal disclaimer.

(21) Appl. No.: 12/357,077

(22) Filed: Jan. 21, 2009

(65) Prior Publication Data

US 2009/0203583 A1 Aug. 13, 2009

Related U.S. Application Data

(63) Continuation-in-part of application No. PCT/GB2008/002463, filed on Jul. 18, 2008.

(30) Foreign Application Priority Data

Jul. 18, 2007 (GB) .................................. 0714030.4

(51) Int. Cl.
*A61K 38/12* (2006.01)
*C07K 7/64* (2006.01)

(52) U.S. Cl.
USPC ............... 514/2.9; 514/2.3; 514/2.4; 530/317

(58) Field of Classification Search
None
See application file for complete search history.

(56) References Cited

U.S. PATENT DOCUMENTS

| | | | |
|---|---|---|---|
| 3,710,795 A | 1/1973 | Higuchi et al. | |
| 5,112,806 A | 5/1992 | Chatterjee et al. | |
| 5,304,540 A | 4/1994 | Blackburn et al. | |
| 5,667,991 A | 9/1997 | Koller et al. | |
| 5,683,675 A | 11/1997 | Vedia et al. | |
| 5,763,395 A | 6/1998 | Blackburn et al. | |
| 5,958,873 A | 9/1999 | Sakr et al. | |
| 5,985,823 A | 11/1999 | Goldstein | |
| 6,022,851 A | 2/2000 | Vertesy et al. | |
| 6,569,830 B1 | 5/2003 | Climo et al. | |
| 7,056,942 B2 * | 6/2006 | Hildesheim et al. | 514/411 |
| 7,122,514 B2 | 10/2006 | Climo et al. | |
| 2010/0048459 A1 | 2/2010 | Boakes et al. | |
| 2010/0168410 A1 | 7/2010 | Cade et al. | |
| 2010/0179207 A1 | 7/2010 | Wadman | |
| 2010/0261638 A1 | 10/2010 | Wadman | |

FOREIGN PATENT DOCUMENTS

| | | |
|---|---|---|
| DE | 197 45 583 | 4/1999 |
| EP | 0195359 | 9/1986 |
| EP | 0572942 | 12/1993 |
| EP | 0700998 | 3/1996 |
| EP | 1646646 | 3/2007 |
| WO | WO 91/07949 | 6/1991 |
| WO | WO 91/11172 | 8/1991 |
| WO | WO 94/02518 | 2/1994 |
| WO | WO 97/00694 | 1/1997 |
| WO | WO 98/55148 | 12/1998 |
| WO | WO 02/00196 | 1/2002 |
| WO | WO 02/088367 | 11/2002 |
| WO | WO 02/103010 | 12/2002 |
| WO | WO 03/099862 | 12/2003 |
| WO | WO 2004/033706 | 4/2004 |
| WO | WO 2005/093069 | 10/2005 |
| WO | WO 2006/080920 | 8/2006 |
| WO | WO 2007/036706 | 4/2007 |
| WO | WO 2007/083112 | 7/2007 |
| WO | WO 2008/151434 | 12/2008 |
| WO | WO 2009/010763 | 1/2009 |
| WO | WO 2009/010765 | 1/2009 |
| WO | WO 2010/058238 | 5/2010 |
| WO | WO 2010/082018 | 7/2010 |
| WO | WO 2010/082019 | 7/2010 |
| WO | WO 2010/089544 | 8/2010 |

OTHER PUBLICATIONS

Clostridium difficile-Induced Diarrhea from Merck Manual, http://merckmanual.com/professional/sec15/ch189e.html, pp. 1-2. Accessed Aug. 10, 2011.*
Clostridial Intra-abdominal Infections from Merck manual, http://merckmanual.com/professional/sec15/ch189/ch189f.html, p. 1. Accessed Aug. 10, 2011.*
Written Opinion of the International Preliminary Examining Authority in PCT/GB2010/000043, dated Feb. 1, 2011.
Wikipedia, the free encyclopedia, "Lanthionine", http://en.wikipedia.org/wiki/Lanthionine, Feb. 11, 2011.
European Search Report issued in European Patent Application No. EP 10 00 0424 (Apr. 1, 2010).
European Examination issued in European Patent Application No. 07 704 921.1 (Apr. 4, 2010).
International Search Report and Written Opinion in PCT/GB2010/000043 (Mar. 29, 2010).
Widdick et al., "Cloning and engineering of the cinnamycin biosynthetic gene cluster from *Streptomyces cinnamoneus cinnamoneus* DSM 40005", PNAS, 100(7):4316-4321 (Apr. 1, 2003).
Boakes et al., "Organization of the biosynthetic genes encoding deoxyactagardine B (DAB), a new lantibiotic produced by *Actinoplanes liguariae* NCIMB41362," The Journal of Antibiotics, 63:351-358 (2010).
Han, "Advances in Characterization of Pharmaceutical Hydrates," Trends in Bio/Pharmaceutical Industry, 25-29 (Mar. 2006).

(Continued)

*Primary Examiner* — Julie Ha
(74) *Attorney, Agent, or Firm* — Morgan, Lewis & Bockius LLP

(57) ABSTRACT

A method for the treatment or prophylaxis of a microbial infection of the lower intestine or colon in a subject is described, wherein the method comprises administration to the subject of a type-B lantibiotic, wherein the type-B lantibiotic may include compounds selected from the group consisting of mersacidin, actagardine, plantaricin, planosporicin, ruminococcin, antibiotic 10789, michiganin and haloduracin, and derivatives and variants thereof.

18 Claims, 6 Drawing Sheets

(56) References Cited

OTHER PUBLICATIONS

Vippagunta et al., "Crystalline solids," Adv. Drug Delivery Reviews, 48:3-26 (2001).
Examination Report in New Zealand Patent Application No. 569486 dated Mar. 10, 2011.
International Preliminary Report on Patentability in PCT/GB2010/000042 dated Apr. 19, 2011.
International Preliminary Report on Patentability in PCT/GB2010/000043 dated Apr. 14, 2011.
International Preliminary Report on Patentability in PCT/GB2010/000188 dated Apr. 19, 2011.
Non-final office action issued in U.S. Appl. No. 12/686,135 dated Apr. 28, 2011.
Office Action issued in European Patent Application No. 10000242.1 dated May 19, 2011.
Office Action issued in Chinese Application No. 200780006748.0 dated Mar. 23, 2011 (Translation included).
Notice of Allowance mailed in U.S. Appl. No. 12/161,221 dated May 12, 2011.
Altena et al. "Biosynthesis of the lantibiotic mersacidin: organization of a type B lantibiotic gene cluster" Applied and Environmental Microbiology 66(6): 2565-2571 (2000).
Arioli et al. "Gardimycin, a new anitbiotic from *Actinoplanes*: III. Biological properties" The Journal of Antibiotics 29(5):511-515 (1976).
Berge et al. "Pharmaceutical salts" Journal of Pharmaceutical Sciences 66(1):1-19 (1977).
Bierbaum et al. "Cloning, sequencing and production of the lantibiotic mersacidin" FEMS Microbiology Letters 127:121-126 (1995).
Bierman et al. "Plasmid cloning vectors for the conjugal transfer of DNA from *Escherichia coli* to *Streptomyces* spp." Gene 116(1): 43-49 (1992).
Britton et al. "Genome-Wide Analysis of the Stationary-Phase Sigma Factor (Sigma-H) Regulon of *Bacillus subtilis*" Journal of Bacteriology 184(17):4881-4890 (2002).
Castiglione et al. "A novel lantibiotic acting on bacterial cell wall synthesis produced by uncommon actinomycete *Planomonospora* sp." Biochemistry 46:5884-5895 (2007).
Chatterjee et al. "Biosynthesis and Mode of Action of Lantibiotics" Chem. Rev. 105:633-683 (2005).
Coronelli et al. "Gardimycin, A New Antibiotic From Actinoplanes: II. Isolation and preliminary characterization" Journal of Antibiotics 29(5):507-510 (1976).
Cotter et al. "Bacterial lantibiotics: strategies to improve therapeutic potential" Current Protein Peptide Science 6(1):61-75 (2005).
Dabard et al. "Ruminococcin A, a new lantibiotic produced by a *Ruminococcus gnavus* strain isolated from human feces" Appl. Environ. Microbiol. 67:4111-4118 (2001).
Dawson "Lantibiotics as antimicrobial agents" Expert Opinion on Therapeutic Patents, Informa Healthcare, GB, 17(4):365-369 (2007).
de Vos et al. "Maturation pathway of nisin and other lantibiotics: post-translationally modified antimicrobial peptides exported by gram-positive bacteria" Molecular Microbiology 17(3):427-37 (1995).
Dower et al. "High efficiency transformation of *E. coli* by high voltage electroporation" Nucleic Acids Research 16(13):6127-6145 (1988).
Fleisher et al. "Improved oral drug delivery: solubility limitations overcome by the use of prodrugs" Advanced Drug Delivery Reviews 19(2):115-130 (1996).
Flett et al. "High efficiency intergeneric conjugal transfer of plasmid DNA from *Escherichia coli* to methyl DNA-restricting Streptomycetes" FEMS Microbiology Letters 155(2): 223-229 (1997).
Fukase et al. "Synthetic study of peptide antibiotic nisin. V. Total synthesis of nisin" Bull. Chem. Soc. Jpn. 65:2227-2240 (1992).
Fumi et al. "Rifaximin treatment for symptoms of irritable bowel syndrome" The Annals of Pharmacotherapy 42:408-412 (2008).

Gardiner et al. "Fate of the Two-Component Lantibiotic Lacticin 3147 in the Gastrointestinal Tract" Applied and Environmental Microbiology 73(21):7103-7109 (2007).
Gravesen et al. "pbp2229-Mediated nisin resistance mechanism in Listeria monocytogenes confers cross-protection to class IIa bacteriocins and affects virulence gene expression" Applied and Environmental Microbiology 70(3): 1669-1679 (2004).
Guder et al. "Role of the single regulator MrsR1 and the two-component system MrsR2/K2 in the regulation of mersacidin production and immunity" Applied and Environmental Microbiology 68(1):106-113 (2002).
Guiotto et al. "PEGylation of the antimicrobial peptide nisin A: problems and perspectives" Il Farmaco 58(1):45-50 (2003).
Gust et al. "PCR-targeted *Streptomyces* gene replacement identifies a protein domain needed for biosynthesis of the sesquiterpene soil odor geosmin" PNAS 100(4): 1541-1546 (2003).
Gust et al. "λ Red-mediated genetic manipulation of antibiotic-producing *Streptomyces*" Advances in Applied Microbiology 54:107-128 (2004).
Heinzelmann et al. "A glutamate mutase is involved in the biosynthesis of the lipopeptide antibiotic friulimicin in *Actinoplanes friuliensis*" Antimicrobial Agents and Chemotherapy 47(2): 447-457 (2003).
Hilger et al. "Differential binding of IgG and IgA antibodies to antigenic determinants of bovine serum albumin" Clin. Exp. Immunol. 123:387-394 (2001).
Holtsmark, et al. "Purification, Characterization, and Gene Sequence of Michiganin A, an Actagardine-Like Lantibiotic Produced by the Tomato Pathogen *Clavibacter michiganensis* subsp. *michiganensis*" Applied and Environmental Microbiology 72(9):5814-5821 (2006).
Jack et al. "The genetics of lantibiotic biosynthesis" BioEssays 17(9): 793-802 (1995).
Kettenring et al. "Sequence determination of actagardine, a novel lantibiotic, by homonuclear 2D NMR spectroscopy" J. Antibiot. 43(9):1082-1088 (1990).
Lonetto et al. "The sigma 70 family: sequence conservation and evolutionary relationships" Journal of Bacteriology 174(12): 3843-3849 (1992).
Louie et al. "A phase 2 study of the toxin binding polymer tolevamer in patients with *C. difficile* associated diarrhoea" Proceedings of 14th European Congress of Clinical Microbiology and Infectious Diseases, Prague Congress Centre, Prague, Czech Republic, P548 (May 1-4, 2004).
Louie et al. "Tolemaver (GT160-246) binds Clostridium cytotoxins A/B and is associated with restoration of components of the anaerobic intestinal microflora during treatment of *C. difficileassociated* diarrhoea" Proceedings of 14th European Congress of Clinical Microbiology and Infectious Diseases, Prague Congress Centre, Prague, Czech Republic, P855 (May 1-4, 2004).
Malabarba et al. "Physico-chemical and biological properties of actagardine and some acid hydrolysis products" The Journal of Antibiotics 38(11):1506-1511 (1985).
Malabarba et al. "Synthesis and biological activity of some amide derivatives of the lantibiotic actagardine" The Journal of Antibiotics 43(9):1089-1097 (1990).
Marahiel et al. "Regulation of peptide antibiotic production in *Bacillus*" Molecular Microbiology 7(5):631-636 (1993).
McClerren et al. "Discovery and in vitro biosynthesis of haloduracin, a two-component lantibiotic" PNAS 103(46):17243-17248 (2006).
Miner et al. "Steroid-refractory ulcerative colitis treated with corticosteroids, metronidazole and vancomycin: a case report" BMC Gastroenterology 5:3 (2005).
O'Sullivan et al. "High- and low-copy-number *Lactococcus* shuttle cloning vectors with features for clone screening" Gene 137:227-231 (1993).
Parenti et al. "Gardimycin, a new antibiotic from Actinoplanes. I. Description of the producer strain and fermentation studies" The Journal of Antibiotics 29(5):501-506 (1976).
Rea et al. "Antimicrobial activity of lacticin 3147 against clinical *Clostridium difficile* strains" Journal of Medical Microbiology 56:940-946 (2007).

(56) References Cited

OTHER PUBLICATIONS

Rey et al. "Complete genome sequence of the industrial bacterium *Bacillus licheniformis* and comparisons with closely related *Bacillus* species" Genome Biology 5(10):R77 (2004).
Sahl et al. "Lantibiotics: Biosynthesis and biological activities of uniquely modified peptides from gram-positive bacteria" Ann. Rev. Microbiology 52:41-79 (1998).
Somma et al. "Gardimycin, a new antibiotic inhibiting peptidoglycan synthesis" Antimicrobial Agents and Chemotherapy 11(3):396-401 (1977).
Szekat et al. "Construction of an expression system for site-directed mutagenesis of the lantibiotic mersacidin" Applied and Environmental Microbiology 69(7):3777-3783 (2003).
"Treatment of *Clostridium difficile*—Associated Disease (CDAD)" Obstetrics and Gynecology 109(4):993-995 (2007).
Turner et al. "Solution structure of plantaricin C, a novel lantibiotic" Eur. J. Biochem. 264:833-839 (1999).
Turtell et al. "The use of nisin in cheesemaking. Chapter 5: International acceptance of nisin as a food preservative" Bulletin of the Int. Dairy Fed. 329:20-23 (1988).
Ugurlu et al. "Colonic delivery of compression coated nisin tablets using pectin/HPMC polymer mixture" Eur. J. Pharm. Biopharm. 67:202-210 (2007).
van Kraaij et al. "Lantibiotics: biosynthesis, mode of action and applications" Nat. Prod. Rep. 16:575-587 (1999).
Vértesy et al. "Ala(0)-actagardine, a new lantibiotic from cultures of *Actinoplanes liguriae* ATCC 31048" Journal of Antibiotics (Tokyo) 52(8):730-741 (1999).
Zimmermann et al. "The tetracyclic lantibiotic actagardine. 1H-NMR and 13C-NMR assignments and revised primary structure" Eur. J. Biochem. 228:786-797 (1995).
Zimmermann et al. "The three-dimensional solution structure of the lantibiotic murein-biosynthesis-inhibitor actagardine determined by NMR" Eur. J. Biochem. 246:809-819 (1997).
Appleyard et al. "NVB302 : Gastrointestinal Stability and in vivo Activity in the Hamster Cecitis Model for *Clostridium difficile* Infection," Poster F1-1520, 49th ICAAC, Sep. 12-15, 2009, San Francisco, USA.
Appleyard et al. "NVB302: A Narrow Spectrum Antibiotic under Development for the Treatment of *Clostridium difficile* Infection," Poster F1-1517, 49th ICAAC, Sep. 12-15, 2009, San Francisco, USA.
Berendsen, "A Glimpse of the Holy Grail?" Science, 1998, 282, pp. 642-643.
Boakes et al., "Organization of the genes encoding the biosynthesis of actagardine and engineering of a variant generation system," Molecular Microbiology, 2009, 72(5), pp. 1126-1136.
Bradley et al. "Limits of Cooperativity in a Structurally Modular Protein: Response of the Notch Ankyrin Domain to Analogous Alanine Substitutions in Each Repeat," J. Mol. Biol., 2002, 324, pp. 373-386.
Definition of moiety, from http://dictionary.reference.com/browse/moiety, pp. 1-3. Accessed Aug. 26, 2010.
Designing Custom Peptides, from SIGMA Genosys, pp. 1-2. Accessed Dec. 16, 2004.
European Examination for European Patent Application No. 07704921.1 dated Aug. 30, 2010.
International Search Report and Written Opinion for PCT/GB2010/000042 dated May 20, 2010.
International Search Report and Written Opinion for PCT/GB2010/000188 dated May 20, 2010.
New Zealand Examination Report on New Zealand Patent Application 569486 dated Apr. 27, 2010.
Ngo et al. "Computational Complexity, Protein Structure Prediction, and the Levinthal Paradox," The Protein Folding Problem and Tertiary Structure Prediction, K. Merc Jr. and S. Le Grand Edition, 1994, pp. 491-495.
Rudinger J, "Characteristics of the amino acids as components of a peptide hormone sequence," Peptide Hormones, JA Parsons Edition, University Park Press, Jun. 1976, pp. 1-7.
Schinzel R, Drueckes P, "The phosphate recognition site of *Escherichia coli* maltodextrin phosphorylase," FEBS, Jul. 1991, 286(1,2), pp. 125-128.
Translation of Israeli Examination Report on Israeli Patent Application No. 192446 dated Apr. 22, 2010.
Voet et al. "Abnormal Hemoglobins," Biochemistry, Second Edition, John Wiley & Sons, Inc., 1995, pp. 235-241.
Wadman et al. "NVB302: In vitro Activity Against *Clostridium difficile* and Intestinal Strains of Anaerobic Bacteria," Poster F1-1518, 49th ICAAC, Sep. 12-15, 2009, San Francisco, USA.
Office Action issued in a related European Patent Application No. 10700336.0, dated May 3, 2012.
Office Action issued in a related European Patent Application No. 10702536.3, dated May 11, 2012.

* cited by examiner (a)

(b)

(a)

(b)

USE OF TYPE-B LANTIBIOTIC-BASED COMPOUNDS HAVING ANTIMICROBIAL ACTIVITY

RELATED APPLICATIONS

This application is related to GB patent application 0714030.4 filed 18 Jul. 2007; the contents of which are incorporated herein by reference in their entirety.

This application is also related to PCT patent application PCT/GB2008/002463 filed 18 Jul. 2008; the contents of which are incorporated herein by reference in their entirety.

SEQUENCE LISTING SUBMISSION VIA EFS-WEB

A computer readable text file, entitled "056646-5044-SeqListing-04102009.txt," created on or about Apr. 10, 2009 with a file size of about 24 kb contains the sequence listing for this application and is hereby incorporated by reference in its entirety.

FIELD OF THE INVENTION

This invention relates to the use of type-B lantibiotics, and derivatives and variants thereof, in the treatment or prophylaxis of a microbial infection in a subject.

BACKGROUND

*Clostridium difficile* infection is the most important cause of hospital-acquired diarrhoea. *C. difficile* is a spore-forming, anaerobic bacterium that is normally present in the intestine of up to 3% of healthy adults and 66% of infants. This organism rarely causes problems in healthy individuals, as it is kept in check by the normal bacterial population of the intestine. However, the use of broad spectrum antibiotics either therapeutically or prophylactically disturbs the balance of bacteria in the gut, allowing resistant *C. difficile* present as spores to multiply rapidly and produce toxins which cause *Clostridium difficile*-associated diarrhoea (CDAD—also known as antibiotic-associated diarrhoea), infection of the colonic lumen, pseudomembranous colitis and in extreme cases, death.

There are currently two generally accepted therapies for the treatment of CDAD, namely vancomycin and metronidazole. Both agents are associated with a high (15-20%) rate of recurrence of symptoms, possibly because they do not allow the intestinal flora to return to normal, and agents with an improved profile are greatly needed. In addition, many clinicians are reluctant to prescribe vancomycin long term for fear of increasing general resistance to this antibiotic, which is also used as a "last resort" treatment for other multi-drug resistant pathogens.

Lantibiotics are peptides having antibiotic and other activities, produced by Gram-positive bacteria. They contain, among other modified residues, the thioether amino acids lanthionine and methyllanthionine, which cross-link the peptide chain into a polycyclic structure. They have been classified into two families, type-A and type-B. Type-A lantibiotics are generally elongate amphiphiles that are capable of forming pores in bacterial and other plasma membranes. Examples are nisin and subtilin. Type-B lantibiotics, by contrast, are globular, conformationally defined peptides. Examples are mersacidin and actagardine. Further examples are given in Table 1 below.

The lantibiotics are a class of bacterially produced antibiotic peptides with a narrow spectrum of activity that includes *Clostridium difficile*. Structurally, the lantibiotics are characterised by extensive post-translational modification primarily involving dehydration of the hydroxyl-containing residues serine and threonine, with optional cyclisations of cysteine onto these dehydrated residues to form thioether bridges.

TABLE 1

Classification of Lantibiotics

| Type-A Lantibiotics | Type-B Lantibiotics |
| --- | --- |
| Nisin A | Mersacidin |
| Nisin Z | Actagardine |
| Subtilin | Lacticin 3147 |
| Epidermin | Plantaricin C |
| Gallidermin | Ruminococcins A and B |
| Mutacin B | Haloduracin |
| Epicidin 280 | Cinnamycin |
| Epilancin K7 | Duramycin |
| Lactocin S | Ancovenin |
| Lacticin 481 | Planosporicin |
| Salivaricin A | Michiganin A |
| Variacin | Antibiotic 107891 |

Additionally, Lichenicidin may be classified as a type-B lantibiotic.

Classification according to HG Sahl et al, *Ann. Rev. Microbiology* 1998, 52, 41 (incorporated by reference herein in its entirety).

Various intermediate forms of lantibiotics also exist and include a number of substances whose biological actions depend on synergy with other peptides. Examples of the latter group include the cytolysins and staphylococcins.

Nisin is the best characterised type-A lantibiotic and has been approved as a food additive in several countries (Turtell and Delves-Broughton, International acceptance of nisin as a food preservative. *Bull. Int. Dairy Fed.* 1988, 329, 20-23). Nisin is selective for Gram-positive bacteria including *Clostridium* spp. This narrow spectrum of antibacterial activity would, in principle, make it very well suited as a therapeutic agent for the treatment of CDAD. Unfortunately, nisin is readily metabolised by intestinal enzymes, making its delivery to the site of infection problematic.

A number of attempts to formulate nisin such that it might be delivered to the colon intact have been described (U.S. Pat. No. 5,985,823,1999; T. Ugurlu et al. *Eur. J. Pharm. Biopharm.* 2007, 67, 202) but the intrinsic vulnerability of nisin to enzymatic cleavage remains a problem.

This has led to the suggestion that nisin and other lantibiotics would need to be encapsulated to target specific areas of the gut to be effective in oral administration (Rea et al. *J. Med. Microbiol.* 2002, 56, 940). Accordingly, it has been suggested that a bacteriocin should be administered as an enema via an anal route (ibid.).

The present inventors have previously identified and synthesised mersacidin compounds for use as antibiotics (WO 2007/036706). The inventors have also identified and synthesised actagardine compounds, also for use as antibiotics (PCT/GB2007/000138-WO/2007/083112).

The identification of the gene clusters responsible for cinnamycin and duramycin production have been reported, as well as improved methods for their production (see WO 02/088367 and WO 2004/033706 respectively).

Within the field of antibiotics, there is a continuing need for the provision of new antibiotic compounds, to overcome issues such as resistance, bio-compatibility, toxicity and the like. Accordingly, methods of producing lantibiotics, and the production of variant forms of lantibiotics (which may have a different activity profile compared to native forms), are desirable.

For the treatment of a *Clostridium difficile* infection, it is considered desirable for the antibacterial agent to posses one or more following, amongst others: good in vivo activity against *Clostridium difficile*; relatively poor activity against most other organisms normally found in the gut flora; little or no toxicity, systemically or in the bowel; and relatively little absorbance when given orally (thereby minimising the systemic effects).

However, until now, there has been a lack of in vivo experimental data to demonstrate the suitability of lantibiotic compounds having antibacterial activity in vitro for use in a method of treatment or prophylaxis of a bacterial infection in a subject. Particularly, there is little data concerning the activity of lantibiotic compounds, and their use in vivo to treat bacterial infections of the colon. The present inventors have now established the in vivo activity of a number of type-B lantibiotic compounds whose use in treatment or prophylaxis has not been previously suggested.

DISCLOSURE OF THE INVENTION

The present invention provides the use of a type-B lantibiotic, or a derivative or variant thereof, in the treatment or prophylaxis of a microbial infection in a subject. The infection may be an infection of the gastrointestinal tract, preferably the intestine, and most preferably of the colon. Particularly, in one aspect of the present invention, there is provided a method of treating a bacterial infection. Preferably, the infection is a *Clostridium* infection, preferably a *Clostridium perfringens, Clostridium difficile, Clostridium tetani* or *Clostridium botulinum* infection, most preferably *C. difficile* infection. These methods provide new and useful alternatives to the method of treatment utilising a type-A lantibiotic, vancomycin or metronidazole.

The invention also provides a method for treating of a disease caused by a bacterial infection of the intestine colon. The method may be used to treat pseudomembranous colitis or CDAD. Preferably, the infection is a *Clostridium* infection, preferably a *Clostridium perfringens, Clostridium difficile, Clostridium tetani* or *Clostridium botulinum* infection, most preferably *C. difficile* infection.

The present invention also provides a method of treatment or prophylaxis of a subject comprising the step of administering a type-B lantibiotic to the subject. Preferably the type-B lantibiotic is administered orally.

The type-B lantibiotics described herein, and derivatives and variants thereof, may be selective for *C. difficile*. These compounds may have reduced activity against other commensal gut flora, particularly *Bifidobacterium* spp and *Bacteroides* spp, compared to vancomycin or metronidazole.

The compounds described herein have similar activity against *C. difficile* as vancomycin and provide new and useful alternatives to vancomycin in a method of treatment or prophylaxis of a microbial infection in a subject.

The type-B lantibiotics described herein may have increased stability to enzymatic degradation compared to nisin. Particularly, the compounds may have improved stability to intestinal juices compared to nisin. The type B lantibiotic structures are more compact than type-A compounds and they do not have the extensive linear character of the A-forms. Consequently, they are less vulnerable to proteolysis and are therefore more likely to reach the site of an infection, such as a bacterial infection of the lower intestinal tract.

The compounds of the disclosure are advantageous because they have high antibacterial activity against one or more strains of *C. difficile*, for example when activity is measured by a standard test such as minimum inhibitory concentrations (MICs), generally the compounds employed in the disclosure have an MIC of 4 µg/ml or lower, such as 2 µg/ml.

Additionally, the compounds of the present disclosure may be particularly suited to administration to humans and animals because they have low antibacterial activity against the naturally occurring healthy intestinal flora found in the body. In the case of treatment of diarrhea induced by a microbial infection such as *C. difficile* it is expected that a reduced recurrence of symptoms will be observed after treatment with the present compounds in comparison to treatment with known antibiotics because of the ability of the natural flora to survive the treatment with the present compounds. In particular the compounds of the disclosure are expected to have very low activity against *Bacteroides fragilis, Bacteroides thetaiotaomicron, Bifidobacterium longum, Lactobacillus rhamnosus*, and moderately low activity against *Peptostreptococcus anaerobius* and *Bifidobacterium adolescentis*.

What is more, when delivered orally the compounds employed in the disclosure are not absorbed systemically, which allows a relatively high concentration of the active to be delivered to the target in the colon/intestines. Thus, because there is no systemic delivery of the compounds when administered orally, then this may minimise any potential exposure to side effects for patients.

*C. difficile* infection and/or overgrowth is a common problem for patients during hospitalisation. It presents a real burden to the health care system and may be life threatening to vulnerable patients such as elderly patients. Thus treatments specific for the same would be very useful.

It is thought that the present compounds, although comprising peptide components, are not degraded to any significant extent by stomach acid or enzymes. Thus the compounds employed in the disclosure are particularly suitable for oral delivery. This can be advantageous in that it allows the flexibility to formulate the compounds in a simple and effective formulation enabling delivery of an undegraded active locally to the target tissue.

The physical properties of the compounds of the disclosure such as solubility, stability and the like are adequate for the intended therapeutic use.

BRIEF DESCRIPTION OF THE DRAWINGS

FIG. 1 (*b*) shows the stability of compounds VI and VII in simulated gastric fluid (SGF).

FIG. 2 (*b*) shows the stability of compound VI in simulated intestinal fluid (SIF).

DETAILED DESCRIPTION OF THE INVENTION

Figure 1:
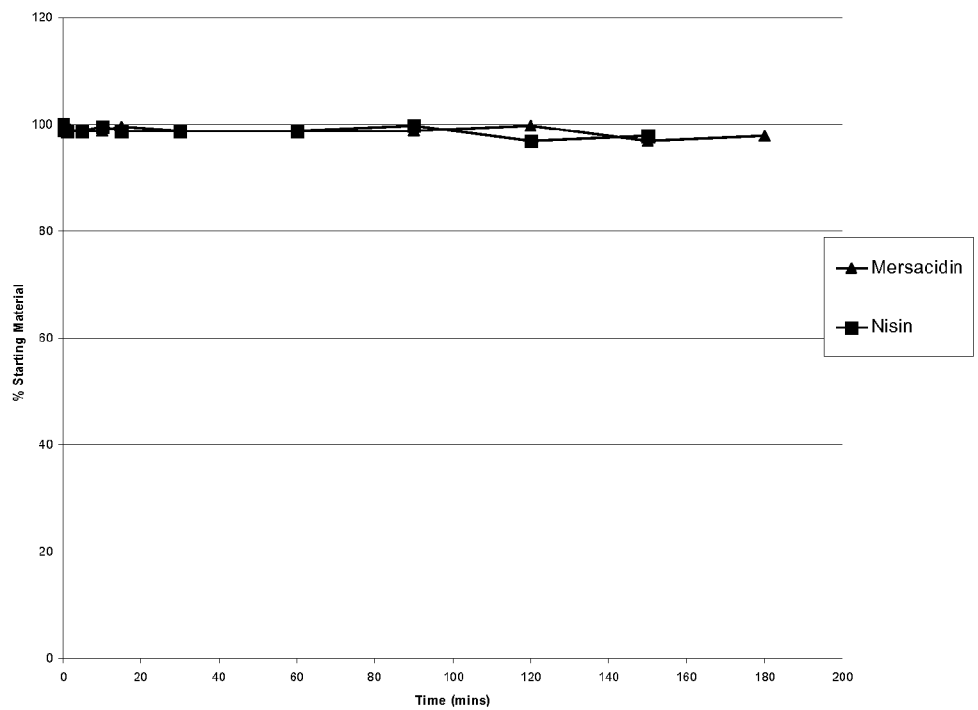
FIG. 1 (*a*) shows the stability of the lantibiotics mersacidin and nisin in simulated gastric fluid (SGF).
Figure 1:
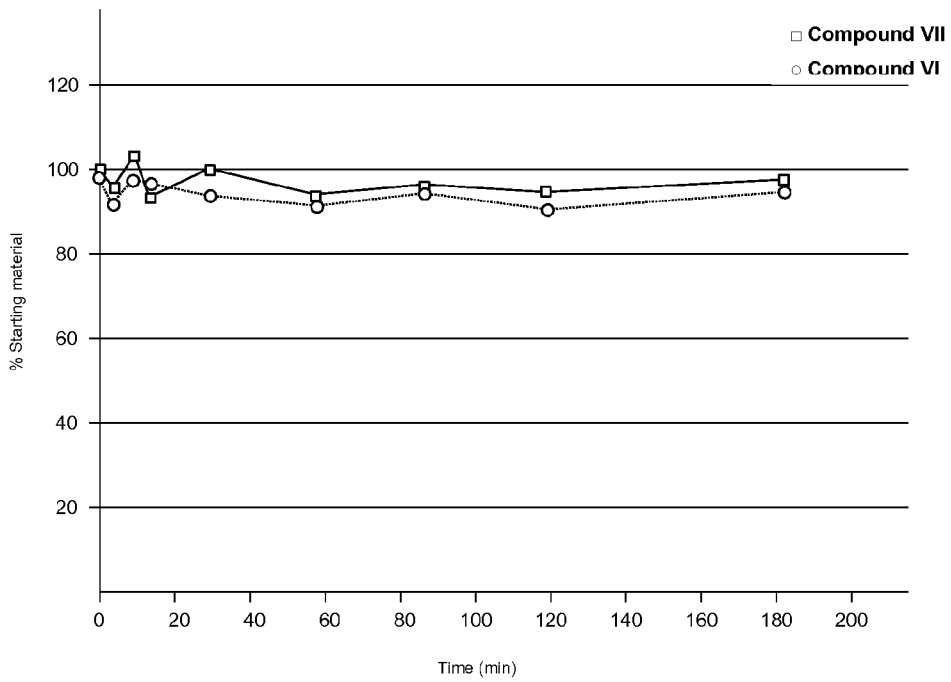

This invention relates to the use of type-B lantibiotics, and derivatives and variants thereof, in the treatment or prophylaxis of a microbial infection in a subject. Particularly, the invention provides the use of these compounds for the treatment of a clostridial infection, most preferably a *Clostridium difficile* infection. Where reference is made to the use of a type-B lantibiotic, such use also includes the use of a derivative or variant, unless the context specifies otherwise.

The development and recurrence of *C. difficile* infections is thought to be largely due to an imbalance in the normal intestinal flora. An ideal therapeutic agent for the treatment of CDAD (*C. difficile*-associated diarrhoea) would therefore be highly selective in killing *C. difficile*, but have low activity against the organisms that dominate the gut flora under normal healthy conditions, most notably *Bifidobacterium* spp and *Bacteroides* spp. Such an agent would allow the gut flora to return to its normal equilibrium state during therapy and thereby reduce the risk of recurrence of CDAD.

Both of the therapeutic agents in current use for CDAD, vancomycin and metronidazole, are routinely used at high doses and have significant activity against the organisms comprised in a healthy gut flora. It is widely believed that the frequent recurrence of CDAD in individuals that have suffered previous episodes of *C. difficile* infection occurs because the gut flora has failed to return to normal during the course of therapy.

The compounds described herein may be used with improved selectivity towards pathogenic microbes in the presence of gut flora. The compounds described herein may be used with similar effect as vancomycin and metronidazole against *Clostridium difficile*.

The type-B lantibiotics described herein, and derivatives and variants thereof, may also have improved stability to degradative enzymes compared to type A lantibiotics such as nisin, such as those found in the gastrointestinal tract. The local bioavailability of the active compound may therefore be increased at the site of infection, as the compound is not degraded by the degradative enzymes. Increasing the concentration of compound in the intestinal tract is especially important in the treatment of subjects with diarrhoea where the residency time of the compound may be low.

The preferred method of dosage for the treatment of *C. difficile* infections is via the oral route of administration. In the absence of significant absorption or metabolism in the gastrointestinal tract, this ensures that the maximum achievable concentration of drug substance is delivered to the site of infection, most notably the intestinal tract. Whilst the oral absorption of peptides and related substances of a molecular weight >1,000 Daltons is generally low, metabolism through peptidase enzymes is generally rapid and indeed forms an essential part of the normal digestion of food. The susceptibility of peptides towards enzymatic digestion in the stomach and intestine can reliably be estimated in vitro by measuring their stability in Simulated Gastric Fluid USP (SIF, pepsin in saline, pH 1.2) and Simulated Intestinal Fluid USP (SIF, pancreatin in aqueous potassium dihydrogen phosphate, pH 6.8).

Type-B lantibiotics are much more structurally compact than type-A lantibiotics and have an essentially globular tertiary structure stabilised by thioether and other chemical bridges. As such, type-B lantibiotics present less of a target for metabolic enzymes and have a better chance of reaching the lower intestinal tract without the need for protective formulations.

The type-B lantibiotics, notably mersacidin and actagardine, also have activity against Gram-positive organisms, including important resistant pathogens such as *C. difficile*, MRSA and VRE. The antibacterial activity of mersacidin and actagardine is thought to be mainly derived from their ability to bind Lipid II, an important biosynthetic intermediate in bacterial cell wall synthesis. Lipid II binding is a clinically important antibacterial mechanism, also exploited by other prominent antibiotics such as vancomycin. Also part of the type-B group of lantibiotics are peptides such as cinnamycin, duramycin and ancovenin. It has been noted that these compounds have a weaker antibacterial activity compared to actagardine and mersacidin, and it is thought that their main biological action may be as enzyme inhibitors.

The present invention provides a method of selectively inhibiting the growth of *C. difficile* in the presence of other commensal gut flora. A compound for use in the present invention preferably has a low potency against non-pathogenic components of the gut flora. The gut flora may contain *Bifidobacterium* spp and/or *Bacteroides* spp. The gut flora may contain one or more organisms selected from the group consisting of *Bifidobacterium adolescentis* NCTC 11814, *Bifidobacterium longum* NCTC 11818, *Bacteroides fragilis* NCTC 9343 and *Bacteroides thetaiotaomicron* NCTC 10582.

A compound for use in the invention may selectively inhibit the growth of *C. difficile* in the presence of gut flora compared to vancomycin. Preferably, a compound for use in the invention has an inhibitory activity against an organism of the gut flora that is less than the inhibitory activity of vancomycin against that organism. Where the inhibitory activity of a compound against an organism of the gut flora is measured in minimal inhibitory concentration (MIC), a compound for use in the invention may have a MIC that is 2 or more times, 4 or more times, 8 or more times, 16 or more times, or 32 or more times than the MIC of vancomycin against that organism.

Preferably a compound for use in the invention has lower activity against two, three, four, five or more non-pathogenic organisms of the gut flora compared to the activity of vancomycin.

Suitably a compound for use in the invention has an activity against *C. difficile* that is comparable or better to that of vancomycin. Where the inhibitory activity of a compound against *C. difficile* is measured in minimal inhibitory concentration (MIC), a compound for use in the invention may have a MIC that is 16 times or less, 8 times or less, 4 times or less, 2 times or less than the MIC of vancomycin against *C. difficile*. The compounds may have an activity that is equal to or more than that of vancomycin.

The present invention also relates to the treatment of an infection that has not been eradicated by treatment with another active compound, preferably a compound that is not described for use herein. The other active compound may be vancomycin or metronidazole.

The present invention also provides a method of treatment of a microbial infection which comprises administering to a subject in need of treatment an effective amount of a type-B lantibiotic, in combination with a second active agent. The second active agent may be another type-B lantibiotic. Alternatively, the second active agent may be another antimicrobial agent or another agent intended to treat a second symptom or cause of a condition to be treated.

The second active agent may be a compound or a composition that is associated with the restoration of components of the anaerobic intestinal microflora, particularly during treatment of *C. difficile*-associated diarrhea. The second active agent may be tolevamar (GT160-246).

In a further aspect, the method provides a type-B lantibiotic and a second active agent, as a combined preparation for simultaneous, separate or sequential use in therapy.

In an additional aspect, the method provides a type-B lantibiotic and a second agent, as a combined preparation for simultaneous, separate or sequential use in therapy for the treatment or prophylaxis of a microbial infection in a subject.

A compound described herein may be used in a pharmaceutical composition. Thus, the type-B lantibiotic may be administered in a composition also comprising a pharmaceutically acceptable carrier. The composition may be a delayed or sustained release composition.

The invention also provides a method of limiting the growth of *C. difficile* spores comprising the step of contacting a suspension of *C. difficile* spores with a type-B Lantibiotic. The spores may be in a suspension. The method may be an in vitro method.

The invention also provides a method of limiting the germination of *C. difficile* spores comprising the step of contacting a suspension of *C. difficile* spores with a type-B Lantibiotic. The spores may be in a suspension. The method may be an in vitro method. The invention provides a method of inhibiting bacterial growth, preferably *C. difficile* growth, in a protease-containing medium, particularly a pancreatin-containing medium, the method comprising the step of contacting a bacterium, in the medium, with a compound or composition as described herein. Preferably the medium is a intestinal fluid medium. Preferably the method is an in vitro method. In this case, the medium may be a simulated intestinal medium. Intestinal extracts may also be used.

*C. difficile* may be a strain that is a clinical isolate.

Type-B Lantibiotics

The present invention provides the use of a type-B lantibiotic, or a derivative or a variant thereof, in the treatment or prophylaxis of a microbial infection in a subject.

A type-B lantibiotic compound suitable for use in the methods of the present invention binds Lipid II.

Naturally occurring type-B lantibiotics for use in the invention include the members of the mersacidin and actagardine families. Preferred compounds for use in the methods of the invention are described below.

Derivatives and variants of the type-B lantibiotics, as well as modified forms of these compounds, may also find use in the methods described herein. These compounds can be produced synthetically, semi-synthetically (e.g. by chemical modification of fermented products) or by genetic changes to the organisms which produce them. Potentially, a type-B lantibitotic could be varied by all three routes, with the latter two being of particular interest. For example, modification of amino acids could be used to produce variants which have altered activity profiles, as well as properties such as bioavailability, biodistribution or the ability to overcome resistance mechanisms to the parent type-B lantibiotic itself. Altered amino acids may also be useful to introduce reactive side-chains allowing modification of the peptide by chemical means.

In one embodiment, the type-B lantibitotic is actagardine or mersacidin, or variants and derivatives thereof.

In one embodiment, the type-B lantibitotic is actagardine, or variants and derivatives thereof.

In one embodiment, the type-B lantibitotic is mersacidin, or variants and derivatives thereof.

Actagardine

For use in the present invention there is provided an actagardine compound of formula (I):

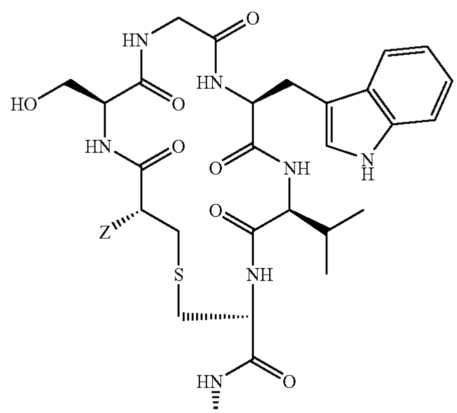

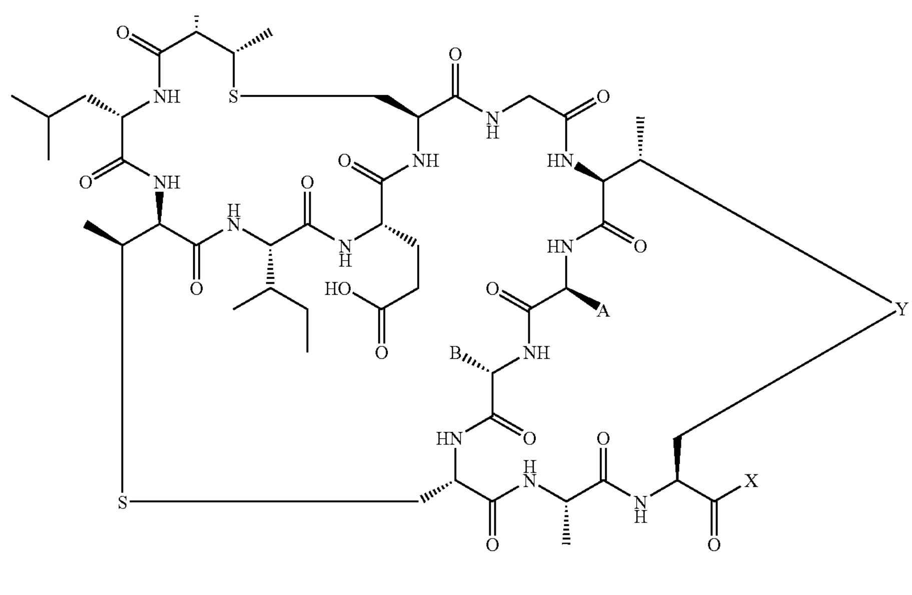

wherein A is a Leu; Val; or Ile amino acid side chain; B is a Leu; Val; or Ile amino acid side chain; X is —NR$^1$R$^2$ or —OH; and Y, Z, R$^1$ and R$^2$ are as defined below, or a pharmaceutically acceptable salt thereof.

Alternatively, the structure of the compound of formula (I) may be represented conveniently thus:

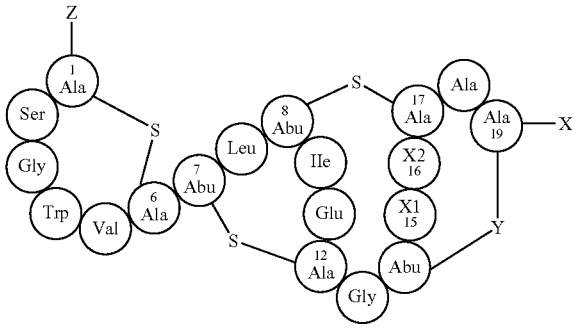

wherein:

X1 denotes that the residue is Leu; Val; or Ile;

X2 denotes that the residue is Leu; Val; or Ile;

X is —OH or —NR$^1$R$^2$, wherein R$^1$ represents hydrogen, or an alkyl or heteroalkyl group, substituted by at least one hydroxyl substituent, and R$^2$ represents hydrogen, or an alkyl or heteroalkyl group, substituted by at least one hydroxyl substituent, or R$^1$ and R$^2$ taken together with the nitrogen atom represent a heterocyclic group having at least one hydroxyl substituent, wherein the heterocyclic group optionally further contains one or more heteroatoms, or R$^1$ and R$^2$ independently represent:

(1) hydrogen;

(2) a group of formula —(CH$_2$)$_n$—NR$^{11}$R$^{12}$, in which n represents an integer from 2 to 8 and R$^{11}$ and R$^{12}$ independently represent hydrogen or (C$_1$-C$_4$) alkyl or R$^3$ and R$^4$ taken together represent a group —(CH$_2$)$_3$—, —(CH$_2$)$_4$—, —(CH$_2$)$_2$—O—(CH$_2$)$_2$—, —(CH$_2$)$_2$—S—(CH$_2$)$_2$— or —(CH$_2$)$_5$—;

or R$^1$ and R$^2$ taken together with the adjacent nitrogen atom represent a piperazine moiety which may be substituted in position 4 with a substituent selected from:

(a) (C$_1$-C$_4$)alkyl;

(b) (C$_5$-C$_7$)-cycloalkyl, (c) pyridyl, (d) —(CH$_2$)$_p$—NR$^{13}$R$^{14}$ in which p represents an integer from 1 to 8 and R$^{13}$ and R$^{14}$ independently represent hydrogen or (C$_1$-C$_4$) alkyl;

(e) piperidinyl;

(f) substituted piperidinyl, wherein the substituted piperidinyl bears a N-substituent which is (C$_{1-4}$)alkyl;

(g) benzyl; and (h) substituted benzyl, wherein the phenyl moiety bears 1 or 2 substituents selected from chloro, bromo, nitro, (C$_1$-C$_4$)alkyl and (C$_1$-C$_4$)alkoxy;

Z is an amino acid residue, —NR$^3$R$^4$, —NR$^5$COR$^6$, —NR$^5$C(O)OR$^6$; —NR$^5$SOR$^6$, —NR$^5$SO$_2$R$^6$; —NR$^5$C(S)NR$^6$R$^7$, —NR$^5$C(NR$^1$)NR$^6$R$^7$, or —N=R$^9$, where R$^3$, R$^4$, R$^5$, R$^6$, R$^7$, R$^8$ and R$^9$ are independently hydrogen, or a group, optionally substituted, selected from alkyl, heteroalkyl, aryl, heteroaryl, aralkyl and heteroaralkyl, with the proviso that R$^9$ is not hydrogen;

Y is —S— or —S(O)—;

or a pharmaceutically acceptable salt thereof. Variants and biologically active derivatives of these compounds may also be used in the methods of the present invention.

It will be understood by reference to Z being a group —NH$_2$, that this moiety represents the N-terminus of the alanine residue at position 1 of the above compound. By reference to the group Z being an amino acid residue, it will be understood that this moiety represents an amino acid, conventionally referred to in the art as Xaa(0), linked to the amino acid at position 1 via an amide bond. By reference to the group Z being —NR$^3$R$^4$, —NR$^5$COR$^6$, —NR$^5$C(O)OR$^6$; —NR$^5$SOR$^6$, —NR$^5$SO$_2$R$^6$; —NR$^5$C(S)NR$^6$R$^7$, —NR$^5$C(NR$^8$)NR$^6$R$^7$, or —N=R$^9$, it will be understood that these groups represent modifications of the N-terminus of the amino acid at position 1.

In the representation of compound (I) above it will be appreciated that the amino acid residues are denoted by the appropriate three letter code. Abu refers to a 4-aminobutyric acid-derived amino acid residue, as will be clear from the structural formula.

By reference to the group X being —NR$^1$R$^2$, it will be understood that this moiety represents a substituent linked to the alanine at position 19 via an amide bond. By reference to the group X being —OH, it will be understood that this represents the alanine at position 19 having a free carboxyl terminus (—COOH).

It will also be appreciated that a reference to Z being an amino acid residue is a reference to a group —NR$^5$COR$^6$ where R$^6$ represents the amino- and side chain-functionality of an amino acid residue. For example, for the amino acid residue glycine, R$^6$ is —CH$_2$NH$_2$. Typically, for an amino acid residue, R$^6$ is a C$_{1-7}$ alkyl group having an amino substituent and optionally further substituted as appropriate.

For a compound of formula (I), where X1 and X2 are Val and Ile respectively, and Y is —S(O)—, the compound may be referred to as an actagardine derivative. Where X1 and X2 are Leu and Val respectively, and Y is —S—, the compound may be referred to as a deoxy-actagardine B derivative. Where X1 and X2 are Leu and Val respectively, and Y is —S—, Z is —NH$_2$, X is —OH, the compound is deoxyactagardine. Where X1 and X2 are Leu and Val respectively, and Y is —S—, Z is —NH$_2$, X is —NHCH$_2$CH$_2$OH, the compound may be referred to as deoxy-actagardine B N-[2-ethanolamine]monocarboxamide.

Compounds

Suitable actagardine compounds of formula (I) for use in the invention are described below.

Examples of X1 and X2

Suitably, X1 is Leu, and X2 is Val or Ile; or X1 is Val, and X2 is Val or Ile. In particular, X1 is Leu, and X2 is Val; or X1 is Val, and X2 is Ile.

Examples of R

R$^1$, R$^2$, R$^3$, R$^4$, R$^5$, R$^6$, R$^7$, R$^8$, R$^9$, R$^{10}$, R$^{11}$, R$^{12}$, R$^{13}$ and R$^{14}$ may be optionally substituted or optionally further substituted as appropriate. However, in some embodiments these groups are unsubstituted or not further substituted as appropriate.

Examples of X

R$^1$ and R$^2$ may both be hydrogen, i.e. X may be —NH$_2$.

Where R$^1$ or R$^2$ is an alkyl group, the alkyl group may be a C$_{1-7}$ alkyl group, most preferably a C$_{1-4}$ alkyl group. The R$^1$ or R$^2$ alkyl group is preferably fully saturated.

R$^1$ or R$^2$ may have one, two, three, four, five, six or seven carbon atoms. Where R$^1$ and R$^2$ taken together with the nitrogen atom of the amide represent a heterocyclic group where the group further contains one or more heteroatoms, preferably the heteroatoms are not at neighbouring positions in the heterocyclic ring.

Both of $R^1$ and $R^2$ may have one or more hydroxyl substituents. Between them, $R^1$ and $R^2$ may have two or more hydroxyl substituents. Suitably, $R^1$ has one, two or three hydroxyl substituents.

$R^1$ and $R^2$ may be the same.

In one embodiment $R^1$ is an alkyl group. In one embodiment $R^2$ is hydrogen.

Where $R^1$ or $R^2$ is a heteroalkyl group having a hydroxyl substituent, the hydroxyl substituent is a substituent on a carbon atom of the heteroalkyl group.

Where $R^1$ or $R^2$ is an alkyl or heteroalkyl group having two or more hydroxyl substituents, each hydroxyl substituent is a substituent on a different carbon atom of the alkyl or heteroalkyl group.

In one embodiment, the $R^1$ or $R^2$ alkyl group is acyclic. In one embodiment, the $R^1$ or $R^2$ alkyl group is linear.

In one embodiment, $R^1$ or $R^2$ is substituted or further substituted as appropriate. The substituent may be one or more groups selected from the group consisting of: carboxy, ester, acyloxy, amido, acylamido, and aryl and heteroaryl. Suitably, the substituent is one or more groups selected from the group consisting of: carboxy, ester, acyloxy, aryl and heteroaryl.

Suitably $R^1$ or $R^2$ is independently one of the substituents given below, where * indicates the point of attachment to the nitrogen atom:

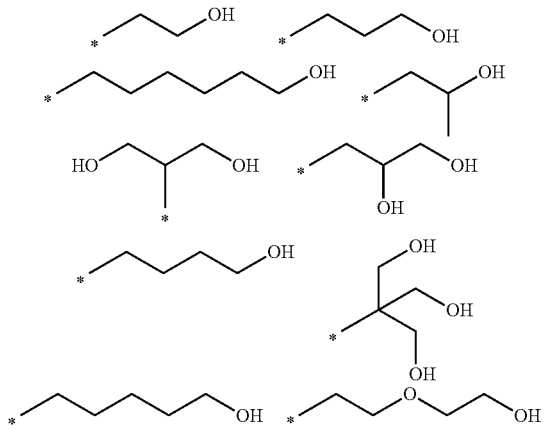

Additionally, or alternatively, $R^1$ or $R^2$ may be independently selected from one of the substituents given below, where * indicates the point of attachment to the nitrogen atom:

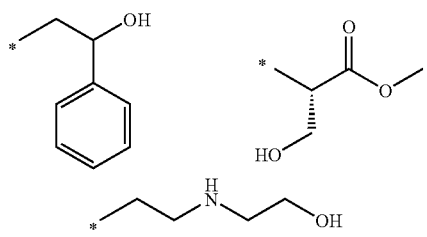

In one embodiment, $R^1$ is independently selected from the substituents given in either of the sets of substituents above. In this embodiment, $R^2$ is suitably hydrogen.

Alternatively, $R^1$ and $R^2$ together with the nitrogen atom, i.e. X, may be a substituent selected from the group below, where * indicates the point of attachment to the C-terminus carbonyl carbon:

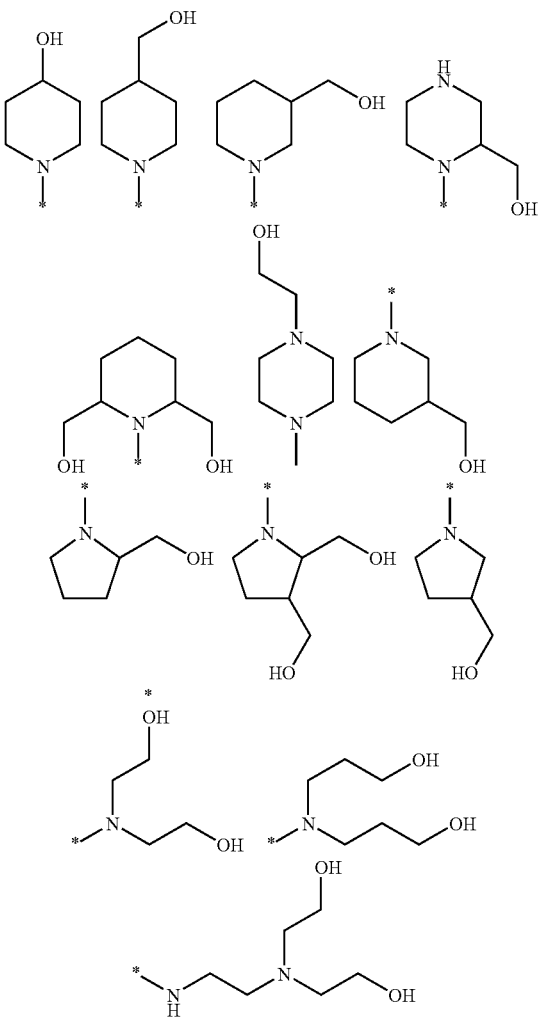

Additionally, or alternatively, $R^1$ or $R^2$ may be independently selected from the substituent given below, where * indicates the point of attachment to the nitrogen atom:

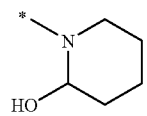

Suitably $R^1$ is —$CH_2CH_2OH$.

The (e) piperidinyl and (f) substituted piperidinyl groups suitably have their nitrogen atom at the 4-position.

The N-substituent may be selected from:

(d) —$(CH_2)_p$—$NR^{13}R^{14}$ in which p represents an integer from 1 to 8 and $R^{13}$ and $R^{14}$ independently represent hydrogen or ($C_1$-$C_4$) alkyl; and (f) substituted piperidinyl, wherein the substituted piperidinyl bears a N-substituent which is $(C_1\text{-}C_4)$alkyl.

If the N substituent is $-(CH_2)_p-NR^{13}R^{14}$, then $R^{13}$ and $R^{14}$ may for example be $(C_1\text{-}C_4)$alkyl, such as $(C_1\text{-}C_2)$ alkyl, e.g. methyl. Integer p is suitably 1 to 4, e.g. 3.

If the N substituent is substituted piperidinyl, then the N-substituent is suitably $(C_1\text{-}C_2)$ alkyl, e.g. methyl. As mentioned above, the N is generally in the 4-position.

Specific compounds for use in the invention are those wherein $R^1$ represents an alkyl or heteroalkyl group, substituted by at least one hydroxyl substituent, and $R^2$ represents hydrogen, or an alkyl or heteroalkyl group, substituted by at least one hydroxyl substituent, or $R^1$ and $R^2$ taken together with the nitrogen atom represent a heterocyclic group having at least one hydroxyl substituent, wherein the heterocyclic group optionally further contains one or more heteroatoms.

Examples of Z

In one embodiment, Z is $-NH_2$, an amino acid or $-NR^5COR^6$. Preferably, Z is $-NH_2$, or an amino acid.

In one embodiment, Z is $-NR^5COR^6$ and $R^5$ is hydrogen.

Z may be $-NH_2$.

Where Z is an amino acid residue, the amino acid residue is, for example a naturally occurring amino acid residue encoded by the genetic code or its D-isoform, more preferably an amino acid residue selected from the group Ile-, Lys-, Phe-, Val-, Glu-, Asp-, His-, Leu, Arg-, Ser- and Trp-. In one aspect, the amino acid residue may be selected from the group Ile-, Lys-, Phe-, Val-, Glu-, Asp-, His-, Leu-, Arg- and Ser-. Such variants may be produced by chemical addition of the residue to compounds where Z is $-NH_2$, as described in U.S. Pat. No. 6,022,851, which is incorporated herein by reference. It will be appreciated that the chemical addition of an amino acid allows the amino acid to be in the L- or D-configuration.

The amino acid residue may a modified natural amino acid residue, such as those residues formed during the post-translational modification of, for example, serine, cysteine and threonine residues. A residue within the compound of the invention may be selected from the dehydrated amino acids shown in the group below:

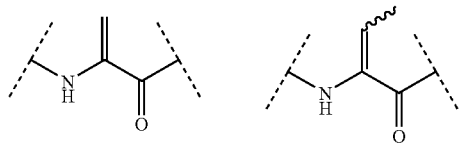

The second of these structures may be referred to as a dihydroamino butyric acid residue. Additionally, an amino acid residue may be selected from the cyclic residues shown in the group below:

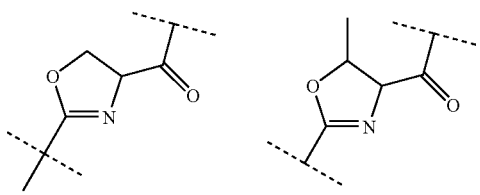

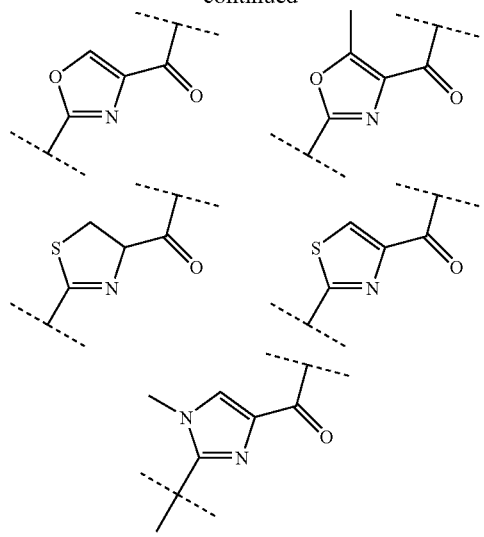

As will be appreciated, the synthesis of these cyclic structures typically involves the cyclisation of a serine, threonine or cysteine residue side chain with an amidic carbonyl of, typically, but not essentially, a neighbouring amino acid residue.

Thus, the structures shown above include a portion of a neighbouring group, such as a neighbouring amino acid. Alternatively, the neighbouring group may be derived from a group that together with a serine, threonine or cysteine residue forms an amide bond at the residue N-terminus. This is shown retrosynthetically in the example below for an oxazoline amino acid residue derived from a serine residue that is linked with a neighbouring group through an amide bond at the N-terminus of the serine residue:

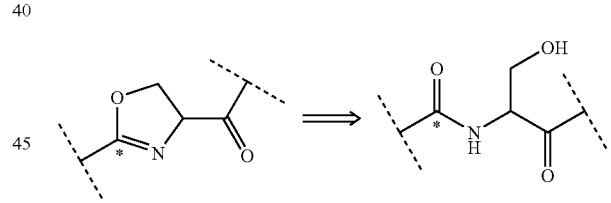

The asterisk (*) indicates the location of the carbon atom in the oxazoline as derived from the carbonyl carbon in the neighbouring group. The retrosynthesis is presented for illustrative purposes only, and the post translationally modified amino acid residues discussed above may be prepared from alternative precursors.

The amino acid residue may be a non-natural or unusual natural amino acid. The amino acid may be selected from the group consisting of seleno serine, aminobutyric acid, aminoisobutyric acid, butlyglycine, citrulline, cyclohexylalanine, diaminopropionic acid, homoserine, hydroxy proline, norleucine, norvaline, ornithine, penicillaminepyroglutamic acid, sarcosine, statine, tetrahydroisoquinoline-3-carboxylic acid, and thienylalanine. The L- or D-forms may be selected.

The amino acid may be an α-, β-, or γ-amino acid. The amino group of the amino acid may be mono- or di-alkylated. Where Z is an amino acid, the amino group of the amino acid may be modified. Thus, the N terminus may be a group selected from —$NR^3R^4$, —$NR^5COR^6$, —$NR^5C(O)OR^6$; —$NR^5SOR^6$, —$NR^5SO_2R^6$; —$NR^5C(S)NR^6R^7$ and —$NR^5C(NR^8)NR^6R^7$ where $R^3$, $R^4$, $R^5$, $R^6$, $R^7$ and $R^8$ are defined as above.

Where Z is an amino acid residue, the amino acid residue may also be a protected amino acid residue. The amino group such protecting groups may be selected from the group consisting of Fmoc, Boc, Ac, Bn and Z (or Cbz). The side-chain may also be protected as appropriate. The side chains protecting groups may be selected from the group consisting of Pmc, Pbf, OtBu, Trt, Acm, Mmt, tBu, Boc, ivDde, 2-ClTrt, tButhio, Npys, Mts, $NO_2$, Tos, OBzl, OcHx, Acm, pMeBzl, pMeOBz, OcHx, Bom, Dnp, 2-Cl—Z, Bzl, For, and 2-Br—Z as appropriate for the side chain.

Natural and non natural amino acids, and their protected versions, as well as protecting group deprotection strategies are well known. Many are summarised in the Merck NOVABIOCHEM™ catalogue 'Reagents/or Peptide and HighThroughput Synthesis' (2006/7) (incorporated herein by reference in its entirety).

One of $R^3$ and $R^4$ may be a group, optionally substituted, selected from alkyl, heteroalkyl, aryl, heteroaryl, aralkyl and heteroaralkyl.

$R^3$ and $R^4$ may both be hydrogen.

Where Z is —$NH_2$, i.e. $R^3$ and $R^4$ are both hydrogen, this group may be in a protected form. The protecting group may be selected from the group consisting of Fmoc, Boc, Ac, Bn and Z (or Cbz). Alternative protecting groups may be used, such as those described below in relation to protected forms.

In one embodiment $R^5$ is hydrogen.

Suitably, Z is —$NH_2$, an amino acid or —$NR^5COR^6$. Where Z is —$NR^5COR^6$, $R^5$, for example, is hydrogen and $R^6$ is an aralkyl group substituted with a hydroxyl group, such as the aralkyl group is substituted on the alkyl portion of the group. $R^6$ may be —CH(OH)Ph (i.e. Z is modified with a mandelyl group).

Examples of Structures

Suitably the type-B lantibiotic is an actagardine compound selected from the group below:
Compound II: Actagardine
Compound III: Deoxyactagardine B
Compound V: Phe(0)deoxy-actagardine B
Compound VI: Actagardine N-[2-ethanolamine]monocarboxamide
Compound VII: Deoxy-actagardine B N-[2-ethanolamine] monocarboxamide
Compound VIII: Deoxy-Actagardine B N-[4-butanolamine] monocarboxamide
Compound IX: Deoxy-actagardine B (3-amino-1,2-propanediol) monocarboxamide
Compound X: Deoxy-actagardine B (2-amino-1,3-propanol) monocarboxamide
Compound XI: Deoxy-actagardine B [tris(hydroxymethyl)methylamine]monocarboxamide
Compound XII: Deoxy-actagardine B (1-amino-2-propanol) monocarboxamide
Compound XIII: Deoxy-actagardine B (1-amino-3-propanol) monocarboxamide
Compound XIV: (L)-Phenylalanyl-(0)-deoxyactagardine B (ethanolamine) monocarboxamide
Compound XV: (L)-Tryptophanyl-(0)-deoxyactagardine B (ethanolamine) monocarboxamide
Compound XVI: (L)-Alanyl-(0)-deoxyactagardine B (ethanolamine) monocarboxamide
Compound XVII: (D)-Alanyl-(0)-deoxyactagardine B (ethanolamine) monocarboxamide
Compound XVIII: (L)-Isoleucinyl-(0)-deoxyactagardine B (ethanolamine) monocarboxamide
Compound XIX: (L)-Leucinyl-(0)-deoxyactagardine B (ethanolamine) monocarboxamide
Compound XX: N-Phenylacetyl deoxyactagardine B (ethanolamine) monocarboxamide
Compound XXI: N-Acetyl deoxyactagardine B (ethanolamine) monocarboxamide
Compound XXII: N-Mandelyl deoxyactagardine B (ethanolamine) monocarboxamide
Compound XXIII: Deoxyactagardine B (N,N-bis(2-hydroxyethyl)ethylene diamine) monocarboxamide Additionally, or alternatively the preferred compounds according to the first aspect of the invention present invention may be selected from the compounds listed below:
Compound L: Deoxy-Actagardine B N-[2-hydroxy-2-phenylethylamine]monocarboxamide
Compound LI: Deoxy-actagardine B (L-serine methyl ester) monocarboxamide
Compound LII: Deoxyactagardine B (N-(2-hydroxyethyl) ethylenediamine) monocarboxamide
Compound LIII: Deoxy-actagardine B (2-hydroxypiperazine) monocarboxamide Additionally, or alternatively the preferred compounds according to the first aspect of the invention present invention may be selected from the compounds listed below:
Compound LX: (L)-Alanyl-(0)-deoxyactagardine B (ethanolamine) monocarboxamide
Compound LXI: (D)-Alanyl-(0)-deoxyactagardine B (ethanolamine) monocarboxamide
Compound LXII: (L)-Isoleucinyl-(0)-deoxyactagardine B (ethanolamine) monocarboxamide
Compound LXIII: (L)-Leucinyl-(0)-deoxyactagardine B (ethanolamine) monocarboxamide
Compound LXIV: N-Phenylacetyl deoxyactagardine B (ethanolamine) monocarboxamide
Compound LXV: N-Acetyl deoxyactagardine B (ethanolamine) monocarboxamide
Compound LXVI: N-Mandelyl deoxyactagardine B (ethanolamine) monocarboxamide The most preferred compounds are:
Compound I: Deoxy-Actagardine B N-[2-ethanolamine] monocarboxamide
Compound III: Actagardine N-[2-ethanolamine]monocarboxamide Additional Actagardine Compounds For use in the present invention there is also provided an actagardine compound of formula (Ia):

(Ia)

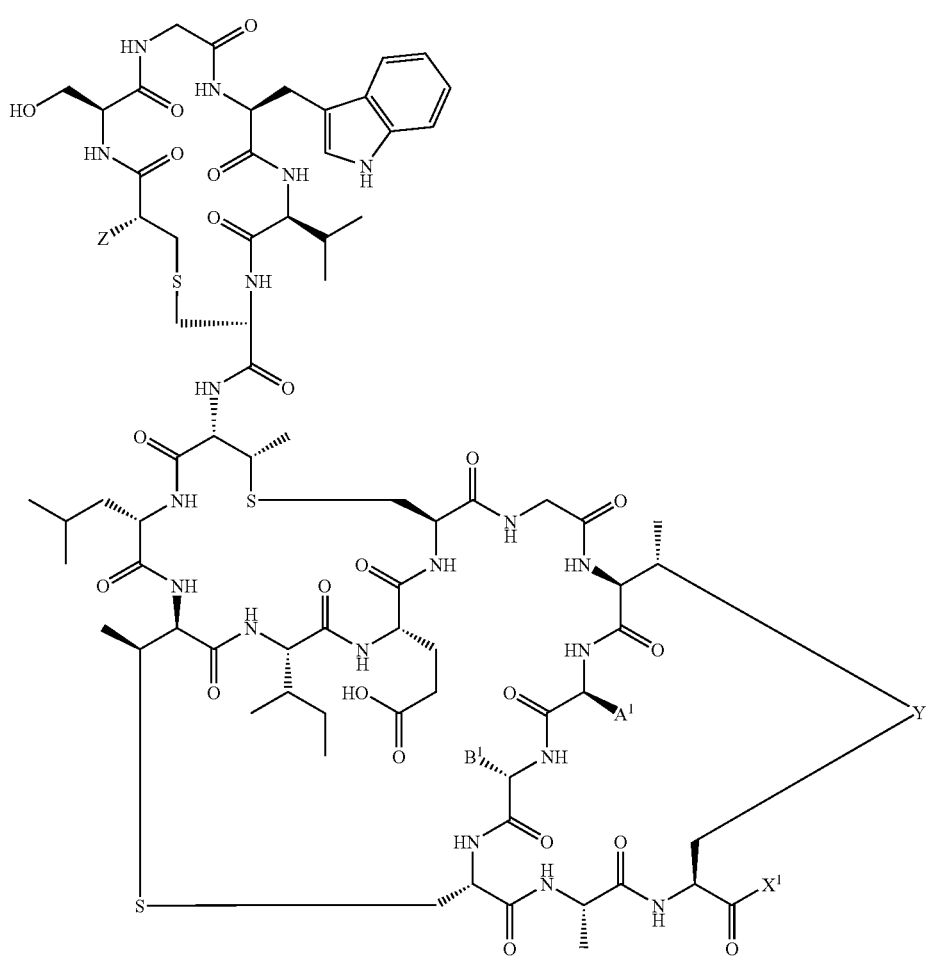

wherein:
A¹ is —$C_{1-4}$ alkyl;
B¹ is —$C_{1-4}$ alkyl;
X¹ is —OH or —$NR^{1A}R^{2A}$, wherein $R^{1A}$ represents hydrogen, or an alkyl or heteroalkyl group, substituted by at least one hydroxyl substituent, and $R^{2A}$ represents hydrogen, or an alkyl or heteroalkyl group, substituted by at least one hydroxyl substituent, or $R^{1A}$ and $R^{2A}$ taken together with the nitrogen atom represent a heterocyclic group having at least one hydroxyl substituent, wherein the heterocyclic group optionally further contains one or more heteroatoms, or $R^{1A}$ and $R^{2A}$ independently represent:
(1) hydrogen;
(2) a group of formula —$(CH_2)_n$—$NR^{11}R^{12}$, in which n represents an integer from 2 to 12 and $R^{11}$ and $R^{12}$ independently represent hydrogen or ($C_1$-$C_4$) alkyl or $R^{11}$ and $R^{12}$ taken together represent a group —$(CH_2)_3$—, —$(CH_2)_4$—, —$(CH_2)_2$—O—$(CH_2)_2$—, —$(CH_2)_2$—S—$(CH_2)_2$— or —$(CH_2)_5$—;
or $R^{1A}$ and $R^{2A}$ taken together with the adjacent nitrogen atom represent a piperazine moiety which may be substituted in position 4 with a substituent selected from:
(a) ($C_1$-$C_4$)alkyl;
(b) ($C_5$-$C_7$)-cycloalkyl,
(c) pyridyl,
(d) —$(CH_2)_p$—$NR^{13}R^{14}$ in which p represents an integer from 1 to 8 and $R^{13}$ and $R^{14}$ independently represent hydrogen or ($C_1$-$C_4$) alkyl;
(e) piperidinyl;
(f) substituted piperidinyl, wherein the substituted piperidinyl bears a N-substituent which is ($C_{1-4}$)alkyl;
(g) benzyl; and
(h) substituted benzyl, wherein the phenyl moiety bears 1 or 2 substituents selected from chloro, bromo, nitro, ($C_1$-$C_4$)alkyl and ($C_1$-$C_4$)alkoxy;
Z is an amino acid residue,
—$NR^3R^4$, —$NR^5R^5COR^6$, —$NR^5C(O)OR^6$; —$NR^5SOR^6$, —$NR^5SO_2R^6$; —$NR^5C(S)NR^6R^7$, —$NR^5C(NR^8)NR^6R^7$, or —N=$R^9$, wherein each of these groups represents modifications of the N-terminus of the amino acid at position 1, and where $R^3$, $R^4$, $R^5$, $R^6$, $R^7$, $R^8$ and $R^9$ are independently hydrogen, or a group, optionally substituted, selected from alkyl, heteroalkyl, aryl, heteroaryl, aralkyl and heteroaralkyl, with the proviso that $R^9$ is not hydrogen; and
Y is —S— or —S(O)—;
or a pharmaceutically acceptable salt, hydrate or solvate thereof. Variants and biologically active derivatives of these compounds may also be used in the methods of the present invention.

In one embodiment, the compound of formula (Ia) is an actagardine compound of formula (Ib):

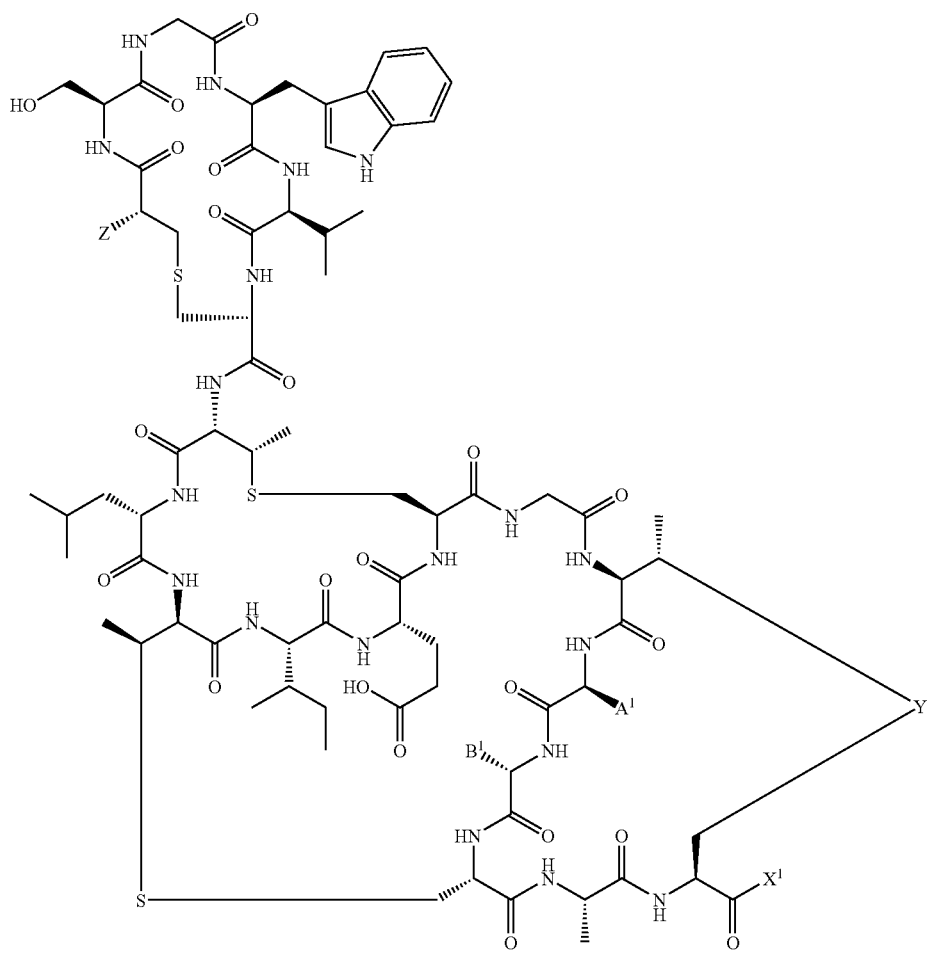

(Ib)

wherein:
- $A^1$ is —$C_{1-4}$ alkyl;
- $B^1$ is —$C_{1-4}$ alkyl;
- $X^1$ is —$NR^{14}R^{2A}$;
  where $R^{14}$ is a group of formula —$(CH_2)_n$—$NR^{11}R^{12}$, in which n represents an integer from 2 to 12, and $R^{11}$ and $R^{12}$ are each hydrogen;
  $R^{2A}$ is hydrogen;
- Z is an amino acid residue or a modification to the N-terminus of the amino acid at position 1, —$NR^3R^4$, where $R^3$ is hydrogen or $C_{1-4}$ alkyl, and $R^4$ is hydrogen or $C_{1-4}$ alkyl; and
- Y is —S(O)—;

or a pharmaceutically acceptable salt, hydrate or solvate thereof. Variants and biologically active derivatives of these compounds may also be used in the methods of the present invention.

In one embodiment in compounds of formula (Ib) A has a structure corresponding to an alkyl side chain of a natural amino acid containing up to 4 carbons.

In one embodiment in compounds of formula (Ib) A is —$CH_3$.

In one embodiment in compounds of formula (Ib) A is a branched chain alkyl, for example —$CH(CH_3)_2$, —$CH_2CH(CH_3)_2$, or —$CH(CH_3)CH_2CH_3$ such as —$CH(CH_3)_2$ or —$CH(CH_3)CH_2CH_3$, particularly —$CH(CH_3)_2$.

In one embodiment in compounds of formula (Ib) B has a structure corresponding to an alkyl side chain of a natural amino acid containing up to 4 carbons.

In one embodiment in compounds of formula (Ib) B is —$CH_3$.

In one embodiment in compounds of formula (Ib) B is a branched chain alkyl, for example —$CH(CH_3)_2$, —$CH_2CH(CH_3)_2$, or —$CH(CH_3)CH_2CH_3$, such as —$CH(CH_3)_2$ or —$CH(CH_3)CH_2CH_3$, particularly —$CH(CH_3)CH_2CH_3$.

In one aspect in compounds of formula (Ib) A is —$CH(CH_3)_2$ and B is —$CH(CH_3)CH_2CH_3$.

In one embodiment in compounds of formula (Ib) $R^3$ is H.

In one embodiment in compounds of formula (Ib) $R^4$ is H.

In one embodiment in compounds of formula (Ib) Z is an amino acid. The amino acid is the L or D isomer form of an amino acid residue.

In one embodiment in compounds of formula (Ib) Z is an amino acid residue selected from alanine, cysteine, aspartic acid, glutamic acid, phenylalanine, glycine, histidine, isoleucine, lysine, leucine, methionine, asparagine, proline, glutamine, arginine, serine, threonine, valine, tryptophan and tyrosine.

In one embodiment in compounds of formula (Ib) Z is an amino acid residue selected from phenylalanine, tyrosine and alanine.

In one embodiment in compounds of formula (Ib) Z is —$NH_2$.

In one aspect in compounds of formula (Ib) A is —CH$_2$CH(CH$_3$)$_2$ and B is —CH(CH$_3$)$_2$ and Z$^1$ is —NH$_2$.

In one embodiment in compounds of formula (Ib) n is 2, 3, 4, 5, 6, 7, 8, 9, 10, 11 or 12, such as 2, 3, 7, 9 or 12, in particular 7, 9 or 12.

In one embodiment in compounds of formula (Ib) n is 3 to 12 or 3 to 8.

In one aspect the disclosure provides use of a compound of formula (Ic):

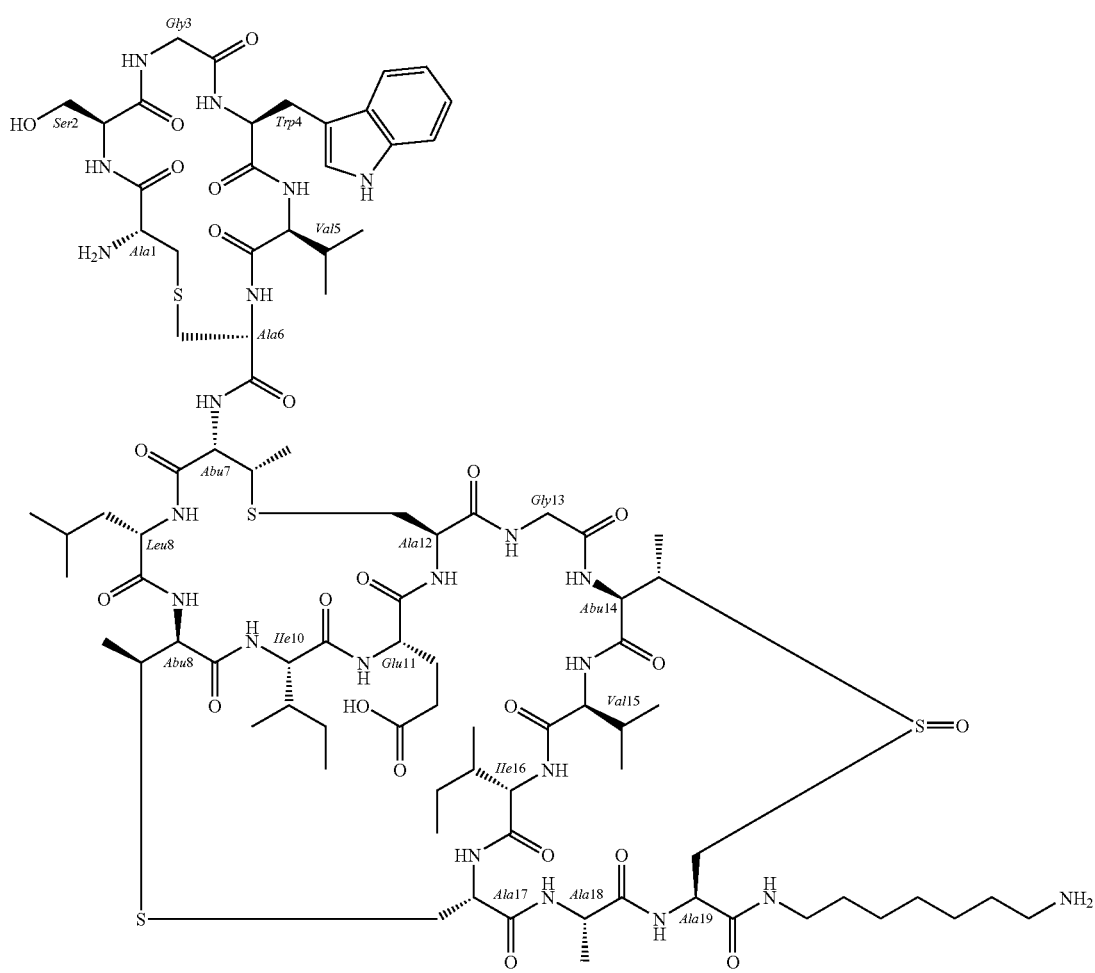

(Ic)

or a pharmaceutically acceptable salt, hydrate or solvate thereof, in particular for use in the treatment of *C. difficile* and/or bacterial overgrowth, for example in the small intestines and/or colon.

Specific Compounds

Examples of actagardine compounds of formula (Ia) and (Ib) for use in the invention are described below.

Examples for R$^3$, R$^4$, R$^5$, R$^6$, R$^7$, R$^8$, R$^9$, and R$^{11}$ and R$^{12}$ described above for the compounds of formula (I) also apply to the compounds of formula (Ia) and (Ib), where appropriate.

In one embodiment, the group R$^{1A}$ has the same meaning as R$^1$, where appropriate.

In one embodiment, the group R$^{2A}$ has the same meaning as R$^2$, where appropriate.

In one embodiment, the group X$^1$ has the same meaning as X, where appropriate.

In one embodiment, the group A$^1$ is a Leu; Val; or Ile amino acid side chain.

In one embodiment, the group B$^1$ is a Leu; Val; or Ile amino acid side chain.

Additionally, or alternatively, the following examples apply to the compounds of formula (Ia) and (Ib):

In one embodiment A$^1$ has a structure corresponding to an alkyl side chain of a natural amino acid containing up to 4 carbons.

In one embodiment, A$^1$ is —CH$_3$.

In one embodiment, A$^1$ is a branched chain alkyl, for example —CH(CH$_3$)$_2$, —CH$_2$CH(CH$_3$)$_2$, or —CH(CH$_3$)CH$_2$CH$_3$ such as —CH(CH$_3$)$_2$ or —CH(CH$_3$)CH$_2$CH$_3$, particularly —CH(CH$_3$)$_2$.

In one embodiment, A$^1$ is selected from —CH(CH$_3$)$_2$, —CH$_2$CH(CH$_3$)$_2$ and —CH(CH$_3$)CH$_2$CH$_3$.

In one embodiment, A$^1$ is selected from —CH(CH$_3$)$_2$ and —CH$_2$CH(CH$_3$)$_2$.

In one embodiment, A$^1$ is —CH(CH$_3$)$_2$.

In one embodiment B$^1$ has a structure corresponding to an alkyl side chain of a natural amino acid containing up to 4 carbons.

In one embodiment, B$^1$ is —CH$_3$.

In one embodiment B$^1$ is a branched chain alkyl, for example —CH(CH$_3$)$_2$, —CH$_2$CH(CH$_3$)$_2$, or —CH(CH$_3$)CH$_2$CH$_3$, such as —CH(CH$_3$)$_2$ or —CH(CH$_3$)CH$_2$CH$_3$, particularly —CH(CH$_3$)CH$_2$CH$_3$.

In one embodiment, $B^1$ is selected from —CH(CH$_3$)$_2$, —CH$_2$CH(CH$_3$)$_2$ and —CH(CH$_3$)CH$_2$CH$_3$.

In one embodiment, $B^1$ is selected from —CH(CH$_3$)$_2$ and —CH(CH$_3$)CH$_2$CH$_3$.

In one embodiment, $B^1$ is —CH(CH$_3$)CH$_2$CH$_3$.

In one embodiment, $A^1$ is —CH(CH$_3$)$_2$ and $B^1$ is —CH(CH$_3$)CH$_2$CH$_3$.

In one embodiment, n is 2, 3, 4, 5, 6, 7, 8, 9, 10, 11 or 12.

In one embodiment, n is 2, 3, 7, 9 or 12.

In one embodiment, n is 7, 9 or 12.

In one embodiment, n is 3 to 12 or 3 to 8.

In one embodiment, Z is —NH$_2$.

In one embodiment, Z is —NR$^5$C(O)OR$^1$.

In one embodiment, Z is an amino acid.

In one embodiment, the amino acid is the L or D isomer form of an amino acid.

In one embodiment, the amino acid is selected from alanine, cysteine, aspartic acid, glutamic acid, phenylalanine, glycine, histidine, isoleucine, lysine, leucine, methionine, asparagine, proline, glutamine, arginine, serine, threonine, valine, tryptophan and tyrosine.

In one embodiment, the amino acid is the L or D isomer form of alanine.

References herein to a compound employed in the disclosure include both compounds of formula (Ia), (Ib) or (Ic) and their pharmaceutically acceptable salts and derivatives.

Each and every compatible combination of the embodiments described above, is explicitly disclosed herein, as if each and every combination was individually and explicitly recited.

Examples of Structures

Suitably the type-B lantibiotic is an actagardine compound selected from the group below:

Compound C: Actagardine (7-amino-1-heptylamide monocarboxamide)

Compound CI: Actagardine 1,3-diaminopropane monocarboxamide

Compound CII: Actagardine 1,4-diaminobutane monocarboxamide

Variants

Compounds for use in the present invention include variants of compounds of formula (I).

A variant of a compound described herein includes a compound in which one or more, for example from 1 to 5, such as 1, 2, 3 or 4 amino acids, are substituted by another amino acid.

For compounds of formula (I) the amino acid is preferably at a position selected from positions 2, 3, 4, 5, 8, 10, 11, 13, 15, 16 or 18 of the compound of formula (I).

Substitutions may be of one amino acid by another naturally occurring amino acid and may be conservative or non-conservative substitutions. Conservative substitutions include those set out in the following table, where amino acids on the same block in the second column and preferably in the same line in the third column may be substituted for each other:

| ALIPHATIC | Non-polar | G A |
| | | I L V |
| | Polar - uncharged | C S T M |
| | | N Q |
| | Polar - charged | D E |
| | | K R |
| AROMATIC | | H F W Y |

Alternatively, an amino acid may be substituted by one of the modified, non-natural or unusual amino acids described above.

A variant of a compound of formula (I) may include a compound where a threonine derived residue participating in a thionine bridge (denoted Abu) is replaced with a serine-derived residue (Ala), for example the residue at position 7. Likewise a serine derived residue participating in a thionine bridge (denoted Ala) is substituted with a threonine-derived residue (Abu), for example the residue at position 1. Thus the variants for use in the invention include compounds where the Beta-methyllanthionine crosslink is substituted for a lanthionine crosslink, and vice versa. One, two or three crosslinks may be substituted in this manner.

A variant of a compound for use in the invention may include a compound additionally or alternatively having a crosslink other than a thionine bridge. Alternative bridges include, where appropriate, di-sulfide bridges, and amide and ester bridges (so-called macrolactam and macrolactone variants respectively).

Compounds for use in the present invention also include variants of compounds of formula (Ia), (Ib) and (Ic).

Derivatives

Derivatives of compounds for use in the invention (including variants) are those in which one or more amino acid side chain of the compound of the invention has been modified, for example by esterification, amidation or oxidation.

Derivatives of compounds of the invention may be monoamide derivatives at one of the carboxy functions of an actagardine compound of formula (I). A derivative may include a compound in which the carboxy function of a side chain of an internal residue, e.g. that of the residue Glu11 in actagardine, is modified from —COOH to a group —COOR$_9$ in which R$_9$ represents hydrogen, (C$_1$-C$_4$)alkyl or (C$_1$-C$_4$)alkoxy (C$_2$-C$_4$) alkyl. Alternatively, the carboxy function of a side chain of an internal residue e.g. that of the residue Glu11, is modified from —COOH to a group CONR$_1$R$_2$ where R$^1$ and R$^2$ are defined as above in relation to the C-terminus amide substituents.

N-terminal derivatives of compounds of the invention may be those in which the N-terminal amino group —NH$_2$ is instead a group —NHR$_{10}$ wherein R$_{10}$ represents C$_{1-4}$alkyl. Compound (I) is shown with crosslinks CROSSLINK 1-6, Lanthionine (Ser-Cys); CROSSLINK 7-12, Beta-methyl-lanthionine (Thr-Cys); and CROSSLINK 9-17, Beta-methyl-lanthionine (Thr-Cys). One, two or three of these crosslinks may be thionine sulfoxide crosslinks.

Compound (I) is also shown with a CROSSLINK 14-19, Beta-methyllanthionine sulfoxide (Thr-Cys). In a derivative of compound (I), one, two, three or four of the crosslinks may not be present.

Suitably there is at least one or more thionine or thionine sulfoxide crosslinks present.

Compounds for use in the present invention include derivatives of compounds of formula (Ia), (Ib) and (Ic). The derivatives are compounds of formula (Ia), (Ib) and (Ic) modified as described above in relation to the compounds of formula (I).

Synthesis of Actagardine Compounds

The inventors have previously described methods for the preparation of actagardine compounds, and derivatives and variants thereof. The inventors' co-pending earlier application PCT/GB2007/000138 (WO/2007/083112) is hereby incorporated by reference in its entirety. The compounds described in this document may be used as starting materials for the compounds for use in the present invention, or they may find use in the methods of the present invention.

The compounds described herein may be used as starting materials for the synthesis of other compounds for use in the invention.

The actagardine compounds for use in the invention may be prepared from known actagardine compounds. Preferably, the actagardine compounds of the invention are prepared from actagardine, actagardine B and deoxyactagardine B. These lantibiotics may be referred to as a 'parent lantibiotic' or a 'lantibiotic starting material'.

An actagardine compound may be produced by expression of a nucleic acid, for example in the form of an expression construct encoding a precursor polypeptide carried in a recombinant expression vector, in a host cell which carries an appropriate lantibiotic gene, such as the LanA gene, together with, where necessary, associated cluster genes required for conversion of a precursor polypeptide to an actagardine compound. Variant actagardine compounds may be produced by appropriate modification of the LanA gene using methods known per se in the art.

The LanO gene, which has been identified as part of the actagardine gene cluster, is thought to encode the protein responsible for the oxidation of the deoxy-form of actagardine compounds to actagardine in which Y is —S(O)—. Modification of this gene may allow the production of derivative compounds having an alternative crosslinked structure. Modification of the LanO gene also allows the relative levels of oxidized (Y=S(O)—) and reduced (Y=S—) forms of the compounds produced in the host cell to be altered.

The LanM gene, which has also been identified as part of the actagardine gene cluster, is thought to encode the protein required for the conversion of a precursor polypeptide to a lantibiotic compound. Modulation of this gene, and other genes encoding modification proteins, may allow the production of derivative compounds having an alternative crosslinked structure. Modulation of these genes may also allow the production of compounds having or retaining an amino acid sequence attached to the N-terminus of the actagardine compound, such as a leader sequence.

Typically, those compounds produced by cell culture will have a free amine N-terminus (i.e. Z is —NH$_2$) and a free carboxylic acid C-terminus (i.e. X is —OH). These termini may be derivatised as described in more detail below. Where an actagardine compound has a modified N-terminus, the starting material will typically have a free amine N-terminus. It will be appreciated that the compounds produced by cell culture may have a modified N-terminus. Thus, a compound for use as a starting material may include a compound where Z is —NHR$^3$, where R$^3$ is defined according to the compounds of formula (I).

Where the invention relates to the use of compounds derived from an actagardine compound starting material in which X1 and X2 represent Leu and Val respectively, the host cell may be *A. liguriae* NCIMB 41362 without any further modification.

Where host cells produce a mixture of starting material compounds, e.g. those in which Y is —S— or —S(O)—, the products may be isolated using standard separation techniques such as HPLC, e.g. as described in U.S. Pat. No. 6,022,851 for the production of actagardine and Ala(0)-actagardine.

Following culture of host cell which carries an appropriate lantibiotic gene, the type-B lantibiotic compounds for use in the invention may be recovered from the host cell culture, and optionally modified. The recovered and/or modified compounds may be formulated in the form of a pharmaceutical composition, optionally in the form of a pharmaceutically acceptable salt.

Actagardine may be recovered from a culture medium by standard techniques in the art, such as separation from other components of the culture medium by chromatographic means. Such means include the use of hydrophobic resins, reversed phase chromatography, ion exchange chromatography and HPLC.

Alternatively, the lantibiotic starting material, or the variants and derivatives thereof, may be obtained by chemical peptide synthesis, for example solid-phase peptide synthesis (SPPS). Such techniques are well known in the art. However, the lantibiotic starting material is preferably obtained by cell culture.

The compounds for use in the invention may be in substantially isolated form. Isolated compounds will be those as defined above in isolated form, free or substantially free of material with which it is associated such as polypeptides from which the compounds are derived. The compounds may of course be formulated with diluents or adjuvants and still for practical purposes be isolated.

A compound for use in the invention may also be in a substantially purified form, in which case it will generally comprise the compound in a preparation in which more than 90%, e.g. 95%, 98% or 99% of the compound in the preparation is a compound of the invention.

The C-terminus-modified actagardine compounds for use in the invention may be prepared by reacting a lantibiotic starting material having a carboxyl C-terminus with a 2 to 6-fold molar excess of an appropriate amine group, in a suitable organic solvent such as dimethylformamide at a temperature typically between 0° C. and room temperature and in the presence of a suitable condensing agent. Representative examples of condensing agents are carbodiimide derivatives such as dicyclohexylcarbodiimide, phosphoazidates such as DPPA or benzotriazole-based coupling reagents such as PYBOP™, HATU or TBTU.

Compounds for use in the invention where Z is an amino acid or —NR$^5$COR$^6$ may be prepared from a lantibiotic starting material having an amino group N-terminus by means of a coupling reaction with an appropriate carboxylic acid in the presence of a condensing agent such as dicyclohexylcarbodiimide, phosphoazidates such as DPPA or benzotriazole-based coupling reagents such as PYBOP™, HATU or TBTU. An organic amine base, such as triethylamine or diisopropylethylamine is generally added to expedite the reaction.

Alternatively, preformed activated derivatives of the appropriate acid, such as the pentafluorophenyl esters, may be used as reagents to react with the lantibiotic N-terminus. A catalyst, such as HOBt may be added to expedite the reaction. The solvent is typically DMF.

Where the carboxylic acid being coupled to the lantibiotic contains further functional groups that may interfere with the coupling reaction, suitable protection groups familiar to those skilled in the art may be employed. For example, Fmoc or tBoc protection groups may be employed for amino acid derivatives to be coupled to the N-terminus of the lantibiotic.

Compounds for use in the invention where Z is —NR$^3$R$^4$ may be prepared from a lantibiotic having an amino group N-terminus by means of a coupling reaction with an aldehyde or ketone in an organic solvent, such as dichloromethane, dimethylsulphoxide or acetic acid, in the presence of a suitable reducing agent, such as sodium borohydride or sodium triacetoxyborohydride. Such reducing agent may be used in solution or bound to a suitable resin, such as polystyrene. Depending on the reaction conditions, the aldehyde or ketone employed and the ratio of the reagents employed in the reaction, both mono- and di-alkylation of the N-terminus are possible. Alternatively, the reaction may be performed without a reducing agent. In which case it is possible to obtain compounds of the invention where Z is —N=R$^9$.

Compounds for use in the invention where Z is —NR$^5$C(O)OR$^6$; —NR$^5$SOR$^6$, —NR$^5$SO$_2$R$^6$; —NR$^5$C(S)NR$^6$R$^7$ or —NR$^5$C(NR$^1$)NR$^6$R$^7$ may be prepared from a lantiobiotic starting material having an amino group N-terminus by means of a coupling reaction with an appropriately activated substituent group reagent. Thus, compounds where Z is —NR$^5$C(O)OR$^1$, may be prepared using ClC(O)OR$^1$ and such like. Similarly, compounds where Z is —NR$^5$SO$_2$R$^6$ may be prepared using ClSO$_2$R$^6$. The activated substituent group reagent may include additional functionality that is protected with a protecting group. The protecting group may be removed after the coupling reaction as appropriate.

The actagardine compounds for use in the invention may be modified at both the N-terminus and the C-terminus. These compounds may be prepared from starting materials that are modified at either the C-terminus or N-terminus. The other terminus may then be modified to provide the compounds for use in the invention. Thus, the sequence of substitutions can either feature N-terminal modification followed by C-terminal modification, or vice versa. Where issues of regioselectivity arise, for instance where the C-terminal substituent features an amino group, a suitable protection strategy may be employed.

Thus, a lantibiotic starting material where the N-terminus of the compound is an amino acid residue, —NR$^3$R$^4$, —NR$^5$COR$^6$, —NR$^5$C(O)OR$^6$; —NR$^5$SOR$^6$, —NR$^5$SO$_2$R$^6$, —NR$^5$C(S)NR$^6$R$^7$, —NR$^5$C(NR$^8$)NR$^6$R$^7$, or —N=R$^9$ (as defined previously in relation to the compounds of the invention), may equally be coupled with amino alcohols at the C-terminal.

The inventors have observed that under the coupling conditions used to couple an amino alcohol to the carboxyl C-terminus of a parent lantibiotic, the carboxyl group of a side chain amino acid residue, such as glutamic acid, may also be modified. Such compounds where both the C-terminus and a side chain of an amino acid are modified also find use in the present invention. Appropriate manipulation of the reaction conditions may be used to alter the amount of product that is obtained with a modified side chain. Alternatively a protection and deprotection strategy may be employed to ensure that the side chain is not modified. Suitable amino acid residue side chain protecting groups are well known and include the protecting groups mentioned above.

Variants of actagardine where a threonine residue is substituted with a dehydrobutyrine amino acid reside may be prepared by chemical dehydration of a threonine residue. For example, the threonine residue may be treated with EDC in the presence of CuCl. A similar reaction has been described previously for the dehydration of a threonine residue in nisin (see Fukase, K et al *Bull. Chem. Soc. Jpn.* 1992, 65, 2227-2240). The method may be adapted to prepare a dehydroalnanine residue from a serine residue.

Derivatives having alternative crosslinks present may be prepared by the cyclistation of appropriate amino acid residues e.g. the side chains of cysteine residues may be used for disulfide bridge formation. Macrolactamisation, macrolactonisation and disulfide bridge formation techniques are well known to those of skill in the art of peptide synthesis.

Reaction products may be identified by LC-MS. Reaction progression may be monitored by HPLC. HPLC may be used to monitor the consumption of the starting material, the appearance of the product and the production of side or decomposition products (if any).

The products and the starting material may be analysed by NMR spectroscopy. Such techniques have been described previously by the present inventors in relation to the preparation of actagardine compounds, variants and derivatives. The structure of the product lantibiotic-based compound may be confirmed using standard techniques such as COSY, HMBC, TOCSY, HSQC and NOESY, as well as NOE techniques.

Mersacidin

For use in the present invention there is provided a mersacidin compound of formula (II):

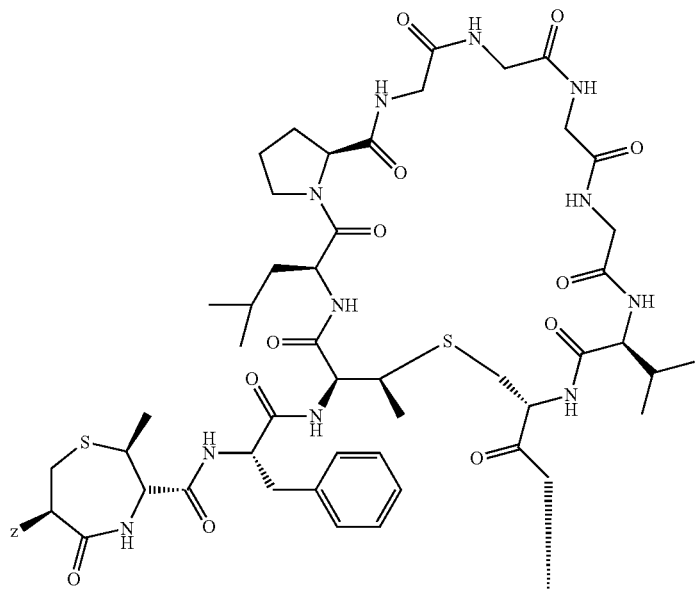

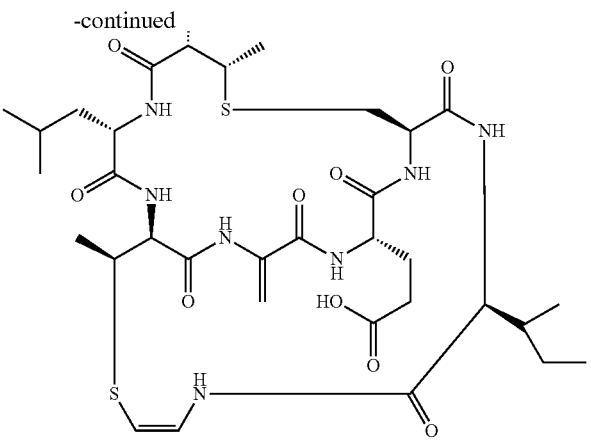

where Z is as defined below.

Alternatively, the structure of the compound of formula (II) may be represented conveniently thus:

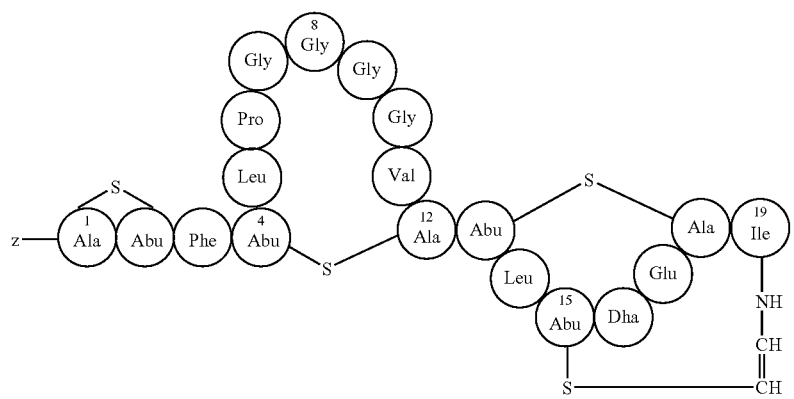

wherein Z is defined according to the group Z for compounds of formula (I), or a pharmaceutically acceptable salt thereof. Dha is a dehydroalanine residue. Variants and biologically active derivatives of these compounds may also be used in the methods of the present invention.

Where Z is —NH$_2$ the compound is mersacidin.

Compounds

Suitable mersacidin compounds of formula (II) for use in the invention are described below.

Examples of R $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ may be optionally substituted or optionally further substituted as appropriate.

Examples of Z

Examples of Z are the same as those described for the actagardine compounds of formula (I).

In one embodiment, Z is an amino acid or —NH$_2$.

In one embodiment, Z is —NH$_2$.

Examples of Structures

Suitably the type-B lantibiotic is a mersacidin compound selected from the group below:

Compound I: Mersacidin

Variants Compounds for use in the present invention include variants of compounds of formula (II).

A variant of a compound described herein includes a compound in which one or more, for example from 1 to 10, such as 1, 2, 3 or 4 amino acids, are substituted by another amino acid.

For compounds of formula (II) the amino acid preferably at a position selected from positions 3, 5, 6, 7, 8, 9, 10, 11, 14, 16, 17 or 19 of the compound of formula (II).

Substitutions may be of one amino acid by another naturally occurring amino acid and may be conservative or non-conservative substitutions as described in relation to the variants of compounds of formula (I). Alternatively, an amino acid may be substituted by one of the modified, non-natural or unusual amino acids described above.

Preferred mersacidin variants for use in the methods of the invention include compounds comprising a modification to position 3, 5, 6, 7, 8, 9, 10, 11, 14 or 16 of mersacidin as set out in Table 2 below:

TABLE 2

Mersacidin Variants

| F3  | L5  | P6  | G7  | G8  | G9  | G10    | V11  | L14  | Dha16    |
|-----|-----|-----|-----|-----|-----|--------|------|------|----------|
| F3W | L5A | P6H | G7A | G8A | G9A | G10A   | V11L | L14V | Dha16G   |
| F3R | L5I | P6A | G7N | G8C | G9S | G10V   | V11I | L14I | Dha16A   |
| F3D | L5M | P6N | G7Q | G8N | G9T | G10S   | V11M | L14M | Dha16Dhb |
| F3I | L5N | P6Q | G7W | G8Q | G9N | G10Dha | V11K |      | Dha16H   |
| F3P | L5H | P6V | G7S | G8H | G9R | G10M   | V11C |      |          |
| F3S |     | P6M | G7T | G8E | G9Y | G10Y   |      |      |          |
| F3C |     | P6F | G7M | G8I | G9H | G10W   |      |      |          |
| F3M |     | P6Y | G7I | G8S | G9Q | G10I   |      |      |          |
| F3N |     | P6G | G7H | G8P | G9L | G10Dhb |      |      |          |
| F3H |     | P6L | G7F |     |     | G10R   |      |      |          |
|     |     | P6I |     |     |     | G10K   |      |      |          |
|     |     | P6D |     |     |     | G10H   |      |      |          |
|     |     | P6E |     |     |     | G10N   |      |      |          |

Where the numbers refer to the numbering of the mature mersacidin peptide sequence and the letters are the 1-letter amino acid code, and Dha is dehydroalanine and Dhb is dehydrobutyrine. When these modified amino acid residues are present, this is due to post-translational modification of serine and threonine residues respectively.

The mersacidin variants may comprise a combination of two or more of the above modifications, for example from 1 to 4, such as 2 or 3 of the modifications (with the remaining residues being that of the wild-type mersacidin sequence). Thus, a variant comprising any one of the above-mentioned modifications may be a variant consisting of two, three or four changes in combination, or just consisting of a single positional change.

The inventors have previously reported that the change F3W provides a mersacidin variant ("mersacidin F3W") which has activity against a range of microorganisms which is more potent than mersacidin itself. Thus, the mersacidin variant may comprise F3W together with one, two or three other changes. Such mersacidins include mersacidin F3W G8A, mersacidin F3W G9A, mersacidin F3W G9H, mersacidin F3W V11I, mersacidin F3W V11L, mersacidin F3W L14I, mersacidin F3W L14M, mersacidin F3W L14V, mersacidin F3W Dha16G and mersacidin F3W Dha16Dhb.

Variants of compounds of formula (II) include those compounds lacking the seven-membered thionine ring at the N-terminus region. Such variants include compounds having a residue other than a cysteine residue at position 1, or compounds having a residue other than threonine at position 2. Other variants may have a thionine ring at the N-terminus region where the threonine residue at position 2 is substituted with a serine residue. Thus the beta-methyllanthionine crosslink is substituted for a lanthionine crosslink.

A variant of a compound of formula (II) may include a compound where a threonine derived residue participating in a thionine bridge (denoted Abu) is replaced with a serine-derived residue (Ala), for example the residue at position 4 or position 13. Thus the variants for use in the invention include compounds where the Beta-methyllanthionine crosslink is substituted for a lanthionine crosslink. One, two or three crosslinks may be substituted in this manner.

Another variant includes the substitution of the aminovinyl-cysteine amino acid residue (Avi-Cys) at position 20 with a cysteine residue. Where this residue is a cysteine residue, the C-terminus may be a carboxylic acid (—COOH) terminus. Alternatively, the C-terminus may be a group —CONR$^1$R$^2$, where R$^1$ and R$^2$ are defined above in relation to the actagardine compounds of formula (I).

A variant of a mersacidin compound for use in the invention may include a compound where a crosslink is a bridge other than a thionine bridge. Alternative bridges include, where appropriate, di-sulfide bridges, and amide and ester bridges (so-called macrolactam and macrolactone variants respectively).

Example Variant

Suitably the type-B lantibiotic is a mersacidin variant compound selected from the group below:

Compound IV: F3W Mersacidin

Derivatives

Compounds for use in the present invention include derivatives of compounds of formula (II).

Derivatives of compounds for use in the invention (including variants) are those in which one or more amino acid side chain of the compound of the invention has been modified, for example by esterification, amidation or oxidation.

A derivative may include a compound in which the carboxy function of a side chain of an internal residue is modified as explained in relation to compounds of formula (I) above. For example, residue Glu17 in mersacidin may be modified from —COOH to a group —COOR$_9$ in which R$_9$ represents hydrogen, $(C_1$-$C_4)$alkyl or $(C_1$-$C_4)$alkoxy $(C_2$-$C_4)$alkyl. Alternatively, the carboxy function of a side chain of an internal residue e.g. that of the residue Glu17, is modified from —COOH to a group CONR$_1$R$_2$ that is the same as X.

Compound (II) is shown with crosslinks CROSSLINK 1-2, Beta-methyllanthionine (Cys-Thr); CROSSLINK 4-12, Beta-methyllanthionine (Thr-Cys); CROSSLINK 13-18, Beta-methyllanthionine (Thr-Cys). One, two or three of these crosslinks may be thionine sulfoxide crosslinks.

Compound (II) is also shown with a CROSSLINK 15-19, (Thr-S—CHCH—NH-Ile). In a derivative of compound (II), one, two, three or four of the crosslinks may not be present.

Preferably there is at least one or more thionine or thionine sulfoxide crosslinks present.

Synthesis of Mersacidin Compounds

The synthesis of mersacidin compounds has been described previously by the present inventors in their co-pending application WO 2007/036706. The compounds described in this document may be used as starting materials for the compounds for use in the present invention, or they may find use in the methods of the present invention.

Mersacidin F3W, mersacidin G8A and mersacidin F3W G8A are also described in WO2005/093069 (PCT/GB2005/001055) filed 21 Mar. 2005 and claiming priority from 0406870.6 filed 26 Mar. 2004, the disclosures of which are incorporated herein by reference in their entirety.

Thus, mersacidin and variants thereof may be produced by culturing a host cell, for example a bacterial host cell, into which an mrs gene cluster has been integrated into the genome, wherein said cell produces mersacidin or a mersacidin variant. Preferably, the mrs gene cluster is SigH deficient. The construction of transformed host cells having a modified mrs gene cluster has been described previously by the inventors.

Variant merscacidin compounds may be produced by modification of the mrs gene cluster. Particularly, the mrsA gene, which encodes mersacdin, may be modified by site-directed mutagenesis using methods known per se in the art, e.g. as disclosed by Szekat et al., (2003) *Appl. Env. Microbiol.* 69, 3777-3783.

The mrsM gene, which has been identified as part of the mersacidin gene cluster, is thought to encode the protein responsible for posttranslationally modifying the translation product of the mrsA gene to introduce the lanthionine residues of mature cinnamycin. Modification of this gene may allow the production of derivative compounds having an alternative crosslinked structure.

Typically, those compounds produced by cell culture will have a free amine N-terminus (i.e. Z is —NH$_2$). The techniques and strategies for derivatising the N-terminus of mersacidin or variants thereof are the same as those described above in relation to the derivatisation of the N-terminus of actagardine. Thus, a compound having a modified N-terminus and/or modified C-terminus may be prepared from a mersacidin compound A suitable protecting group strategy may also be employed in the synthesis of mersacidin compounds. Such techniques are also discussed above in relation to actagardine. Regarding mersacidin, the side chain of the glutamic acid amino acid reside at position 17, for example, may be protected whilst the N-terminus is modified. The protecting group may then be removed, if required.

Compounds may be isolated, purified and identified using the methods described above in relation to actagardine.

Other Type-B Lantibiotics

Suitable for use in the invention are derivatives and variants of other type-B lantibiotics, as well as modified forms of these type-B lantibiotics. Also suitable for use in the invention are the pharmaceutically acceptable salts of these compounds. Particularly suitable examples include plantaricin, planosporicin, ruminococcin, antibiotic 10789, michiganin and haloduracin.

Another example of a type-B lantibiotic suitable for use in the present invention is lichenicidin. In one embodiment of the invention, lichenicidin may find use along with the preferred examples discussed above.

Each of the documents referred to below is incorporated herein in its entirety.

Plantaricin

The synthesis and identification of plantaricin compounds are described in Turner et al [*Eur. J. Biochem.* 1999, 264, 833]. Plantaricin C may be represented conveniently thus:

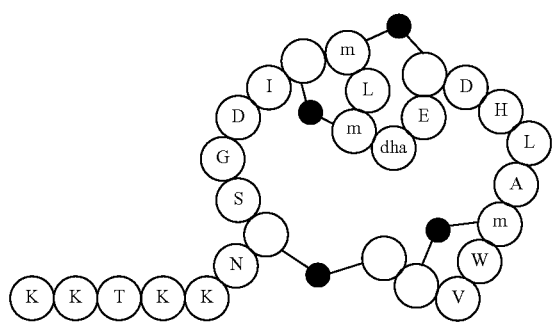

where an Ala residue is denoted by the empty circle, an Abu residue is denoted by the letter 'm' and the sulfur atom of a thionine bridge is shown as a filled circle. Dha is a dehydroalanine residue.

The N- and C-termini of a plantaricin C compound may be functionalised in a similar manner to the N- and C-termini of the actagardine compounds described above (where the N-terminus is represented by Z and the C-terminus is represented by X). Similarly, suitable for use in the present invention are derivatives and variants of plantaricin C.

A variant of a compound described herein includes a compound in which one or more, for example from 1 to 10, such as 1, 2, 3 or 4 amino acids, are substituted by another amino acid.

For plantaricin C, the amino acid is preferably at a position selected from positions 1, 2, 3, 4, 5, 6, 8, 9, 10, 11, 14, 17, 19, 20, 21, 22, 24 or 25 of the compound of the formula given above.

Planosporicin

The synthesis and identification of planosporicin compounds are described in Castiglione et al (*Biochemistry* 2007, 46, 5884-5895). Planosporicin may be represented conveniently thus:

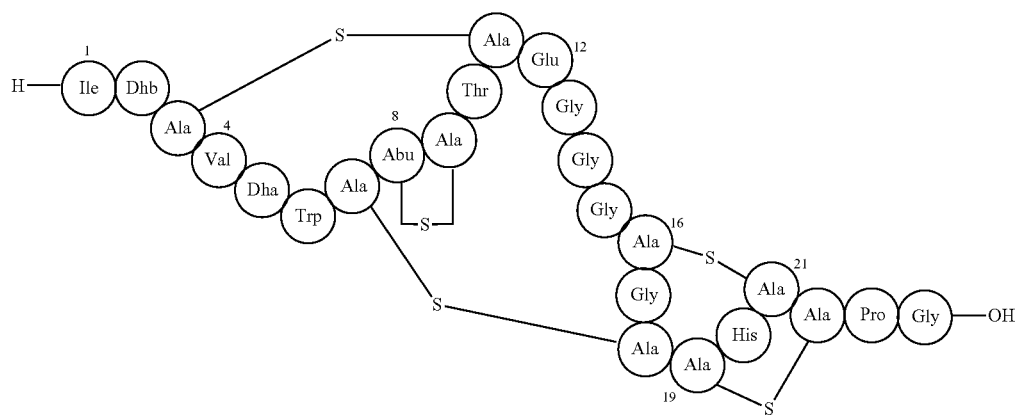

where Dha is a dehydroalanine residue and Dhb is a dehydrobutyrine residue.

The N- and C-termini of a planosporicin compound may be functionalised in a similar manner to the N- and C-termini of the actagardine compounds described above (where the N-terminus is represented by Z and the C-terminus is represented by X). Similarly, suitable for use in the present invention are derivatives and variants of planosporicin.

A variant of a compound described herein includes a compound in which one or more, for example from 1 to 10, such as 1, 2, 3 or 4 amino acid residues, are substituted by another amino acid residue.

For planosporicin, the amino acid is preferably at a position selected from positions 1, 2, 4, 5, 6, 10, 12, 13, 14, 15, 17, 20, 23 or 24 of the compound of the formula given above.

Rumminococcin

The synthesis and identification of rumminococcin compounds are described in Dabard et al [see *Appl. Environ. Microbiol.* 2001, 67, 4111]. Rumminococcin A may be represented conveniently thus:

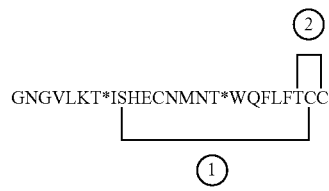

where T denotes a Dhb residue, and the lines represent thionine (1) and methylthionine (2) bridges.

The N- and C-termini of a ruminococcin A or B compound may be functionalised in a similar manner to the N- and C-termini of the actagardine compounds described above (where the N-terminus is represented by Z and the C-terminus is represented by X). Similarly, suitable for use in the present invention are derivatives and variants of ruminococcin A or B.

A variant of a compound described herein includes a compound in which one or more, for example from 1 to 10, such as 1, 2, 3 or 4 amino acids, are substituted by another amino acid.

For ruminococcin A, the amino acid is preferably at a position selected from positions 1, 2, 3, 4, 5, 6, 7, 8, 10, 11, 12, 13, 14, 15, 16, 17, 18, 19, 20 or 21 of the compound of the formula given above.

Haloduracin

The synthesis and identification of haloduracin compounds are described in McClerren et al [*Proc. Nat. Acad. Sci.* 2006, 103, 17243]. Haloduracin α may be represented conveniently thus:

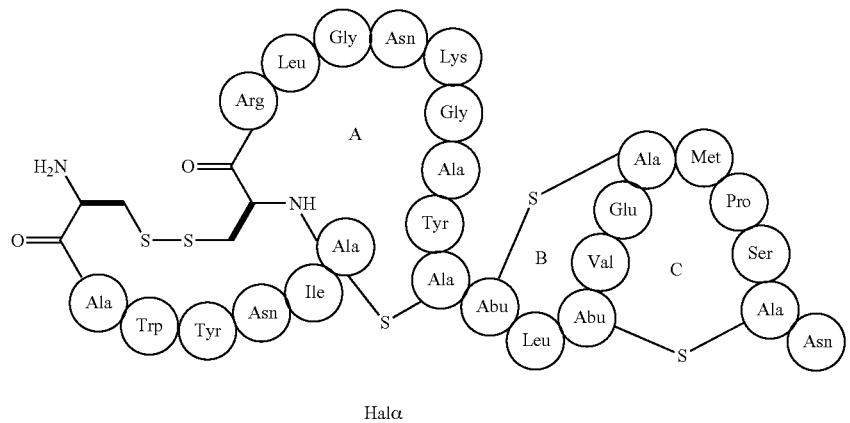

Halα

The N- and C-termini of a haloduracin compound may be functionalised in a similar manner to the N- and C-termini of the actagardine compounds described above (where the N-terminus is represented by Z and the C-terminus is represented by X). Also suitable for use in the present invention are derivatives and variants of haloduracin. Haloduracin α has a 1-8 disulfide bridge. This may be replaced with a thionine crosslink.

A variant of a compound described herein includes a compound in which one or more, for example from 1 to 10, such as 1, 2, 3 or 4 amino acids, are substituted by another amino acid.

For haloduracin, the amino acid is preferably at a position selected from positions 2, 3, 4, 5, 6, 9, 10, 11, 12, 13, 14, 15, 16, 19, 21, 22, 24, 25, 26 or 28 of the compound of the formula given above.

Antibiotic 107891

The synthesis and identification of antibiotic 107891 compounds are described in WO 2006/080920. The compounds described in WO 2006/080920 also find use in the present invention. Accordingly, a compound for use in the present invention is an antibiotic 107891 compound as represented thus:

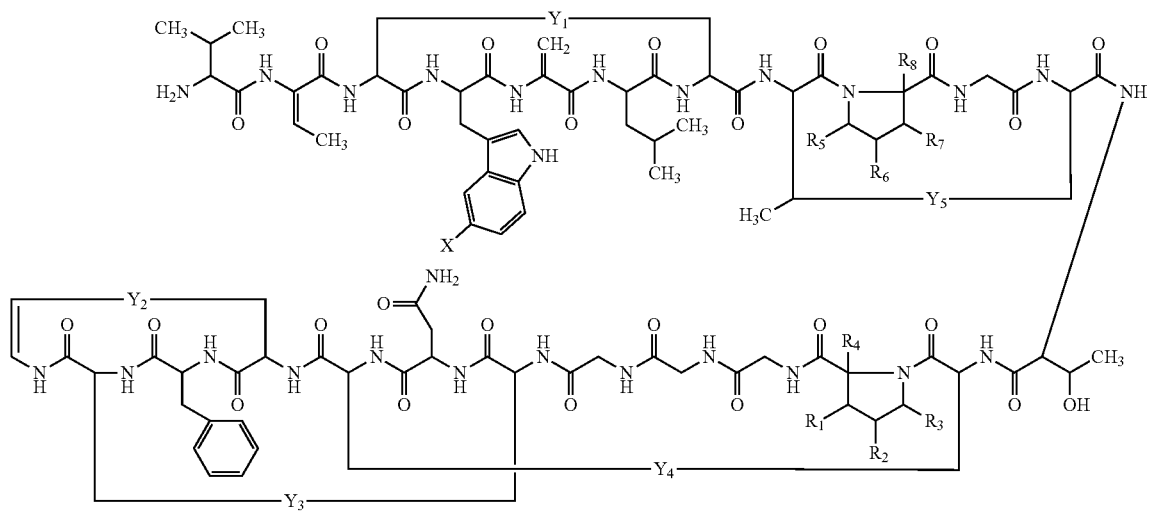

wherein X is selected from the group consisting of H, F, Cl, Br and I; each $Y_{1-5}$ is independently selected from the group consisting of S, S—O—, S═O, O—S═O and O═S═O; and each $R_{1-8}$ is independently selected from the group consisting of H, OH, alkyl and aryl.

The N-terminus of antibiotic 107891 may be functionalised in a similar manner to the N-terminus of the actagardine compounds described above (where the N-terminus is represented by Z). Similarly, suitable for use in the present invention are derivatives and variants of antibiotic 107891.

A variant of a compound described herein includes a compound in which one or more, for example from 1 to 10, such as 1, 2, 3 or 4 amino acids, are substituted by another amino acid.

For antibiotic 107891 A1, the amino acid is preferably at a position selected from positions 1, 2, 4, 5, 6, 9, 10, 11, 13, 14, 15, 17, 19 or 22 of the compound of the formula given above.

A variant for use in the invention includes the substitution of the aminovinyl-cysteine amino acid residue (Avi-Cys) at the C-terminus with a cysteine residue. Where this residue is a cysteine residue, the C-terminus may be a carboxylic acid (—COOH) terminus.

Alternatively, the C-terminus may be a group —CONR$^1$R$^2$, where R$^1$ and R$^2$ are defined above in relation to the actagardine compounds of formula (I).

Michiganin

The synthesis and identification of michiganin compounds are described in Holtsmark et al [APPL. ENVIRON. MICROBIOL. 2006, 72, 5814]. Michiganin A may be represented conveniently thus:

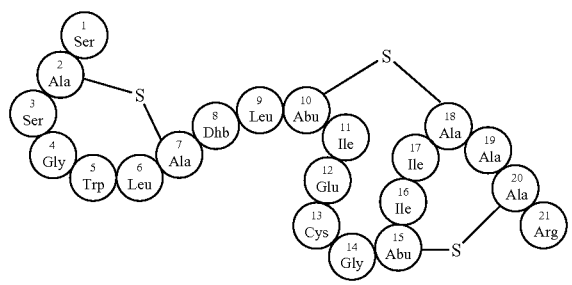

The N- and C-termini of a michiganin compound may be functionalised in a similar manner to the N- and C-termini of the actagardine compounds described above (where the N-terminus is represented by Z and the C-terminus is represented by X).

A variant of a compound described herein includes a compound in which one or more, for example from 1 to 10, such as 1, 2, 3 or 4 amino acids, are substituted by another amino acid.

For michiganin, the amino acid is preferably at a position selected from positions 1, 3, 4, 5, 6, 8, 9, 11, 12, 13, 14, 16, 17, 19 or 21 of the compound of the formula given above.

Lichenicidin

The synthesis and isolation of lichenicidin compounds are described in Rey et al [Genome Biology 2004, 5, R77]. Lichenicidin is a homolog of mersacidin.

The N- and C-termini of a lichenicidin compound may be functionalised in a similar manner to the N- and C-termini of the mersacidin compounds described above (where appropriate).

A variant of a compound described herein includes a compound in which one or more, for example from 1 to 10, such as 1, 2, 3 or 4 amino acids, are substituted by another amino acid.

GENERAL EXAMPLES

For each of the type-B lantibiotics described above, the lanthionine crosslink may be oxidised. Where appropriate a crosslink having an Abu residue may be substituted with an Ala residue, and vice versa.

The substitutions described above may be of one amino acid by another naturally occurring amino acid and may be conservative or non-conservative substitutions as described in relation to the variants of compounds of formula (I). Alternatively, an amino acid may be substituted by one of the modified, non-natural or unusual amino acid residues as described above.

General Syntheses

Each of the type-B lantibiotics described above may be prepared according to the preparations described in the respective publications cited above. Such compounds typically have a free amine N-terminus and a free carboxy C-terminus.

Where reference is made to a type-B lantibiotic compound having a functionalised N- and/or C-terminus, such compounds may be prepared by derivatising the free amine and/or free carboxy termini of a parent type-B lantibiotic as appropriate. The methods described above ion relation to the functionalisation of the actagardine N- and C-termini are also applicable to the type-B lantibiotics described here.

Where appropriate, the side chain functionalities of the amino acid residues within a type-B lantibiotic may be protected prior to the functionalisation of the N- and/or C-terminus. These protecting groups may be removed after the fictionalisation is complete. Protecting group strategy is discussed in relation to actagardine above and is also discussed in more detail below.

Includes Other Forms

Included in the compounds described are the well known isomeric, salt, solvate, protected forms and prodrugs. For example, a reference to carboxylic acid (—COOH) also includes the anionic (carboxylate) form (—COO$^-$), a salt or solvate thereof, as well as conventional protected forms. Similarly, a reference to an amino group includes the protonated form (—N$^+$HR$^1$R$^2$), a salt or solvate of the amino group, for example, a hydrochloride salt, as well as conventional protected forms of an amino group. Similarly, a reference to a hydroxyl group also includes the anionic form (—O$^-$), a salt or solvate thereof, as well as conventional protected forms of a hydroxyl group.

For example, reference to the carboxylic acid-containing side chain of glutamic acid (Glu), which features as a residue in the compounds for use in the invention, includes the carboxylate form. Where Z is —NH$_2$, reference to this group includes the protonated form of this amino group. Also, reference to X as —OH, includes reference to the carboxylate form of the alanine amino acid residue at position 19 of actagardine.

Isomers, Salts, Solvates, Protected Forms and Prodrugs

Isomers

Certain compounds may exist in one or more particular geometric, optical, enantiomeric, diasterioisomeric, epimeric, stereoisomeric, tautomeric, conformational, or anomeric forms, including but not limited to, cis- and trans-forms; E- and Z-forms; c-, t-, and r-forms; endo- and exo-forms; R—, S—, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

For example, the amino acid residues described herein may exist in any one of the particular stereoisomeric forms. Similarly, the R$^1$ and R$^2$ groups may exist in any one of the particular stereoisomeric forms, where such forms exist. Likewise, the groups R$^3$, R$^4$, R$^5$, R$^6$, R$^7$, R$^8$, R$^9$, R$^{10}$, R$^{11}$, R$^{12}$, R$^{13}$ and R$^{14}$ may exist in any one of the particular stereoisomeric forms, where such forms exist.

Where a compound for use in the invention includes a dihydroamino butyric acid residue, the residue may exist in either cis- or trans-forms.

If the compound is in crystalline form, it may exist in a number of different polymorphic forms.

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g., C$_{1-7}$alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol, imine/enamine, amide/imino alcohol, amidine/amidine, nitroso/oxime, thioketone/enethiol, N-nitroso/hyroxyazo, and nitro/aci-nitro.

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Unless otherwise specified, a reference to a particular compound includes all such isomeric forms, including (wholly or partially) racemic and other mixtures thereof. Methods for the preparation (e.g. asymmetric synthesis) and separation (e.g. fractional crystallisation and chromatographic means) of such isomeric forms are either known in the art or are readily obtained by adapting the methods taught herein, or known methods, in a known manner.

Salt

Unless otherwise specified, a reference to a particular compound also includes ionic, salt, solvate, and protected forms of thereof, for example, as discussed below, as well as its different polymorphic forms.

It may be convenient or desirable to prepare, purify, and/or handle a corresponding salt of the active compound, for example, a pharmaceutically-acceptable salt. Examples of pharmaceutically acceptable salts are discussed in Berge, et al., "Pharmaceutically Acceptable Salts", J. Pharm. Sci., 66, 1-19 (1977).

For example, if the compound is anionic, or has a functional group which may be anionic (e.g., —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{3+}$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g., —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous. Examples of suitable organic anions include, but are not limited to, those derived from the following organic acids: acetic, propionic, succinic, gycolic, stearic, palmitic, lactic, malic, pamoic, tartaric, citric, gluconic, ascorbic, maleic, hydroxymaleic, phenylacetic, glutamic, aspartic, benzoic, cinnamic, pyruvic, salicyclic, sulfanilic, 2-acetyoxybenzoic, fumaric, toluenesulfonic, methanesulfonic, ethanesulfonic, ethane disulfonic, oxalic, isethionic, valeric, and gluconic. Examples of suitable polymeric anions include, but are not limited to, those derived from the following polymeric acids: tannic acid, carboxymethyl cellulose.

Additional Salts

The compounds for use in the methods of the invention may be prepared, purified, handled, and/or used as a pharmaceutically acceptable salt as described below. These salts may be used in addition to, or as an alternative to, the salts described above.

Typically, a pharmaceutically acceptable salt may be readily prepared by using a desired acid or base as appropriate. The salt may precipitate from solution and be collected by filtration or may be recovered by evaporation of the solvent, for example, a compound for use in the invention may be dissolved in a suitable solvent, for example an alcohol such as methanol, and the acid may be added in the same solvent or another suitable solvent. The resulting acid addition salt may then be precipitated directly, or by addition of a less polar solvent such as diisopropyl ether or hexane, and isolated by filtration.

The skilled person will appreciate that where a compound for use in the invention contains more than one basic group bis salts or tris salts may also be formed and are salts suitable for use in the present disclosure.

Suitable addition salts are formed from inorganic or organic acids which form non-toxic salts and examples are lactobionate, mandelate (including (S)-(+)-mandelate, (R)-(−)-mandelate and (R,S)-mandelate), hydrochloride, hydrobromide, hydroiodide, sulfate, bisulfate, nitrate, phosphate, hydrogen phosphate, glutamate, acetate, trifluoroacetate, maleate, malate, fumarate, lactate, tartrate, citrate, formate, gluconate, succinate, ethyl succinate (4-ethoxy-4-oxo-butanoate), pyruvate, oxalate, oxaloacetate, saccharate, benzoate, glucolate, glucurinate, alkyl or aryl sulphonates (eg methanesulphonate, ethanesulphonate, benzenesulphonate or p-toluenesulphonate) and isethionate.

Pharmaceutically acceptable base salts include ammonium salts, alkali metal salts such as those of sodium and potassium, alkaline earth metal salts such as those of calcium and magnesium and salts with organic bases, including salts of primary, secondary and tertiary amines, such as isopropylamine, diethylamine, ethanolamine, trimethylamine, dicyclohexyl amine and N-methyl-D-glucamine.

Solvate

It may be convenient or desirable to prepare, purify, and/or handle a corresponding solvate of the active compound. The term "solvate" is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc.

Protected Forms

It may be convenient or desirable to prepare, purify, and/or handle the active compound in a chemically protected form. The term "chemically protected form," as used herein, pertains to a compound in which one or more reactive functional groups are protected from undesirable chemical reactions, that is, are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule.

See, for example, "Protective Groups in Organic Synthesis" (T. Green and P. Wuts; 3rd Edition; John Wiley and Sons, 1999).

For example, an amine group may be protected as described previously where Z is —$NH_2$ above. Additionally, an amine group may be protected as an amide or a urethane, for example, as: a methyl amide (—NHCO—$CH_3$); a benzyloxy amide (—NHCO—$OCH_2C_6H_5$, —NH-Cbz); as a t-butoxy amide (—NHCO—$OC(CH_3)_3$, —NH-Boc); a 2-biphenyl-2-propoxy amide (—NHCO—$OC(CH_3)_2C_6H_4C_6H_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulphonyl)ethyloxy amide (—NH-Psec); or, in suitable cases, as an N-oxide (>NO.).

For example, a carboxylic acid group may be protected as described previously in relation to the amino acid residues above. For example, a carboxylic acid group may be protected as an ester for example, as: a $C_{1-7}$ alkyl ester (e.g. a methyl ester; a t-butyl ester); a $C_{1-7}$haloalkyl ester (e.g. a $C_{1-7}$-trihaloalkyl ester); a tri$C_{1-7}$alkylsilyl-$C_{1-7}$alkyl ester; or a $C_{5-20}$aryl-$C_{1-7}$alkyl ester (e.g. a benzyl ester; a nitrobenzyl ester); or as an amide, for example, as a methyl amide.

For example, a hydroxyl group may be protected as an ether (—OR) or an ester (—OC(=O)R), for example, as: a t-butyl ether; a benzyl, benzhydryl (diphenylmethyl), or trityl (triphenylmethyl)ether; a trimethylsilyl or t-butyldimethylsilyl ether; or an acetyl ester (—OC(=O)$CH_3$, —OAc).

For example, an aldehyde or ketone group may be protected as an acetal or ketal, respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid.

Prodrugs

It may be convenient or desirable to prepare, purify, and/or handle the active compound in the form of a prodrug. The term "prodrug", as used herein, pertains to a compound which, when metabolised (e.g. in vivo), yields the desired active compound. Typically, the prodrug is inactive, or less active than the active compound, but may provide advantageous handling, administration, or metabolic properties.

For example, some prodrugs are esters of the active compound (e.g. a physiologically acceptable metabolically labile ester). During metabolism, the ester group (—C(=O)OR) is cleaved to yield the active drug. Such esters may be formed by esterification, for example, of any of the carboxylic acid groups (—COOH) in the parent compound, with, where appropriate, prior protection of any other reactive groups present in the parent compound, followed by deprotection if required. Examples of such metabolically labile esters include, but are not limited to, those wherein R is $C_{1-20}$alkyl (e.g. -Me, -Et); $C_{1-7}$aminoalkyl (e.g. aminoethyl; 2-(N,N-diethylamino)ethyl; 2-(4-morpholino)ethyl); and acyloxy-$C_{1-7}$alkyl (e.g. acyloxymethyl; acyloxyethyl; e.g. pivaloyloxymethyl; acetoxymethyl; 1-acetoxyethyl; 1-(1-methoxy-1-methyl)ethyl-carbonxyloxyethyl; 1-(benzoyloxy)ethyl; isopropoxy-carbonyloxymethyl; 1-isopropoxy-carbonyloxyethyl; cyclohexyl-carbonyloxymethyl; 1-cyclohexyl-carbonyloxyethyl; cyclohexyloxy-carbonyloxymethyl; 1-cyclohexyloxy-carbonyloxyethyl; (4-tetrahydropyranyloxy)carbonyloxymethyl; 1-(4-tetrahydropyranyloxy)carbonyloxyethyl; (4-tetrahydropyranyl)carbonyloxymethyl; and 1-(4-tetrahydropyranyl)carbonyloxyethyl).

Further suitable prodrug forms include phosphonate and glycolate salts. In particular, hydroxy groups (—OH), can be made into phosphonate prodrugs by reaction with chlorodibenzylphosphite, followed by hydrogenation, to form a phosphonate group —O—P(=O)(OH)$_2$. Such a group can be cleaved by phosphatase enzymes during metabolism to yield the active drug with the hydroxy group.

Also, some prodrugs are activated enzymatically to yield the active compound, or a compound which, upon further chemical reaction, yields the active compound. For example, the prodrug may be a sugar derivative or other glycoside conjugate, or may be an amino acid ester derivative.

Pharmaceutically Acceptable Salts

A "pharmaceutically acceptable salt", may be an acid addition salt in which the base retains the biological effectiveness and properties of the compound and which is physiologically acceptable. Such salts include those formed with inorganic acids such as hydrochloric acid, hydrobromic acid, sulphuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

Salts also include basic salts, such as an alkali or alkaline earth metal salt, e.g. a sodium, potassium, calcium or magnesium salt.

Additionally, or alternatively, salts may be formed with any one of N-methyl-D-glucamine, L-arginine, L-tysine, choline, and tris(hydroxymethyl)aminomethane.

DEFINITIONS

Alkyl: The term "alkyl" as used herein, pertains to a monovalent moiety obtained by removing a hydrogen atom from a carbon atom of a hydrocarbon compound having from 1 to 20 carbon atoms (unless otherwise specified) and which may be saturated or unsaturated (e.g. partially unsaturated, fully unsaturated).

Heteroalkyl: The term "Heteroalkyl" as used herein refers to an alkyl group having one or more carbon atoms replaced with a N, S, or O heteroatom.

In the context of alkyl groups, the prefixes (e.g. $C_{1-4}$, $C_{1-7}$, $C_{1-20}$, $C_{2-7}$, $C_{3-7}$, etc.) denote the number of carbon atoms, or range of number of carbon atoms. For example, the term "$C_{1-4}$alkyl", as used herein, pertains to an alkyl group having from 1 to 4 carbon atoms. Examples of groups of alkyl groups include $C_{1-4}$alkyl ("lower alkyl"), $C_{1-7}$alkyl, and $C_{1-20}$ alkyl. Note that the first prefix may vary according to other limitations; for example, for unsaturated alkyl groups, the first prefix must be at least 2; for cyclic alkyl groups, the first prefix must be at least 3; etc.

Examples of (unsubstituted) saturated alkyl groups include, but are not limited to, methyl ($C_1$), ethyl ($C_2$), propyl ($C_3$), butyl ($C_4$), pentyl ($C_5$), hexyl ($C_6$), heptyl ($C_7$), octyl ($C_8$), nonyl ($C_9$), decyl ($C_{10}$), undecyl ($C_{11}$), dodecyl ($C_{12}$), tridecyl ($C_{13}$), tetradecyl ($C_{1-4}$), pentadecyl ($C_{15}$), and eicodecyl ($C_{20}$).

Examples of (unsubstituted) saturated linear alkyl groups include, but are not limited to, methyl ($C_1$), ethyl ($C_2$), n-propyl ($C_3$), n-butyl ($C_4$), n-pentyl (amyl) ($C_5$), n-hexyl ($C_6$), and n-heptyl ($C_7$).

Examples of (unsubstituted) saturated branched alkyl groups include, but are not limited to, iso-propyl ($C_3$), iso-butyl ($C_4$), sec-butyl ($C_4$), tert-butyl ($C_4$), iso-pentyl ($C_5$), and neo-pentyl ($C_5$).

Cycloalkyl: The term "cycloalkyl", as used herein, pertains to an alkyl group which is also a cyclyl group; that is, a monovalent moiety obtained by removing a hydrogen atom from an alicyclic ring atom of a carbocyclic ring of a carbocyclic compound, which carbocyclic ring may be saturated or unsaturated (e.g. partially unsaturated, fully unsaturated), which moiety has from 3 to 20 carbon atoms (unless otherwise specified), including from 3 to 20 ring atoms. Preferably, each ring has from 3 to 7 ring atoms. Examples of groups of cycloalkyl groups include $C_{3-20}$ cycloalkyl, $C_{3-15}$ cycloalkyl, $C_{3-10}$ cycloalkyl, $C_{3-7}$ cycloalkyl.

Heterocyclyl: The term "heterocyclyl", as used herein, pertains to a monovalent moiety obtained by removing a hydrogen atom from a ring atom of a heterocyclic compound, which moiety has from 3 to 20 ring atoms (unless otherwise specified), of which from 1 to 10 are ring heteroatoms. Preferably, each ring has from 3 to 7 ring atoms, of which from 1 to 4 are ring heteroatoms.

In this context, the prefixes (e.g. $C_{3-20}$, $C_{3-7}$, $C_{5-6}$, etc.) denote the number of ring atoms, or range of number of ring atoms, whether carbon atoms or heteroatoms. For example, the term "$C_{5-6}$heterocyclyl", as used herein, pertains to a heterocyclyl group having 5 or 6 ring atoms. Examples of groups of heterocyclyl groups include $C_{3-20}$ heterocyclyl, $C_{5-20}$ heterocyclyl, $C_{3-15}$ heterocyclyl, $C_{5-15}$ heterocyclyl, $C_{3-12}$ heterocyclyl, $C_{5-12}$ heterocyclyl, $C_{3-10}$heterocyclyl, $C_{5-10}$ heterocyclyl, $C_{3-7}$ heterocyclyl, $C_{5-7}$ heterocyclyl, and $C_{5-6}$ heterocyclyl.

Examples of monocyclic heterocyclyl groups include, but are not limited to, those derived from:

$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);

$O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);

$S_1$: thiirane ($C_3$), thietane ($C_4$), thiolane (tetrahydrothiophene) ($C_5$), thiane (tetrahydrothiopyran) ($C_6$), thiepane ($C_7$);

$O_2$: dioxolane ($C_5$), dioxane ($C_6$), and dioxepane ($C_7$);

$O_3$: trioxane ($C_6$);

$N_2$: imidazolidine ($C_5$), pyrazolidine (diazolidine) ($C_5$), imidazoline ($C_5$), pyrazoline (dihydropyrazole) ($C_5$), piperazine ($C_6$);

$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);

$N_1S_1$: thiazoline ($C_5$), thiazolidine ($C_5$), thiomorpholine ($C_6$);

$N_2O_1$: oxadiazine ($C_6$);

$O_1S_1$: oxathiole ($C_5$) and oxathiane (thioxane) ($C_6$); and, $N_1O_1S_1$: oxathiazine ($C_6$).

Examples of substituted (non-aromatic) monocyclic heterocyclyl groups include those derived from saccharides, in cyclic form, for example, furanoses ($C_5$), such as arabinofuranose, lyxofuranose, ribofuranose, and xylofuranse, and pyranoses ($C_6$), such as allopyranose, altropyranose, glucopyranose, mannopyranose, gulopyranose, idopyranose, galactopyranose, and talopyranose.

$R^1$ and $R^2$ taken together with the nitrogen atom of the amide bond may represent a heterocyclyl group having at least one hydroxyl substituent. The heterocyclyl group may be a group selected from the $N_1$ examples provided above. The heterocyclyl group may contain one or more further heteroatoms. The heterocyclyl group may then be a group selected from the $N_2$, $N_1O_1$, $N_1S_1$, $N_2O$, and $N_1O_1S_1$ examples provided above.

Aryl: the term "aryl" as used herein, refers to a monovalent moiety obtained by removing a hydrogen atom from an aromatic ring atom of an aromatic compound, said compound having one ring, or two or more rings (e.g., fused).

Heteroaryl: The term "Heteroaryl" as used herein refers to an aryl group having one or more carbon atoms replaced with, but not limited to, a N, S, O heteroatom. In this case, a group may conveniently be referred to as a "$C_{5-20}$ heteroaryl" group, wherein "$C_{5-20}$" denotes ring atoms, whether carbon atoms or heteroatoms. Preferably, each ring has from 5 to 7 ring atoms, of which from 0 to 4 are ring heteroatoms.

Aralkyl: The term aralkyl as used herein, refers to an alkyl group, as defined above, substituted with one or more, preferably one, aryl groups as defined above.

Heteroaralkyl: The term 'heteroaralkyl' as used herein, refers to an alkyl group, as defined above, substituted with one or more, preferably one, aryl groups as defined above, where one or more carbon atoms in the alkyl and/or aryl group have been replaced with, but not limited to, a N, S, O heteroatom.

$C_{5-20}$ aryl: The term "$C_{5-20}$ aryl" as used herein, pertains to a monovalent moiety obtained by removing a hydrogen atom from an aromatic ring atom of a $C_{5-20}$ aromatic compound and having from 5 to 20 ring atoms, and wherein at least one of said ring(s) is an aromatic ring. Preferably, each ring has from 5 to 7 ring atoms.

Examples of $C_{5-20}$ aryl groups which do not have ring heteroatoms (i.e. $C_{5-20}$carboaryl groups) include, but are not limited to, those derived from benzene (i.e. phenyl) ($C_6$), naphthalene ($C_{10}$), anthracene ($C_{14}$), phenanthrene ($C_{14}$), and pyrene ($C_{16}$).

Examples of $C_{5-20}$ heteroaryl groups which comprise fused rings, include, but are not limited to, $C_9$ heteroaryl groups derived from benzofuran, isobenzofuran, benzothiophene, indole, isoindole; $C_{10}$heteroaryl groups derived from quinoline, isoquinoline, benzodiazine, pyridopyridine; $C_{1-4}$ heteroaryl groups derived from acridine and xanthene.

The above groups, whether alone or part of another substituent, may themselves optionally be substituted with one or more groups selected from themselves and the additional substituents listed below.

Halo: —F, —Cl, —Br, and —I.

Hydroxyl: —OH.

Ether: —OR, wherein R is an ether substituent, for example, a $C_{1-7}$ alkyl group (also referred to as a $C_{1-7}$ alkoxy group), a $C_{3-20}$ heterocyclyl group (also referred to as a $C_{3-20}$ heterocyclyloxy group), or a $C_{5-20}$ aryl group (also referred to as a $C_{5-20}$ aryloxy group), preferably a $C_{1-7}$ alkyl group.

Nitro: —$NO_2$.

Cyano (nitrile, carbonitrile): —CN.

Acyl (keto): —C(=O)R, wherein R is an acyl substituent, for example, H, a $C_{1-7}$alkyl group (also referred to as $C_{1-7}$ alkylacyl or $C_{1-7}$ alkanoyl), a $C_{3-20}$ heterocyclyl group (also referred to as $C_{3-20}$ heterocyclylacyl), or a $C_{5-20}$ aryl group (also referred to as $C_{5-20}$ arylacyl), preferably a $C_{1-7}$ alkyl group. Examples of acyl groups include, but are not limited to, —C(=O)$CH_3$ (acetyl), —C(=O)$CH_2CH_3$ (propionyl), —C(=O)C($CH_3$)$_3$ (butyryl), and —C(=O)Ph (benzoyl, phenone).

Carboxy (carboxylic acid): —COOH.

Ester (carboxylate, carboxylic acid ester, oxycarbonyl): —C(=O)OR, wherein R is an ester substituent, for example, a $C_{1-7}$alkyl group, a $C_{3-20}$heterocyclyl group, or a $C_{5-20}$aryl group, preferably a $C_{1-7}$ alkyl group. Examples of ester groups include, but are not limited to, —C(=O)O$CH_3$, —C(=O)O$CH_2CH_3$, —C(=O)OC($CH_3$)$_3$, and —C(=O)OPh.

Amido (carbamoyl, carbamyl, aminocarbonyl, carboxamide): —C(=O)$NR^1R^2$, wherein $R^1$ and $R^2$ are independently amino substituents, as defined for amino groups. Examples of amido groups include, but are not limited to, —C(=O)$NH_2$, —C(=O)$NHCH_3$, —C(=O)N($CH_3$)$_2$, —C(=O)$NHCH_2CH_3$, and —C(=O)N($CH_2CH_3$)$_2$, as well as amido groups in which $R^1$ and $R^2$, together with the nitrogen atom to which they are attached, form a heterocyclic structure as in, for example, piperidinocarbonyl, morpholinocarbonyl, thiomorpholinocarbonyl, and piperazinylcarbonyl.

Amino: —$NR^1R^2$, wherein $R^1$ and $R^2$ are independently amino substituents, for example, hydrogen, a $C_{1-7}$ alkyl group (also referred to as $C_{1-7}$ alkylamino or di-$C_{1-7}$alkylamino), a $C_{3-20}$ heterocyclyl group, or a $C_{5-20}$ aryl group, preferably H or a $C_{1-7}$ alkyl group, or, in the case of a "cyclic" amino group, $R^1$ and $R^2$, taken together with the nitrogen atom to which they are attached, form a heterocyclic ring having from 4 to 8 ring atoms. Examples of amino groups include, but are not limited to, —$NH_2$, —$NHCH_3$, —NHCH($CH_3$)$_2$, —N($CH_3$)$_2$, —N($CH_2CH_3$)$_2$, and —NHPh. Examples of cyclic amino groups include, but are not limited to, aziridinyl, azetidinyl, pyrrolidinyl, piperidino, piperazinyl, perhydrodiazepinyl, morpholino, and thiomorpholino. In particular, the cyclic amino groups may be substituted on their ring by any of the substituents defined here, for example carboxy, carboxylate and amido.

Acylamido (acylamino): —$NR^1$C(=O)$R^2$, wherein $R^1$ is an amide substituent, for example, hydrogen, a $C_{1-7}$ alkyl group, a $C_{3-20}$ heterocyclyl group, or a $C_{5-20}$aryl group, preferably H or a $C_{1-7}$ alkyl group, most preferably H, and $R^2$ is an acyl substituent, for example, a $C_{1-7}$alkyl group, a $C_{3-20}$heterocyclyl group, or a $C_{5-20}$aryl group, preferably a $C_{1-7}$alkyl group. Examples of acylamide groups include, but are not limited to, —NHC(=O)$CH_3$, —NHC(=O)$CH_2CH_3$, and —NHC(=O)Ph. $R^1$ and $R^2$ may together form a cyclic structure, as in, for example, succinimidyl, maleimidyl, and phthalimidyl:

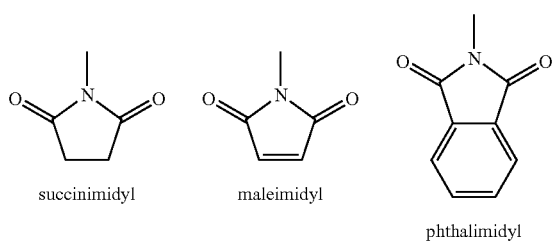

succinimidyl    maleimidyl    phthalimidyl

Ureido: —N($R^1$)CONR$^2R^3$ wherein $R^2$ and $R^3$ are independently amino substituents, as defined for amino groups, and R1 is a ureido substituent, for example, hydrogen, a $C_{1-7}$alkyl group, a $C_{3-20}$heterocyclyl group, or a $C_{5-20}$aryl group, preferably hydrogen or a $C_{1-7}$alkyl group. Examples of ureido groups include, but are not limited to, —NHCON$H_2$, —NHCONHMe, —NHCONHEt, —NHCONMe$_2$, —NHCONEt$_2$, —NMeCONH$_2$, —NMeCONHMe, —NMeCONHEt, —NMeCONMe$_2$, —NMeCONEt$_2$ and —NHCONHPh.

Acyloxy (reverse ester): —OC(=O)R, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group. Examples of acyloxy groups include, but are not limited to, —OC(=O)$CH_3$ (acetoxy), —OC(=O)$CH_2CH_3$, —OC(=O)C(CH$_3$)$_3$, —OC(=O)Ph, —OC(=O)C$_6$H$_4$F, and —OC(=O)CH$_2$Ph.

Thiol: —SH.

Thioether (sulfide): —SR, wherein R is a thioether substituent, for example, a C$_{1-7}$ alkyl group (also referred to as a C$_{1-7}$ alkylthio group), a C$_{3-20}$ heterocyclyl group, or a C$_{5-20}$ aryl group, preferably a C$_{1-7}$ alkyl group. Examples of C$_{1-7}$ alkylthio groups include, but are not limited to, —SCH$_3$ and —SCH$_2$CH$_3$.

Sulfoxide (sulfinyl): —S(=O)R, wherein R is a sulfoxide substituent, for example, a C$_{1-7}$alkyl group, a C$_{3-20}$ heterocyclyl group, or a C$_{5-20}$ aryl group, preferably a C$_{1-7}$alkyl group. Examples of sulfoxide groups include, but are not limited to, —S(=O)CH$_3$ and —S(=O)CH$_2$CH$_3$.

Sulfonyl (sulfone): —S(=O)$_2$R, wherein R is a sulfone substituent, for example, a C$_{1-7}$ alkyl group, a C$_{3-20}$ heterocyclyl group, or a C$_{5-20}$ aryl group, preferably a C$_{1-7}$alkyl group. Examples of sulfone groups include, but are not limited to, —S(=O)$_2$CH$_3$ (methanesulfonyl, mesyl), —S(=O)$_2$CF$_3$, —S(=O)$_2$CH$_2$CH$_3$, and 4-methylphenylsulfonyl (tosyl).

Thioamido (thiocarbamyl): —C(=S)NR$^1$R$^2$, wherein R$^1$ and R$^2$ are independently amino substituents, as defined for amino groups. Examples of amido groups include, but are not limited to, —C(=S)NH$_2$, —C(=S)NHCH$_3$, —C(=S)N(CH$_3$)$_2$, and —C(=S)NHCH$_2$CH$_3$.

Sulfonamino: —NR$^1$S(=O)$_2$R, wherein R$^1$ is an amino substituent, as defined for amino groups, and R is a sulfonamino substituent, for example, a C$_{1-7}$alkyl group, a C$_{3-20}$heterocyclyl group, or a C$_{5-20}$aryl group, preferably a C$_{1-7}$alkyl group. Examples of sulfonamino groups include, but are not limited to, —NHS(=O)$_2$CH$_3$, —NHS(=O)$_2$Ph and —N(CH$_3$)S(=O)$_2$C$_6$H$_5$.

As mentioned above, the groups that form the above listed substituent groups, e.g. alkyl, heterocyclyl and aryl, may themselves be substituted. Thus, the above definitions cover substituent groups which are substituted.

Use of Type-B Lantibiotic Compounds

The present invention provides the use of a type-B lantibiotic for the treatment or prophylaxis of a microbial infection in a subject. There is also provided the use of a type-B lantibiotic in the manufacture of a medicament for use in a method of treatment or prophylaxis of a subject.

The present invention provides type-B lantibiotics for the treatment or prophylaxis of a microbial infection of the lower intestine or colon in a subject.

The present invention also provides the use of a type-B lantibiotic in the preparation of a medicament for the treatment or prophylaxis of a bacterial infection of the lower intestine or colon in a subject.

It is preferred that the type-B lantibiotic is administered orally.

The most preferred type-B lantibiotics for use in the methods of the invention are actagardine compounds of formula (I) and mersacidin compounds of formula (II).

Infection and Disease

The present invention relates to the use of type-B lantibiotics, and pharmaceutical compositions thereof, in the treatment or prophylaxis of a microbial infection in a subject. The type-B lantibiotic compounds and compositions may be administered to a human or animal subject. The animal subject may be a mammal, or other vertebrate.

The term "microbial infection" refers to the invasion of the host animal by pathogenic microbes. This includes the excessive growth of microbes that are normally present in or on the body of an animal. More generally, a microbial infection can be any situation in which the presence of a microbial population(s) is damaging to a host animal. Thus, an animal is "suffering" from a microbial infection when excessive numbers of a microbial population are present in or on an animal's body, or when the presence of a microbial population(s) is damaging the cells or other tissue of an animal.

The present invention also relates to the treatment or prophylaxis of a *Clostridium difficile*, *Helicobacter pylori* or vancomycin-resistant enterococci (VRE) infection. Preferably the invention relates to a *Clostridium difficile* infection.

The present invention also relates to the treatment of an infection that has not been eradicated by treatment with another active compound, preferably a compound that is not a type-B lantibiotic. The other active compound may be vancomycin.

Where the type-B lantibiotic compound for use in the present invention is administered to a subject having an infection that has not been eradicated by treatment with another active compound, the type-B lantibiotic may be administered within 1 day, 1 week or 1 month, 2 months or 3 months of the last administration of the other active compound. Preferably the other active compound is vancomycin.

The type-B lantibiotic compounds and compositions may also be used for systemic treatment of bacteraemia (including catheter related bacteraemia), pneumonia, skin and skin structure infections (including surgical site infections), endocarditis and osteomyelitis. These and other such treatments may be directed against causative agents such as staphylococci, streptococci, enterococci. The compounds of the invention or compositions thereof may also be used for topical treatment of skin infections including acne i.e. *Propionibacterium acnes*. The compounds and compositions thereof may also be used in the treatment of eye infections, such as conjunctivitis.

The compounds may also be used in the treatment or prevention of infection of the skin in wounds or burns. In addition, the compounds and compositions described herein for use in the invention may be used in prophylactic methods. This may be practiced on subjects at risk of infection (e.g. patients entering a hospital) or on health professionals or other carers at risk of being carriers of such infections.

Most preferably, the compounds and compositions may be used for treatment of gut super-infection, such as that caused by *Clostridium difficile* including multiply-resistant *C. difficile* (pseudomembranous colitis). The compound or composition may be administered orally. Gut infections associated with *Helicobacter pylori* may also be treated.

The present invention also provides a method for treating CDAD. Complete relief of symptoms of CDAD by the end of the treatment may be defined as resolution to less than 3 bowel movements per day (whether formed or unformed), and no associated fever, elevated WBC (white blood cell) count, or abdominal pain.

Pharmaceutical Compositions

The type-B lantibiotic-based compounds of the present invention may be formulated together with one or more other pharmaceutically acceptable ingredients well known to those skilled in the art, including, but not limited to, pharmaceutically acceptable carriers, adjuvants, excipients, diluents, fillers, buffers, preservatives, anti-oxidants, lubricants, stabilizers, solubilisers, surfactants (e.g., wetting agents), masking agents, colouring agents, flavouring agents, and sweetening agents. The formulation may further comprise other active agents, for example, other therapeutic or prophylactic agents. Thus, the present invention further provides pharmaceutical compositions, as defined above, and methods of making a pharmaceutical composition comprising admixing at least one active compound, as defined above, together with one or more other pharmaceutically acceptable ingredients well known to those skilled in the art, e.g., carriers, adjuvants, excipients, etc. If formulated as discrete units (e.g., tablets, etc.), each unit contains a predetermined amount (dosage) of the active compound.

The term "pharmaceutically acceptable" as used herein pertains to compounds, ingredients, materials, compositions, dosage forms, etc., which are, within the scope of sound medical judgement, suitable for use in contact with the tissues of the subject in question (e.g., human) without excessive toxicity, irritation, allergic response, or other problem or complication, commensurate with a reasonable benefit/risk ratio. Each carrier, adjuvant, excipient, etc. must also be "acceptable" in the sense of being compatible with the other ingredients of the formulation.

Compositions may be formulated for any suitable route and means of administration. Pharmaceutically acceptable carriers or diluents include those used in formulations suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

For solid compositions, conventional non-toxic solid carriers include, for example, pharmaceutical grades of mannitol, lactose, cellulose, cellulose derivatives, starch, magnesium stearate, sodium saccharin, talcum, glucose, sucrose, magnesium carbonate, and the like may be used. The active compound as defined above may be formulated as suppositories using, for example, polyalkylene glycols, acetylated triglycerides and the like, as the carrier. Liquid pharmaceutically administrable compositions can, for example, be prepared by dissolving, dispersing, etc, an active compound as defined above and optional pharmaceutical adjuvants in a carrier, such as, for example, water, saline aqueous dextrose, glycerol, ethanol, and the like, to thereby form a solution or suspension. If desired, the pharmaceutical composition to be administered may also contain minor amounts of non-toxic auxiliary substances such as wetting or emulsifying agents, pH buffering agents and the like, for example, sodium acetate, sorbitan monolaurate, triethanolamine sodium acetate, sorbitan monolaurate, triethanolamine oleate, etc. Actual methods of preparing such dosage forms are known, or will be apparent, to those skilled in this art; for example, see *"Remington: The Science and Practice of Pharmacy"*, 20th Edition, 2000, pub. Lippincott, Williams & Wilkins. The composition or formulation to be administered will, in any event, contain a quantity of the active compound(s) in an amount effective to alleviate the symptoms of the subject being treated.

Dosage forms or compositions containing active ingredient in the range of 0.25 to 95% with the balance made up from non-toxic carrier may be prepared.

For oral administration, the preferred method of administration, a pharmaceutically acceptable non-toxic composition is formed by the incorporation of any of the normally employed excipients, such as, for example, pharmaceutical grades of mannitol, lactose, cellulose, cellulose derivatives, sodium crosscarmellose, starch, magnesium stearate, sodium saccharin, talcum, glucose, sucrose, magnesium, carbonate, and the like. Such compositions take the form of solutions, suspensions, tablets, pills, capsules, powders, sustained release formulations and the like. Such compositions may contain 1%-95% active ingredient, more preferably 2-50%, most preferably 5-8%.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, triethanolamine sodium acetate, etc.

For topical applications, the pharmaceutically acceptable compositions may be formulated in a suitable ointment or gel containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

The percentage of active compound contained in such parental or topical compositions is highly dependent on the specific nature thereof, as well as the activity of the compound and the needs of the subject. However, percentages of active ingredient of 0.1% to 10% w/w employable, and will be higher if the composition is a solid which will be subsequently diluted to the above percentages. Preferably, the composition will comprise 0.2-2% w/w of the active agent in solution.

Other compositions for use in the invention include delayed release formulations, in which the type-B lantibiotic is formulated in a manner which allows specific delivery to the small and large intestine, and more preferably specifically to the colon. This can be achieved by using delayed release formulations which are taken orally.

There are numerous teachings in the art of means to provide delayed release formulations of compounds such that the active ingredient is released primarily in the colon. Generally, such means provide for protection of the active ingredient from the environment of the stomach and intestines by means of one or more coatings. For example, EP-0572942, the disclosure of which is incorporated herein by reference, describes a delayed release composition comprising a core of active ingredient optionally combined with one or more excipients, coated with an intermediate layer which delays release of the ingredient independently of pH, and an outer layer which dissolved in a pH dependent manner.

The outer layer may be a polymer such as cellulose acetophthalate, cellulose acetate terephthalate, cellulose acetate trimellitate, hydroxypropyl-methyl cellulose phthalate, polyvinyl alcohol phthalate, polyacrylate or a polymethacrylate. The coating will have little or no solubility at a pH lower than 5, but will dissolve at a more neutral or alkaline pH, for example of 7.5 or above. This coating protects the active ingredient during its passage through the stomach and intestines.

The intermediate layer will be a material such as a hydrophobic gelling polymer such as methylcellulose, carboxymethylcellulose, hydroxypropylmethylcellulose, polyvinyl alcohols, polysaccharides and the like.

An alternative approach is described in WO 91/07949, which also uses two protecting layers. In this reference, the intermediate layer is an amorphous amylose, such as glassy or rubbery amylose. This layer is broken down by the action of enzymes of the microflora which are found in the colon. An outer layer of a film forming cellulose material or acrylic polymer material is then added to provide protection to the amylose layer. This outer layer dissolves in a pH-independent manner. The amylose is preferably glassy amylose with a glass transition temperature, Tg, of no less than 17° C., preferably no less than 30° C., and a molecular weight of at least 20,000, e.g. at least 100,000 daltons.

The film forming cellulose may be, for example, sodium carboxymethyl cellulose, sodiumcarboxymethyl 1-hydroxyethyl cellulose, 2-hydroxycellulose, 2-hydroxypropyl cellulose, methyl cellulose, and the like, preferably with a molecular weight range of from 42,0000 to 280,000 daltons. Acrylic polymer materials include acrylate and methacrylate polymers and copolymers thereof, preferably in the molecular weight range of from 15,000 to 250,000 daltons.

According to WO 91/07949, the disclosure of which is incorporated herein by reference, the amylose coating may be from 5 to 50 μM in thickness around a core of active ingredient of, for example a 1 mm sphere, and the outer coating may also be of a similar size range. Coatings comprising a mixture of the amylose and film forming material are also described.

Delayed release compositions of the invention, including those as described above, will allow the substantial bulk of the active ingredient (for example at least 50% of each unit dosage form) released in the body of a subject to be released in the colon.

For example, a delayed release composition will show less than 20%, preferably less than 10% release of active ingredient after 3 hours in 0.1N HCl at 20° C., but more than 50%, preferably more than 75% release of active ingredient within 24 hours when at a pH of 7.0 or above (e.g. 7.5) and/or exposed to anaerobic microbial digestion by faecal microflora (for example using digestive conditions described in Example 4(d) of WO 91/07949).

It will be appreciated that the composition of a pharmaceutical composition may become altered as it passes through the gastrointestinal tract. For example, a flavouring compound may be shed from the composition in accordance with a planned delivery mechanism.

Further teaching regarding suitable carriers, adjuvants, excipients, etc. can be found in standard pharmaceutical texts, for example, "*Remington: The Science and Practice of Pharmacy*", 20th Edition, 2000, pub. Lippincott, Williams & Wilkins; and *Handbook of Pharmaceutical Excipients*, 2nd edition, 1994.

Administration and Delivery to Site of Action

The compounds described herein can be administered enterally (orally), parenterally (intramuscularly or intravenously), rectally, nasally, vaginally or locally (topically). They can be administered in the form of solutions, powders (tablets, capsules including microcapsules), ointments (creams or gel), or suppositories. Possible auxiliaries for formulations of this type are the pharmaceutically customary liquid or solid fillers and extenders, solvents, emulsifiers, lubricants, flavour corrigents, colorants and/or buffer substances.

The compounds and compositions described herein are preferably administered orally. Briefly, a compound or pharmaceutical composition administered orally may pass from the oral cavity to the esophagus and then to the stomach. From the stomach, the compound or pharmaceutical composition may be taken on to the small intestine and then the large intestine, which includes the colon. The type-B lantibiotic for use in the methods of the invention may be stable in each of these gastrointestinal regions. The type-B lantibiotics for use in the invention may be used to treat an infection of the colon, particularly a *C. difficile* infection. The colon is the division of the large intestine extending from the cecum to the rectum.

The type-B lantibiotics described herein, and derivatives and variants thereof, may have improved stability to degradative enzymes, such as those found in the gastrointestinal tract, compared to antibiotics such as nisin. Particularly, the compounds described herein may have improved stability to intestinal fluid compared to antibiotics such as nisin. The compounds described herein may have improved stability to pancreatin.

Reference to prancreatin is reference to a mixture of one or more digestive enzymes produced by the exocrine cells of the pancreas. Pancreatin typically contains one or more of a protease, a lipase and an amylase. Pancreatin may comprise one or more enzymes from the group consisting of tyrpsin (formed as tyrpsinogen in the pancreas) and chymotrypsin (formed as chymotrypsinogen in the pancreas).

Where methods of the invention refer to the use of pancreatin in an in vitro method, the pancreatin may be sourced from a human subject or an animal subject, for example a hog (porcine pancreatin).

The invention therefore provides a method of treatment or prophylaxis of a microbial infection in a subject comprising administering to the subject a type-B lantibiotic, wherein the type-B lantibiotic is subsequently exposed to a pancreatin-containing environment, such as an intestinal fluid environment. The intestinal fluid environment may comprise other degrative enzymes in addition to the pancreatin enzymes.

The type-B lantibiotics for use in the invention may be stable in a gastric fluid environment. Stability may be defined in relation to the fraction of a type-B lantibiotic that is recovered from a simulated gastric fluid after exposure for at least 15 mins, at least 30 mins, at least 60 mins, at least 120 mins, or at least 180 mins. A stable type-B lantibiotic may be recovered from the fluid in at least 80 mol %, at least 90 mol %, at least 95 mol %, or at least 99 mol % of the amount of type-B lantibiotic that was originally treated with the simulated fluid.

Additionally or alternatively, stability may be defined in relation to the activity of a type-B lantibiotic against a reference microorganism before and after exposure to a gastric fluid. The microorganism may be *M. Leutus*. A stable type-B lantibiotic may be recovered from the fluid may retain at least 80%, at least 90%, at least 95%, or at least 99% activity compared to type-B lantibiotic prior to exposure. The gastric fluid may be a simulated gastric fluid or a gastrointestinal extract.

The compounds for use in the invention may be stable in a intestinal fluid environment. Stability may be defined in relation to the fraction of type-B lantibiotic that is recovered from a simulated intestinal fluid after exposure for at least 15 mins, at least 30 mins, at least 60 mins, at least 120 mins, or at least 180 mins. A stable type-B lantibiotic may be recovered in at least 80%, at least 90% at least 95%, or at least 99 mol % of the amount of type-B lantibiotic that was originally treated with the simulated fluid.

Additionally or alternatively, stability may be defined in relation to the activity of a type-B lantibiotic against a reference microorganism before and after exposure to a intestinal fluid. The microorganism may be *M. Leutus*. A stable type-B lantibiotic may be recovered from the fluid may retain at least 80%, at least 90%, at least 95%, or at least 99% activity compared to the type-B lantibiotic prior to exposure. The gastric fluid may be a simulated intestinal fluid or a gastrointestinal extract.

The type-B lantibiotic compounds for use in the invention are preferably not significantly absorbed or metabolised in the gastrointestinal tract of the subject to whom a compound has been orally administered. Particularly, the compound may not be absorbed or metabolised in the stomach or small intestine of the subject.

The stability of the type-B lantibiotics described herein to enzymatic degradation by intestinal fluid is highly advantageous. As discussed above, compounds such as nisin, that are not stable in intestinal fluid, require extensive formulation to ensure that the compound is not degraded during the delivery to the site of action, and is not degraded at the site of action.

Timing

The time effective to treat a bacterial infection ranges from one day to one year. In certain instances, treatment can be for several weeks or months, or even extended over the lifetime of the individual patient, if necessary. For example, the duration of treatment may be at least 5 days, at least 10 days, at least 30 days, at least 45 days, at least 90 days, or at least 180 days. Ultimately, it is most desirable to extend the treatment for such a time that a non-multiplying form of the bacteria is no longer detectable.

The administration of a compound or composition may be repeated as necessary. The compound or composition may be administered one, two, three, four or five times a day. Alternatively, the administration may be repeated daily, or every other day, or can be repeated every third day, or once weekly. Within a treatment regime, the timing of the frequency of the administration may be altered during the duration of treatment if required.

Where a dose of the compound or composition is administered intravenously, it may be administered over a period of 4 to 24 hours, 8 to 24 hours, or 15 to 24 hours. A dose may be administered by intravenous infusion over a 2, 4, 5, 6, 7, 8, 9, 10, 12, 14, 20, 24, 48, or 72 hour period.

A factor in selecting an appropriate dose and scheduling is the result obtained, as indicated above. For example, relatively higher doses may be needed initially for the treatment of the bacterial; infection. A subsequent dose may be higher than an earlier dose. To obtain the most efficacious results, the compound is generally administered as close to the first sign, diagnosis, appearance, or occurrence of the infection as possible or during remissions of the infection.

Dosage

An effective amount of a compound or composition is administered to a subject in the treatment or prophylaxis of that subject.

By "effective" amount is meant the amount of active ingredient required to treat or prevent an infection or a disease associated with an infection. The effective amount of compound used to practice the invention for therapeutic or prophylactic treatment of conditions caused by or contributed to by a microbial infection varies depending upon the manner of administration, the age, body weight, and general health of the subject. Ultimately, the attending physician will decide the appropriate amount and dosage regimen. Such amount is referred to as an "effective" amount.

The effective amount of the compound to be administered will ultimately be at the discretion of the physician, taking into account the severity of the disease in a particular subject (e.g. a human patient or animal model) and the overall condition of the subject. Suitable dose ranges will typically be in the range of from 0.1-1,000 mg/kg, e.g. from 0.2 to 100 mg/kg, or from 1 to 50 mg/kg, or from 5 to 25 mg/kg, with doses typically being administered as the physician finds appropriate. They are expediently administered in dose units which contain at least the efficacious daily amount of the compounds according to the invention, e.g. 30-3,000, preferably 50-1,000 mg.

Suitably, the effective amount of the compound to be administered is from around 100 to around 2,000 mg per patient per day.

Toxicity and therapeutic efficacy of such compounds can be determined by standard pharmaceutical procedures in biological assays or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred for use in the invention. While compounds that exhibit toxic side effects may be used, care should be taken to design a delivery system that targets such compounds to the site of affected tissue in order to minimize potential damage to uninfected cells and, thereby, reduce side effects.

The data obtained from the assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from biological assays and the animal studies. Such information can be used to more accurately determine useful doses in humans.

It will be appreciated that the dose may be adjusted depending on the type of formulation that is used to deliver the compound to the site of action, the degree of infection and severity of the disease, as well as the transit time of the product through the intestine, which will be affected by whether, and the degree to which, the subject has diarrhoea.

Patient Group

The present invention also provides a method for the treatment or prophylaxis of a microbial infection of the lower intestine or colon in a subject, the method comprising administering to the subject a type-B lantibiotic, wherein the subject is in a select patient group. The patient group may include a subject having a microbial infection that is resistant to a particular active agent. Preferably, the microbial infection is resistant to treatment with vancomycin. The subject may have a microbial infection that is resistant to treatment with an active agent that is not a type-B lantibiotic.

Suitably, the subject is a subject who has received the active agent at least 1 hour, 2 hours, 24 hours, 2 days, 3 days, 1 week, 2 weeks, 1 month, 2 months or 3 months prior to the treatment with the type-B lantibiotic. Suitably, the subject received the active agent at least 1 month or 2 months prior to the treatment with the type-B lantibiotic.

Co-Administration

Compositions for use in the invention may also comprise a second active agent, including a different type-B lantibiotic compound, a different antimicrobial agent, or another agent intended to treat a second symptom or cause of a condition to be treated.

The use of a second active agent may allow a type-B lantibiotic to be used more effectively, where the second active agent is administered with the type-B lantibiotic.

Suitably, the composition does not include an additional active agent that is active against the organisms that dominate the gut flora under normal healthy conditions, most notably *Bifidobacterium* spp and *Bacteroides* spp.

In one embodiment the second active agent is tolevamar (GT160-246). Tolevamar binds *C. difficile* cytotoxins A/B and is associated with restoration of components of the anaerobic intestinal microflora during treatment of *C. difficile*-associated diarrhea (see Louie et al, *Proceedings of 14th European Congress of Clinical Microbiology and Infectious Diseases, Prague Congress Centre, Prague, Czech Republic, May* 1-4, 2004).

Various antibacterial agents can be used in conjunction with the compounds for use in the present invention. These include quinolones, tetracyclines, glycopeptides, aminoglycosides, β-lactams, rifamycins, coumermycins, macrolides, ketolides, azalides, and chloramphenicol. In particular embodiments an antibiotic of the above classes can be, for example, one of the following:

β-Lactam Antibiotics: imipenem, meropenem, biapenem, cefaclor, cefadroxil, cefamandole, cefatrizine, cefazedone, cefazolin, cefixime, cefinenoxime, cefodizime, cefonicid, cefoperazone, ceforanide, cefotaxime, cefotiam, cefpimizole, cefpiramide, cefpodoxime, cefsulodin, ceftazidime, cefteram, ceftezole, ceftibuten, ceftizoxime, ceftriaxone, cefuroxime, cefuzonam, cephaacetrile, cephalexin, cephaloglycin, cephaloridine, cephalothin, cephapirin, cephradine, cefinetazole, cefoxitin, cefotetan, azthreonam, carumonam, flomoxef, moxalactam, amidinocillin, amoxicillin, ampicillin, azlocillin, carbenicillin, benzylpenicillin, carfecillin, cloxacillin, dicloxacillin, methicillin, mezlocillin, nafcillin, oxacillin, penicillin G, piperacillin, sulbenicillin, temocillin, ticarcillin, cefditoren, SC004, KY-020, cefdinir, ceftibuten, FK-312, S-1090, CP-0467, BK-218, FK-037, DQ-2556, FK-518, cefozopran, ME1228, KP-736, CP-6232, Ro 09-1227, OPC-20000 and LY206763.

Macrolides: azithromycin, clarithromycin, erythromycin, oleandomycin, rokitamycin, rosaramicin, roxithromycin, and troleandomycin.

Ketolides: ABT-773, Telithromycin (HMR 3647), HMR3562, HMR3004, HMR3787, ABT-773, CP-654,743, C2-fluoro ketolide, A1957730, and TE802.

Quinolones: amifloxacin, cinoxacin, ciprofloxacin, enoxacin, fleroxacin, flumequine, lomefloxacin, nalidixic acid, norfloxacin, ofloxacin, levofloxacin, oxolinic acid, pefloxacin, rosoxacin, temafloxacin, tosufloxacin, sparfloxacin, clinafloxacin, PD131628, PD138312, PD140248, Q-35, AM-1155, NM394, T-3761, rufloxacin, OPC-17116, DU-6859a, and DV-7751a.

Tetracyclines: chlortetracycline, demeclocycline, doxycycline, lymecycline, methacycline, minocycline, oxytetracycline, and tetracycline.

Glycopeptides: vancomycin and derivatives thereof.

Aminoglycosides: amikacin, arbekacin, butirosin, dibekacin, fortimicins, gentamicin, kanamycin, meomycin, netilmicin, ribostamycin, sisomicin, spectinomycin, streptomycin, tobramycin, clindamycin, and lincomycin.

Rifamycins: rifamycin SV, rifamycin O, rifabutin, rifampicin, rifampin, and rifalizil.

Instead of a second antibacterial agent, the composition may comprise a second agent intended to treat a further symptom or cause of a condition to be treated by the mersacidin variant. For example, the composition may comprise an analgesic agent, e.g. a non-steroidal anti-inflammatory compound. Particularly where the composition is for the treatment of skin infections, the composition may comprise a dermatological agent such as a steroid, for treatment of inflammation of the skin. Other agents which may be useful in dermatological applications include retinoids, bactericidal agents such as benzoyl peroxide and anti-fungal agents.

In these aspects of the invention, the compound to be combined with a second active agent may be any one of the compounds described for use in the invention above, including acatgardine, deoxy-actagardine B N-[2-ethanolamine], mersacidin and mersacidin F3W.

The second active agent may be administered to a subject simultaneously, separately or sequentially.

By "simultaneous" administration, it is meant that the type-B lantibiotic and the second active agent are administered to a subject in a single dose by the same route of administration.

By "separate" administration, it is meant that type-B lantibiotic and the second active agent are administered to a subject by two different routes of administration which occur at the same time. This may occur for example where one agent is administered by infusion and the other is given orally during the course of the infusion.

By "sequential" it is meant that the two agents are administered at different points in time, provided that the activity of the first administered agent is present and ongoing in the subject at the time the second agent is administered. For example, the type-B lantibiotic may be administered first, such that the microbial infection of the subject is reduced at the point in time when the second active agent is administered. Alternatively, the second active agent may be administered first.

Generally, a sequential dose will occur such that the second of the two agents is administered within 48 hours, preferably within 24 hours, such as within 12, 6, 4, 2 or 1 hour(s) of the first agent.

The agents will be formulated appropriately for their desired route of administration. The agent or pharmaceutical composition comprising the agent may be administered to a subject by any convenient route of administration, whether systemically/peripherally or topically (i.e., at the site of desired action).

Additional Uses of Type-B Lantibiotic Compounds

The present invention provides the use of the compounds or compositions described herein for the manufacture of a medicament for the treatment of *C. difficile* infection and/or bacterial overgrowth syndrome.

In one aspect, the disclosure provides use of a compound of formula (I), (Ia), (Ib), (Ic) or another compound described herein in therapy, for example, for treatment of microbial infections such as *C. difficile* infection, in particular diarrhoea associated therewith, particularly by oral delivery of a compound of formula (I), (Ia), (Ib), (Ic).

The present invention provides a method of treatment comprising administering a therapeutically effective amount of a compound or composition as defined described herein to a patient for treatment of a *C. difficile* infection and/or bacterial overgrowth syndrome.

In one embodiment, the method is a method for treatment of a *C. difficile* infection.

In one embodiment, the method is a method for treatment of a *C. difficile* infection in the colon and/or lower intestines.

In one embodiment, the method is a method for treatment of bacterial overgrowth in the small intestines.

In one aspect there is provided use of a compound of formula (I), (Ia), (Ib), (Ic) or another compound described for the treatment of cecitis (in an animal subject).

In one aspect the compound of formula (I), (Ia), (Ib), (Ic) or another compound described herein is employed for controlling bacterial overgrowth syndrome. Overgrowth syndrome (BOS) occurs when the normally low bacterial colonization in the upper GI tract and/or lower intestines significantly increases.

The compounds of the present disclosure may be particularly useful for long term treatment.

As described above the compounds of the present disclosure may be employed in the treatment of humans and/or animals.

In one aspect there is provided a compound of formula (I), (Ia), (Ib), (Ic) or another compound described herein for the manufacture of a medicament for the for treatment of microbial infections such as *C. difficile* infection, in particular diarrhoea associated therewith and/or overgrowth syndrome.

In one aspect there is provided a method of treatment comprising the step of administering a therapeutically effective amount of a compound of formula (I), (Ia), (Ib), (Ic) or another compound described herein or a pharmaceutical composition containing the same to a patient (human or animal) in need thereof, for example for the treatment of an infection/illness or disease as described herein.

In one embodiment, the compound for use in the methods described above is a compound of formula (Ia), (Ib), or (Ic).

Methods for Preparing Compounds of the Invention
Experimental Synthesis of Type-B Lantibiotic Compounds A series of type-B lantibiotic compounds were prepared as described in detail below. Parent lantibiotics such as actagardine were obtained in accordance with the methods described for these compounds above.

Actagardine

The following actagardine compounds were prepared, in which the parent lantibiotic, and the groups X1, X2, Z and X were as follows:

| Compound | Lantibiotic | X1 | X2 | Y | Z | X |
|---|---|---|---|---|---|---|
| VI | Actagardine | Val | Ile | —S(O)— | —NH$_2$ | *—NH—CH$_2$CH$_2$—OH |
| VII | Deoxy-actagardine B | Leu | Val | —S— | —NH$_2$ | *—NH—CH$_2$CH$_2$—OH |
| VIII | Deoxy-actagardine B | Leu | Val | —S— | —NH$_2$ | *—NH—(CH$_2$)$_4$—OH |
| VI | Actagardine | Val | Ile | —S(O)— | —NH$_2$ | *—NH—CH$_2$CH$_2$—OH |
| IX | Deoxy-actagardine B | Leu | Val | —S— | —NH$_2$ | *—NH—CH$_2$—CH(OH)—CH$_2$OH |
| X | Deoxy-actagardine B | Leu | Val | —S— | —NH$_2$ | *—NH—CH(CH$_2$OH)$_2$ |
| XI | Deoxy-actagardine B | Leu | Val | —S— | —NH$_2$ | *—NH—C(CH$_2$OH)$_3$ |
| XII | Deoxy-actagardine B | Leu | Val | —S— | —NH$_2$ | *—NH—CH$_2$—CH(OH)—CH$_3$ |
| XIII | Deoxy-actagardine B | Leu | Val | —S— | —NH$_2$ | *—NH—(CH$_2$)$_3$—OH |
| XXIII | Deoxy-actagardine B | Leu | Val | —S— | —NH$_2$ | *—NH—CH$_2$CH$_2$—N(CH$_2$CH$_2$OH)$_2$ |

-continued

| Compound | Lantibiotic | X1 | X2 | Y | Z | X |
|---|---|---|---|---|---|---|
| XXVIII | Deoxy-actagardine B | Leu | Val | —S— | —NH₂ | 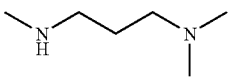 |
| XXIX | Deoxy-actagardine B | Leu | Val | —S— | —NH₂ | 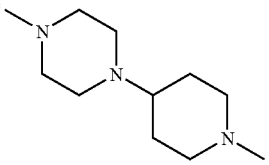 |
| XXX | Deoxy-actagardine B | Leu | Val | —S— | —NH₂ | 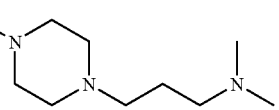 |
| XXXI | Deoxy-actagardine B | Leu | Val | —S— | D-Ala | —OH |
| XXXII | Deoxy-actagardine B | Leu | Val | —S— | L-Ile | —OH |
| XXXIII | Deoxy-actagardine B | Leu | Val | —S— | L-Val | —OH |
| V | Deoxy-actagardine B | Leu | Val | —S— | L-Phe | —OH |
| VI | Actagardine | Val | Ile | —S(O)— | —NH₂ | 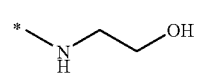 |
| XXXIV | Deoxy-actagardine B | Leu | Val | —S— | L-Lys | —OH |
| XXXV | Deoxy-actagardine B | Leu | Val | —S— | L-Tryp | —OH |

The following compounds were also made, in which the parent lantibiotic and the groups X1, X2, Z, and R¹ and R² were as follows:

The asterisk indicates the point where the nitrogen atom is linked to alanine residue at position 19 via an amide bond. By reference to the group Z being an amino acid residue, it will be

| Compound | Lantibiotic | X1 | X2 | Y | Z | R¹ | R² |
|---|---|---|---|---|---|---|---|
| L | Deoxy-actagardine B | Leu | Val | —S— | —NH₂ | 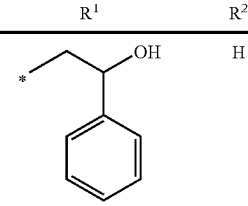 | H |
| LI | Deoxy-actagardine B | Leu | Val | —S— | —NH₂ | 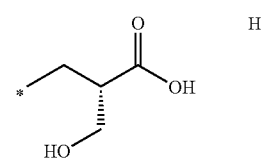 | H |
| LII | Deoxy-actagardine B | Leu | Val | —S— | —NH₂ | 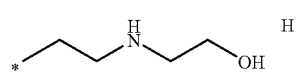 | H |
| LIII | Deoxy-actagardine B | Leu | Val | —S— | —NH₂ | 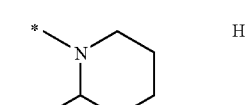 | H | understood that this moiety represents an amino acid, conventionally referred to in the art as Xaa(0), linked to the amino acid at position 1 via an amide bond.

Preparation of Compounds VI-XIII, XXIII and L to LIII
General Procedure 1

To a solution of lantibiotic (e.g. actagardine, actagardine B, or deoxy-actagardine B) (200 mg, 108 nmol), an appropriate aminoalcohol (330 nmol) and diisopropylethylamine (410 nmol) in dry dimethylformamide (2 ml) was added portionwise a solution of benzotriazole-1-yl-oxy-trispyrrolidinophosphonium hexafluorophosphate (PYBOP™) (125 mg, 258 nmol) in dry dimethylformamide (1.5 ml). The mixture was analysed by HPLC to follow the progress of the reaction, adding further aliquots of the PYBOP™ solution until all the starting material had been consumed. HPLC analysis at this stage also showed variable amounts (5-20%) of the diamide. After completion of the reaction, the mixture was diluted with 30% acetonitrile in 20 mM Kpi aqueous phosphate buffer, pH7 (10 ml) and the monoamide was purified by preparative HPLC using the conditions described in Table 1 The appropriate fractions were concentrated to 25% of their original volume and desalted by loading on to a preconditioned C18 Bond Elut column (500 mg) which was subsequently washed by sequential elution with two column volumes of 30, 40, 70 and 90% aqueous methanol. Evaporation of the appropriate fractions gave the desired products as white solids. Samples were analysed by LC-MS using the conditions described below.

Compound VI: Actagardine
N-[2-ethanolamine]monocarboxamide

Was obtained from coupling of deoxyactagardine B and ethanolamine according to General Procedure 1. Yield 11 mg, 53% yield. [M+2H $2^+$] calculated 966.5, found 966.1.

Compound VII: Deoxy-Actagardine B
N-[2-ethanolamine]monocarboxamide

Was obtained from coupling of deoxyactagardine B and ethanolamine according to General Procedure 1. Yield 18 mg, 85% yield. [M+2H $2^+$] calculated 979.0, found 980.2.

Compound VII: Deoxy-Actagardine B
N-[4-butanolamine]monocarboxamide

Was obtained from coupling of deoxyactagardine B and butanolamine according to General Procedure 1. Yield 9 mg, 43% yield. [M+2H $2^+$] calculated 972.50, found 979.9.2.

Compound IX: Deoxy-Actagardine B
(3-amino-1,2-propanediol) monocarboxamide

Was obtained from coupling of deoxyactagardine B and 3-amino-1,2-propanediol according to General Procedure 1. Yield 18 mg, 87% yield. [M+2H $2^+$] calculated 973.5.0, found 973.9.

Compound X: Deoxy-Actagardine B
(2-amino-1,3-propanol) monocarboxamide

Was obtained from coupling of deoxyactagardine B and 2-amino-1,3-propanol according to General Procedure 1. Yield 20 mg, 96% yield. [M+2H $2^+$] calculated 973.5, found 973.9.

Compound XI: Deoxy-Actagardine B
[tris(hydroxymethyl)methylamine]monocarboxamide Was obtained from coupling of deoxyactagardine B and tris(hydroxymethyl)methylamine according to General Procedure 1. Yield 13 mg, 69% yield. [M+2H $2^+$] calculated 988.5, found 988.6.

Compound XII: Deoxy-Actagardine B
(1-amino-2-propanol) monocarboxamide

Was obtained from coupling of deoxyactagardine B and 1-amino-2-propanol according to General Procedure 1. Yield 16 mg, 78% yield. [M+2H $2^+$] calculated 965.5, found 965.6.

Compound XII: Deoxy-Actagardine B
(1-amino-3-propanol) monocarboxamide

Was obtained from coupling of deoxyactagardine B and 1-amino-3-propanol according to General Procedure 1. Yield 19 mg, 87% yield. [M+2H $2^+$] calculated 965.5, found 965.3.

Compound XX: Deoxy-Actagardine B
N-[2-hydroxy-2-phenylethylamine]monocarboxamide Was obtained from coupling of deoxyactagardine B and N-[2-hydroxy-2-phenylethylamine] according to General Procedure 1. [M+2H $2^+$] calculated 995.5, found 995.8.

Compound XXI: Deoxy-actagardine B (L-serine methyl ester) monocarboxamide

Was obtained from coupling of deoxyactagardine B and L-serine methyl ester according to General Procedure 1. [M+2H $2^+$] calculated 987.5, found 986.9.

Compound XXII: Deoxyactagardine B
(N-(2-hydroxyethyl)ethylenediamine)
monocarboxamide Was obtained from coupling of deoxyactagardine B and N-(2-hydroxyethyl)ethylenediamine according to General Procedure 1. [M+2H $2^+$] calculated 980, found 979.8.

Compound XXIII: Deoxy-actagardine B
(2-hydroxypiperazine) monocarboxamide

Was obtained from coupling of deoxyactagardine B and 2-hydroxypiperazine according to General Procedure 1. [M+2H $2^+$] calculated 978.5, found 977.7.

Preparation of Compounds XIV-XXIII, and LX-LXVI

General Procedure 2 exemplified for (L)-Tryptophanyl-(0)-deoxyactagardine B N-(9-Fluorenylmethoxycarbonyl)-tryptophan-O-pentafluorophenyl ester (80 mg, 135 nmol) was added to a solution of 1-hydroxybezotriazole hydrate (18 mg, 135 nm) in dry dimethylformamide (1 ml). The mixture was then added to a solution of deoxyactagardine B (50 mg, 27 nmol) in dry dimethylformamide (0.5 ml). The mixture was left at room temperature for 15 min, after which all the starting material had been consumed. Water (0.05 ml) and piperidine (0.1 ml) were added and the mixture was left at room temperature for 1 h. The reaction mixture was diluted into 30% aqueous methanol and the resulting white suspension loaded on to a 1 g C18 solid phase extraction cartridge. Material was eluted with fractions of 40%, 50%, 60% and 70% aqueous methanol. The 60% fraction was evaporated to dryness, leaving a tan solid. Yield=35 mg (63%). [M+2H 2$^+$] calculated 1030.0, found 1030.1.

Compound XV:
(L)-Tryptophanyl-(0)-deoxyactagardine B
(ethanolamine) monocarboxamide Was obtained from coupling of (L)-Tryptophanyl-(0)-deoxyactagardine B (50 mg) and ethanolamine according to General Procedure 1. Yield 23 mg, 45% yield. [M+2H 2$^+$] calculated 1051.5, found 1051.8.

(L)-Phenylalanyl-(0)-deoxyactagardine B

Was obtained from the coupling of deoxyactagardine B and N-(9-Fluorenylmethoxycarbonyl)-phenylalanine-O-pentafluorophenyl ester according to General Procedure 2. Yield 65% yield. [M+2H$^{2+}$] calculated 1010.5, found 1011.0.

Compound XIV:
(L)-Phenylalanyl-(0)-deoxyactagardine B
(ethanolamine) monocarboxamide Was obtained from coupling of (L)-Phenylalanyl-(0)-deoxyactagardine B (50 mg) and ethanolamine according to General Procedure 1. Yield 23 mg, 45% yield. [M+2H$^{2+}$] calculated 1032.0, found 1032.2.

Preparation of Compounds XXIV-XXX

These compounds were prepared as described previously by the inventors.

Thus, to a solution of deoxy-actagardine B (20 mg, 11 nmol), the appropriate amine (11 nmol) and diisopropylethylamine (7.2 µl, 70 nmol) in dry dimethylformamide (0.8 ml) were added 200 µl of a solution of benzotriazole-1-yl-oxy-tris-pyrrolidino-phosphonium hexafluorophosphate (PyBop) (70 mg, 134 nmol) in dry dimethylformamide (1.0 ml). The mixture was analysed by HPLC to follow the progress of the reaction, adding further aliquots of the PyBop solution until all the starting material had been consumed. HPLC analysis at this stage also showed variable amounts (5-20%) of the diamide. After completion of the reaction, the mixture was diluted with 30% acetonitrile in 20 mM Kpi aqueous phosphate buffer, pH7 (10 ml) and the monoamide was purified by preparative HPLC using the conditions described in Table 4. The appropriate fractions were concentrated to 25% of their original volume and desalted by loading on to a preconditioned C18 Bond Elut column (500 mg) which was subsequently washed by sequential elution with two column volumes of 30, 40, 70 and 90% aqueous methanol. Evaporation of the appropriate fractions gave the desired products as white solids.

Compound XXVIII: Deoxy-Actagardine B
N-[3-dimethylaminopropyl]monocarboxamide

Was obtained from coupling of deoxyactagardine B and 3-(dimethylamino)propylamine according to the method above. Yield 18 mg, 85% yield. [M+2H 2$^+$] calculated 979.0, found 980.2.

Compound XXIX: Deoxy-Actagardine B N-[1-(1-methyl-4-piperidinyl)piperazine]monocarboxamide Was obtained from the coupling of deoxyactagardine B and 4-(piperidino)piperazine according to the method above. Yield 8 mg, 37% yield. [M+2H 2$^+$] calculated 1019.5, found 1020.0; [M+3H 3$^+$] calculated 680.0, found 680.0.

Compound XXX: Deoxy-Actagardine B [1-(3-dimethylaminopropyl)piperazine]monocarboxamide Was obtained from the coupling of deoxy-actagardine B and 1-(3-dimethylaminopropyl)piperazine according to the method above. Yield 10 mg, 46% yield. [M+2H 2$^+$] calculated 1013.5, found 1014.0.

Preparation of Compounds V and XXXI-XXXV

These compounds were prepared as described previously by the inventors.

Thus, a solution of the appropriate Fmoc protected amino acid (34 nmol) in dry dimethylformamide (0.4 ml) was treated with a solution of benzotriazole-1-yl-oxy-tris-pyrrolidino-phosphonium hexafluorophosphate (PyBop) (11.4 mg, 22 nmol) and diisopropylethylamine (11 µl, 68 nmol) in dry dimethylformamide (0.4 ml). The mixture was then added to a solution of deoxy-Actagardine B (2 mg, 1 mmol) in dry dimethylformamide (0.5 ml) The mixture was left at room temperature for 1 h, after which time analytical HPLC (30-65% acetonitrile in 20 mM Kpi aqueous phosphate buffer, pH7) showed complete conversion of the starting material. The reaction mixture was diluted with 40% aqueous methanol (20 ml) and the mixture was passed through a C18 Bond Elute column (500 mg) that had been preconditioned by washing with two column volumes of 100% methanol followed by two column volumes of water. The column was eluted sequentially with two column volumes of 40, 50, 60, 70, 80, 90 and 100% aqueous methanol. The fractions were analysed by HPLC and the fractions containing the Fmoc-protected coupling product were evaporated to dryness. The residue was taken up in dimethylformamide (1 ml) and piperidine (50 µl) was added to remove the Fmoc protecting group. Progress of the reaction was monitored by HPLC and after complete consumption of the starting material the solution was diluted into 30% aqueous methanol (20 ml). The mixture was then eluted through a C18 Bond Elut cartridge (500 mg) as previously described and the product obtained after evaporation of the appropriate fractions was further purified by preparative HPLC using the conditions described below. The appropriate fractions were concentrated to 25% of their original volume and desalted by loading on to a preconditioned C18 Bond Elut column (500 mg) which was subsequently washed by sequential elution with two column volumes of 30, 40, 70 and 90% aqueous methanol. Evaporation of the appropriate fractions gave the desired products as white solids.

Compound XXXI: D-Ala(0)deoxy-actagardine B

Was prepared according to the method above from deoxy-actagardine B and Fmoc-D-alanine in 74% yield. [M+2H 2$^+$] calculated 972.5, found 973.0

Compound XXXI: L-Ile(0)deoxy-actagardine B

Was prepared according to the method above from deoxy-actagardine B and Fmoc-L-isoleucine in 27% yield. [M+2H 2$^+$] calculated 993.5, found 993.8

Compound XXXIII: L-Val(0)deoxyactagardine B
Was prepared according to the method above from deoxy-actagardine B and Fmoc-L-valine in 55% yield. [M+2H 2$^+$] calculated 986.5, found 985.9.

Compound V: L-Phe(0)deoxyactagardine B

Was prepared according to the method above from deoxy-actagardine B and Fmoc-L-phenylalanine in 22% yield. [M+2H 2$^+$] calculated 1010.5, found 1010.9.

Compound XXXIV: L-Lys(0)deoxyactagardine B

Was prepared according to the method above from deoxy-actagardine B and Bis(Fmoc)-L-lysine in 45% yield. [M+2H 2$^+$] calculated 1001.0, found 1001.6

Compound XXXV: L-Trp(0)deoxyactagardine B

Was prepared according to the method above from deoxy-actagardine B and Fmoc-L-tryptophan in 55% yield. [M+2H 2$^+$] calculated 1030.0, found 1029.9.

High Performance Liquid Chromatography

HPLC analyses were performed using a Hewlett Packard 1050 series HPLC system with the parameters as described below:

| Column: | Zorbax SB-C18, 4.6 × 150 mm, 5µ |  |  |  |  |
|---|---|---|---|---|---|
| Mobile Phase A: | 30% Acetonitrile in 20 mM potassium phosphate buffer pH 7.0 |  |  |  |  |
| Mobile Phase B: | 65% Acetonitrile in 20 mM potassium phosphate buffer pH 7.0 |  |  |  |  |
| Flow rate: | 1 ml/min |  |  |  |  |
| Gradient: | Time 0 min | 100% | A | 0% | B |
|  | Time 10 min | 0% | A | 100% | B |
|  | Time 11 min | 0% | A | 100% | B |
|  | Time 11.2 min | 100% | A | 0% | B |
| Cycle time 15 min |  |  |  |  |  |
| Injection volume: | 10 µl |  |  |  |  |
| Detection: | 210 nm |  |  |  |  |

High Performance Liquid Chromatography-Mass Spectrometry (HPLC-MS)

HPLC-MS analyses were performed on a Hewlett Packard™ 1050 series HPLC system linked to a Micromass™ Platform LC (operated with MassLynx™ version 3.5 software) with the parameters contained in Table 3.

TABLE 3

Preparative HPLC conditions for the separation of lantibiotic (e.g. actagardine, actagardine B, or deoxy-actagardine B) and a derivatised product.

| Column | Capitol HPLC Ltd C18 - BDS - HL5 - 26052 15 cm × 20 mm |
|---|---|
| Solvent A | 30% Acetonitrile in 20 mM Potassium Phosphate pH 7.0 |
| Solvent B | 65% Acetonitrile in 20 mM Potassium Phosphate pH 7.0 |
| Detection | 268 nm |
| Flow Rate | 10 ml/min |
| Time (T) = 0 min | 100% A |
| T = 1 min | 100% A |
| T = 19 min | 25% B |
| T = 20 min | 100% B |
| T = 25 min | 100% B |
| T = 26 min | 100% A |
| T = 30 min | 100% A |
| Collection | Start 8 min; End 20 min; 1 minute fractions |

The experimental basis of the present invention, including its best mode, will now be further described in detail, by way of example only, with reference to the accompanying drawings.

Mersacidin

Mersacdidn and F3W mersacdin were prepared according to the methods previously described by the inventors. See WO 2007/036706 for details.

Example 1

Activity of Type B Lantibiotics Against *C. difficile*

Compounds I to VII were screened against twelve clinical isolates of *Clostridium difficile*. The tests were performed in Wilkins-Chalgren Anaerobe Agar under anaerobic conditions, and the MIC (minimum inhibitory concentration—defined as the lowest concentration of substance that completely inhibits visible growth of bacteria) was determined for each compound.

As shown in Table 4, all the *Clostridium difficile* strains were inhibited by compounds I to VII at concentrations of 4 g/ml or less. Table 2 also lists the MIC values for vancomycin. Compounds I to VII have similar in vitro potency to vancomycin. The data show that the general sensitivity of *Clostridium difficile* make this bacterium a viable target organism for therapy using type-B lantibiotics.

TABLE 4

Activity of type-B lantibiotics against *C. difficile*

| | Minimal Inhibitory Concentration (MIC) in µg/ml | | | | | | | | |
|---|---|---|---|---|---|---|---|---|---|
| *C. difficile* Strain | I | II | III | IV | V | VI | VII | Vanc. | Metro. |
| 37779 | 2 | 4 | 4 | 2 | 1 | 1 | 2 | 2 | 0.125 |
| 19126 | 2 | 4 | 4 | 2 | 2 | 2 | 2 | 1 | 0.25 |
| P24 | 2 | 4 | 2 | 2 | n/d | 2 | 2 | 0.5 | 0.25 |
| B32 | 2 | 4 | 2 | 2 | 2 | 2 | 2 | 1 | 0.125 |
| E101 | 4 | 4 | 2 | 2 | 2 | 2 | 2 | 0.5 | 0.125 |
| E16 | 4 | 4 | 2 | 2 | 2 | 2 | 2 | 0.5 | 8 |
| E4 | 2 | 2 | 2 | 2 | 2 | 2 | 2 | 1 | 0.25 |
| 027C | 4 | 1 | 2 | 2 | 2 | 2 | 1 | 1 | 0.25 |
| 27SM | 4 | 2 | 2 | 2 | 2 | 1 | 1 | 1 | 0.125 |
| P49 | 4 | 2 | 2 | 2 | 2 | 2 | 1 | 1 | 0.125 |
| P59 | 4 | 2 | 2 | 2 | 2 | 2 | 2 | 1 | 0.25 |
| P62 | 4 | 2 | 2 | 2 | 1 | 1 | 0.5 | 1 | 0.25 |

Compounds
I Mersacidin
II Actagardine
III Deoxyactagardine B
IV F3W Mersacidin
V Phe(0)deoxyactagardine B
VI Actagardine N-[2-ethanolamine] monocarboxamide
VII Deoxy-actagardine B N-[2-ethanolamine] monocarboxamide
Vanc. Vancomycin
Metro. Metronidazole In addition, compounds L to LIII were screened against twelve four isolates of *Clostridium difficile*. The MIC data is given in Table 4A below.

TABLE 4A

Activity of Type-B lantibiotics Against *C. difficile*

| *Clostridium difficile* | L | LI | LII | LIII |
|---|---|---|---|---|
| *C. difficile* 19126 | 2 | 4 | 2 | 4 |
| *C. difficile* 37779 | 2 | 4 | 2 | 4 |

TABLE 4A-continued

Activity of Type-B lantibiotics Against *C. difficile*

| *Clostridium difficile* | L | LI | LII | LIII |
|---|---|---|---|---|
| *C. difficile* 027C | 2 | 2 | 2 | 4 |
| *C. difficile* 630 | 2 | 4 | 2 | 2 |

Example 2

Activity of Type-B Lantibiotics Against Other Gut Organisms

The activities of several type-B lantibiotic derivatives (Compounds II, IV and VI) against a number of species commonly occurring as part of the gut flora were measured and compared with vancomycin (Table 5). The compounds were found to have low potency against *Bifidobacterium* spp and *Bacteroides* spp and it can therefore fairly be assumed that they would have no significant effect on the gut flora at therapeutic doses levels, unlike vancomycin.

TABLE 5

Activity of type-B lantibiotics against organisms common in the intestinal flora.

| | Minimal Inhibitory Concentration (MIC) µg/ml | | | |
|---|---|---|---|---|
| Organism | III | IV | VI | Vancomycin |
| *E. coli* DC2 (membrane more susceptible) | >64 | >64 | >64 | >64 |
| *E. coli* ATCC 25922 | >64 | >64 | >64 | >64 |
| *E. faecium* (VSE) ATCC 19579 | 64 | 32 | 16 | 0.5 |
| *E. faecalis* (VSE) ATCC 29212 | 8 | 32 | 4 | 4 |
| *E. faecium* (VRE) (clinical isolate) | >64 | 32 | 64 | >64 |
| *E. faecalis* (VRE) (clinical isolate) | 4 | 16 | 4 | >64 |
| *Bifidobacterium adolescentis* NCTC 11814 | 16 | 32 | 32 | 1 |
| *Bifidobacterium longum* NCTC 11818 | 16 | 16 | 32 | 1-2 |
| *Bacteroides fragilis* NCTC 9343 | >64 | 32 | >64 | 32 |
| *Bacteroides thetaiotaomicron* NCTC 10582 | >64 | 16 | >64 | 64 |

Example 3

Stability of Type-B Lantibiotics in Simulated Gastric and Intestinal Fluids

Type-A lantibitotics have linear (uncyclised) sections in the amino sequence. Such linear sections are vulnerable to enzymolysis and consequently the type-A lantibiotics are rapidly digested.

The type-B lantibitotics described herein may have increased stability to enzymatic degradation compared to type-A lantibiotics such as nisin.

Nisin and mersacidin were tested for their susceptibility towards enzymatic digestion in the stomach and intestine. The SGF and SIF were based on the standard USP solutions for simulated gastric and simulated intestinal fluids and their activity confirmed against Bovine Serum Albumin (Hilger et al, 2001). The compounds were incubated in SGF or SIF at 37° C. and their concentrations quantified by analytical HPLC (UV detection at 210 nm). The potential degradation of each compound was also monitored qualitatively by measuring in vitro antibacterial activity against *Micrococcus luteus*.

FIG. 1(a) shows the concentration of nisin and mersacidin as a function of time in Simulated Gastric Fluid. FIG. 1(b) shows the concentration of compounds VI and VII as a function of time in Simulated Gastric Fluid. None of the compounds showed appreciable degradation in SGF.

Figure 2:
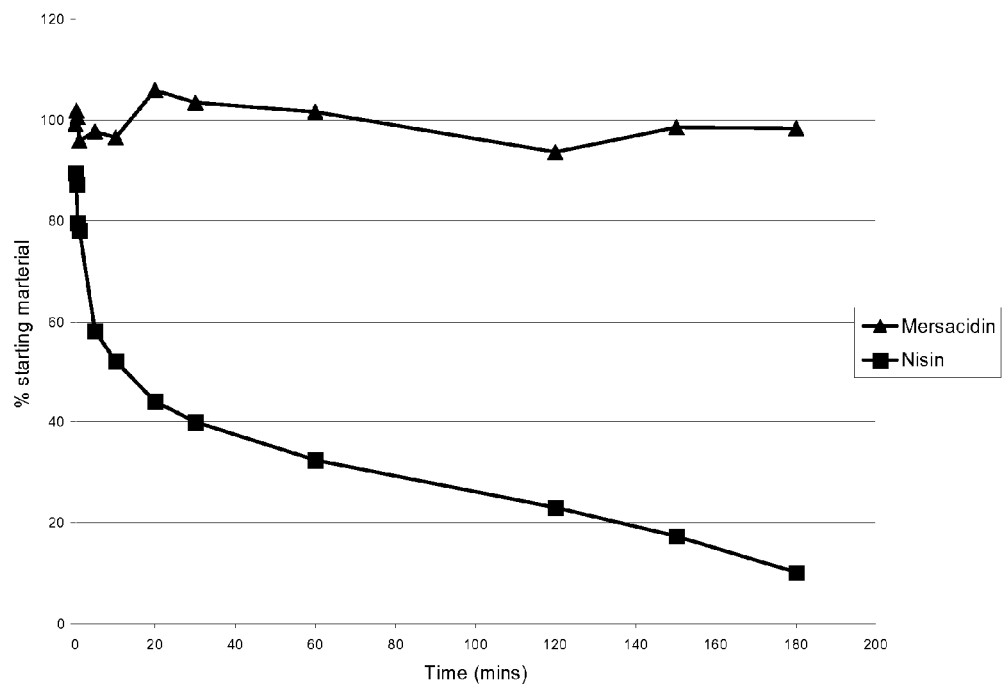
FIG. 2 (*a*) shows the stability of the lantibiotics mersacidin and nisin in simulated intestinal fluid (SIF).
Figure 2:
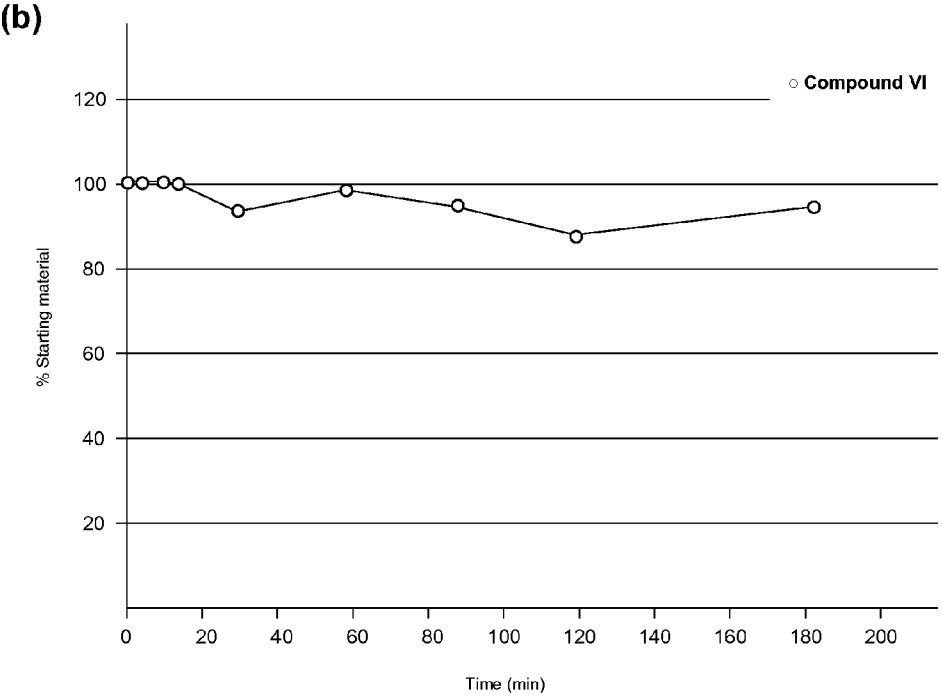

In contrast, FIG. 2(a) shows that nisin was rapidly degraded in SIF with a half-life of approximately 15 minutes. The rapid degradation of nisin in this medium supports the observation that the clinical utility of nisin for the treatment of colonic infections is very limited unless the compound can be protected from degradative enzymes by means of careful formulation. FIG. 2(a) also shows that mersacidin is essentially stable in SIF and that for these compounds metabolic instability is unlikely to be a factor affecting their efficacy in treating colonic *C. difficile* infections. Actagardine and deoxyactagardine B were found similarly stable in SGF and SIF. The concentration data obtained by HPLC was corroborated by in vitro activity against *M. luteus*, which remained unaltered for mersacidin and deoxyactagardine B during the course of the experiment.

FIG. 2(b) shows that compound VI is also essentially stable in SIF.

Example 4

Sporicidal Activity of Type-B Lantibiotics

Once an individual is susceptible to infection after treatment with broad-spectrum antibiotics, *C. difficile* colonisation occurs by the oral-faecal route. Environmental contamination by *C. difficile* is very common in hospitals where epidemic strains of *C. difficile* are transmitted extensively; health care workers may transfer the bacteria between patients on their hands or equipment. The heat-resistant spores formed by *C. difficile* are able to persist in the environment for months or even years. Infection is caused by the oral ingestion of spores that are able to travel through the acid environment of the stomach unaffected, converting to vegetative forms once in the colon.

An agent capable of killing, or preventing the successful germination of *C. difficile* spores would therefore be of considerable interest. To determine the effects of type B lantibiotics on *C. difficile* spores, suspensions of spores were exposed to antibiotics (100 g/ml) and aliquots were taken at appropriate time points. The spores in each aliquot were filtered off and plated out on to Brazier's agar. Viable counts were recorded and are summarised in Table 6.

TABLE 6

Activity of antibiotics at 100 g/ml against *C. difficile* spores.

| | Time (h) | | | |
|---|---|---|---|---|
| Compound | 0 | 4 | 8 | 24 |
| Vancomycin | 177 | 188 | 183 | 135 |
| Metronidazole | 177 | 154 | 144 | 120 |
| Mersacidin | 177 | 0 | 0 | 0 |
| Deoxyactagardine B | 177 | 53 | 21 | 0 |

The results in Table 6 show that the current clinical agents used in the treatment of *C. difficile* infections, vancomycin and metronidazole, have no significant effect on spore viability. In contrast, at 100 g/ml the type B lantibiotics mersacidin and deoxyactagardine B inactivate or prevent *C. difficile* spores from germinating to form new vegetative cells. The activity of these lantibiotics against spores would be of considerable value in the prevention of repeated *C. difficile* infections.

Example 5

Figure 3:
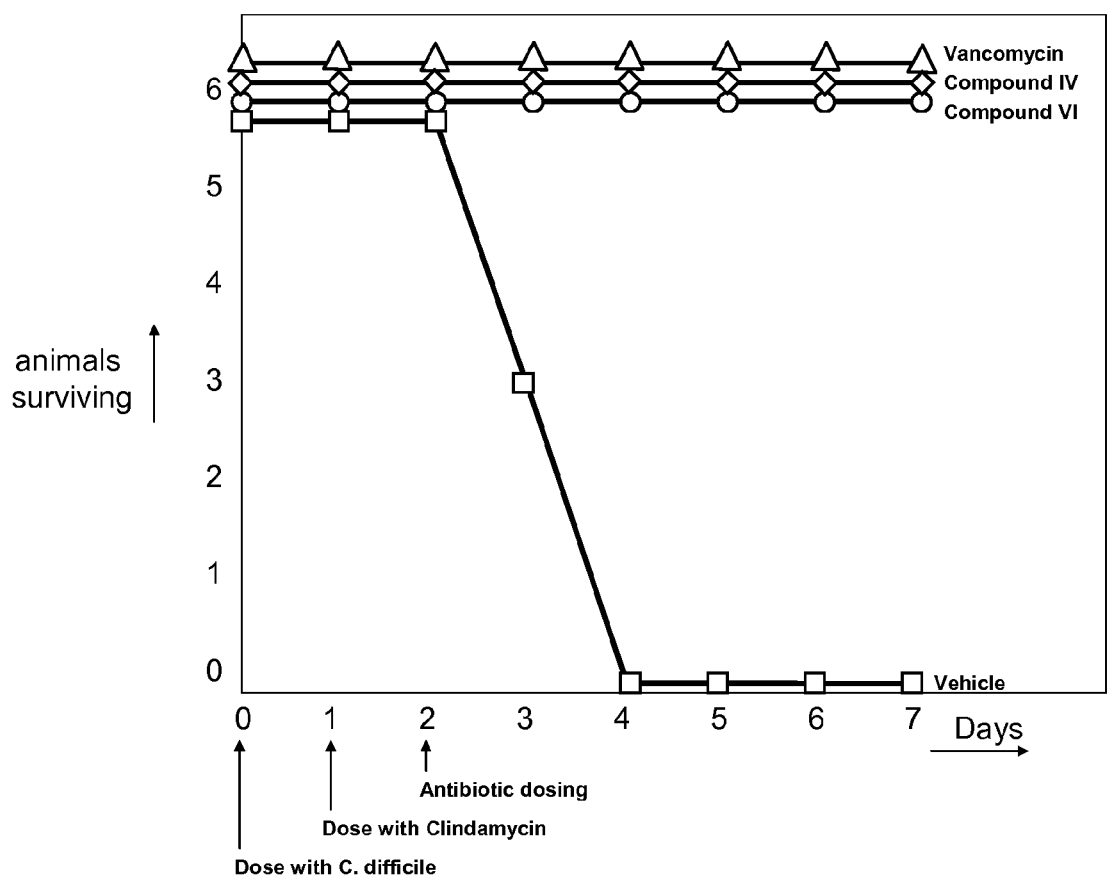
FIG. 3 shows the in vivo efficacy of vancomycin, compound IV and compound VI in the hamster model of *C. difficile*-associated cecitis.

In Vivo Efficacy of Type-B Antibiotics in the Hamster Model of *C. difficile* Associated Cecitis The in vivo efficacy of two type B Lantibiotics in the treatment of *C. difficile* infections was evaluated in the standard animal model for CDAD: clindamycin-induced cecitis in hamster (FIG. 3). Four groups of six animals were dosed orally with approximately $10^7$ cells of *C. difficile* strain VPI 10463 and 24 hours later with a subcutaneous dose of 10 mg/kg clindamycin phosphate. After a further 24 h, the four groups were then treated either with vehicle, vancomycin, compound IV or compound VI three times daily at 50 mg/kg/day.

The procedure as described induced a *C. difficile* infection in the test animals, from which all animals treated with vehicle only died within 3 days. In contrast, all animals treated with vancomycin, compound IV or compound VI survived for the duration of the entire 5-day dosing period, demonstrating the protective effects of these compounds.

Example 6

In Vivo Stability of Type-B Antibiotics

For the purpose of treating intestinal *Clostridium difficle* infections with an orally administered, non-absorbed antibiotic it is of great importance that the compound is resistant to digestive enzymes and metabolism by the intestinal flora such that high concentrations can be achieved at the site of infection, typically the colon. Whilst in vitro models of gastric and intestinal fluids can provide an early indication of GI stability of a compound, in vivo experiments may provide more direct evidence that the compound reached the site of infection. In the Male Sprague-Dawley rats were dosed with compound VII at 100 mg/kg via the oral route. Faeces and urine were collected over a 48 h period in two batches (24 h and 48 h post dose). Blood samples were taken at various time points for the first 24 h.

Analysis of the various biological samples for the parent compound showed that at least 35% of compound VII was excreted in faeces unchanged, demonstrating that high colonic concentrations of the type-B lantibiotic can be achieved. No material was recovered from plasma or urine after oral dosing, a result consistent with low GI absorption.

Example 7

Figure 4:
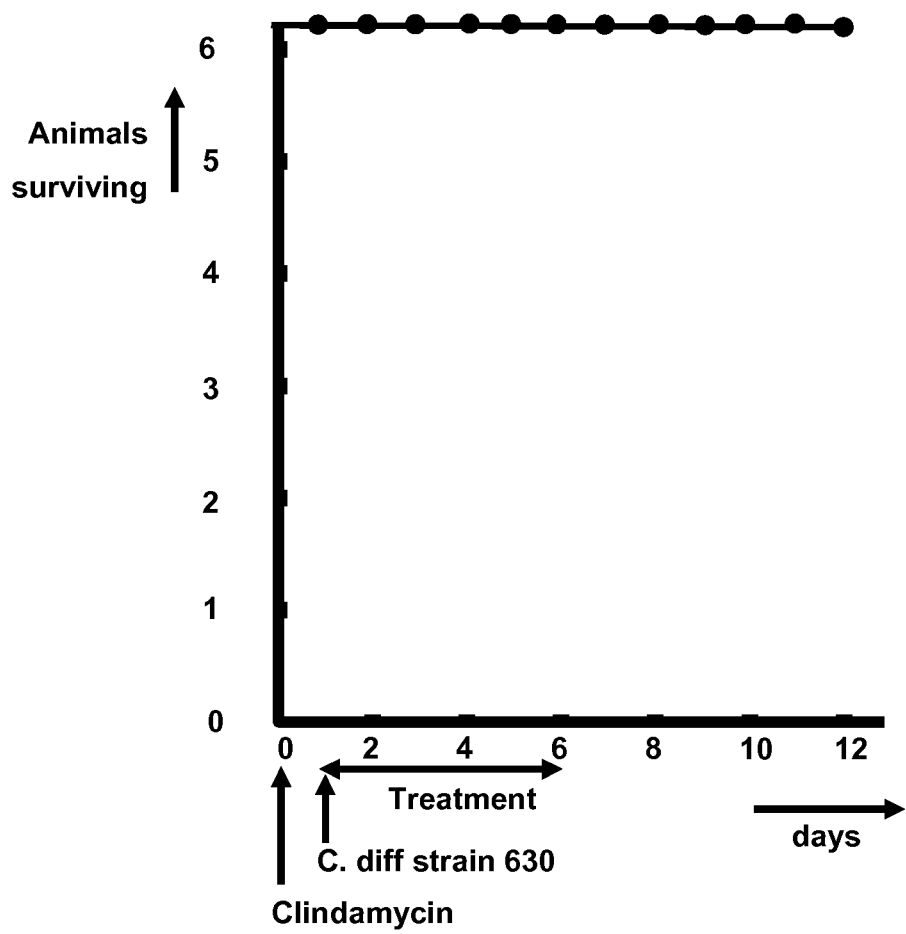
FIG. 4 shows the in vivo efficacy of compound VII in the hamster model of *C. difficile*-associated cecitis.

In Vivo Efficacy of Type-B Antibiotics in the Hamster Model of *C. difficile* Associated Cecitis The in vivo efficacy of compound VII in the treatment of *C. difficile* infections was evaluated in the clindamycin-induced cecitis model in hamster (FIG. 4). Groups of 6 animals were given a subcutaneous dose of 10 mg/kg clindamycin phosphate. 24 hours later, the animals received oral inocula of ~$10^4$ spores of *C. difficile* 630, prepared by heating overnight BHI culture fluids to 56° C. for 10 min and recovering spores by centrifugation and re-suspension of the pellet in an equal volume of PBS. After a further 24 h, the four groups were then treated either with vehicle, vancomycin, or compound VII three times daily at 50 mg/kg/day for 5 days. FIG. 4 shows that all 6 of the infected mice survived over the test period when treated with compound VII (results for vancomycin not shown in FIG. 4. See FIG. 3 for comparable results).

Experimental Synthesis of Additional Type-B Lantibiotic Compounds

An additional series of type-B lantibiotic compounds was prepared as described in detail below. The parent lantibiotic actagardine was obtained in accordance with the methods described for this compound above.

Additional Actagardine Compounds

The following actagardine compounds were prepared, in which the parent lantibiotic, and the groups A, B, Y, Z and X were as follows:

| Compound | Lantibiotic | A | B | Y | Z | X |
|---|---|---|---|---|---|---|
| C | Actagardine | —CH(CH$_3$)$_2$ | —CH(CH$_3$)CH$_2$CH$_3$ | —S(O)— | —NH$_2$ | —NH(CH$_2$)$_7$NH$_2$ |
| CI | Actagardine | —CH(CH$_3$)$_2$ | —CH(CH$_3$)CH$_2$CH$_3$ | —S(O)— | —NH$_2$ | —NH(CH$_2$)$_5$NH$_2$ |
| CII | Actagardine | —CH(CH$_3$)$_2$ | —CH(CH$_3$)CH$_2$CH$_3$ | —S(O)— | —NH$_2$ | —NH(CH$_2$)$_4$NH$_2$ |

For X, the hyphen indicates the point where the nitrogen atom is linked to the alanine residue at position 19 via an amide bond.

Preparation of Compounds C-CII

Compound C: Actagardine (7-amino-1-heptylamide monocarboxamide)

Figure 5:
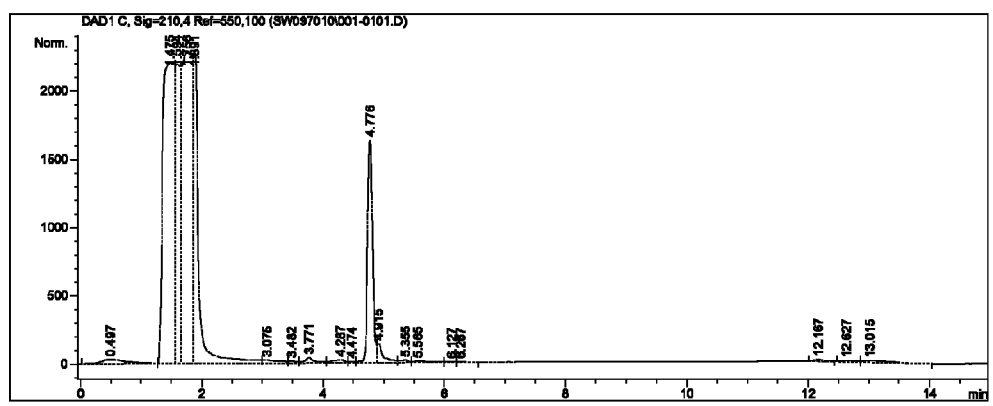
FIG. 5 is a HPLC trace of the starting materials for the preparation of Compound C.
Figure 6:
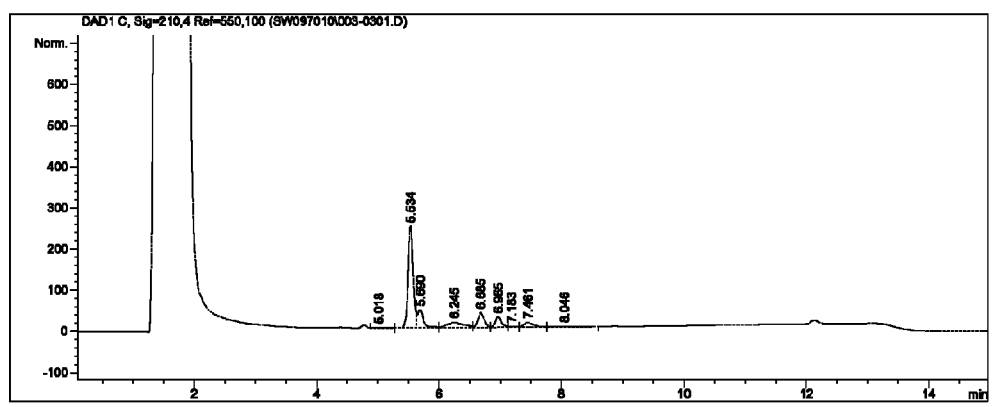
FIG. 6 is a HPLC trace of the completed reaction mixture in the preparation of Compound C, prior to C18 concentration.

Actagardine (25 mg), 1,7-diaminoheptane (3.4 mg) and diisopropylethylamine (5.3 μl) were dissolved in dry dimethylformamide (0.25 ml). A solution of benzotriazole-1-yl-oxy-tris-pyrrolidino-phosphonium hexafluorophosphate (PYBOP) (10.4 mg) in dry dimethylformamide (0.25 ml) was added portionwise. The reaction was followed by analytical HPLC (See Table 7) and PyBOP was added until the starting material had been consumed (FIGS. 5 and 6).

TABLE 7

Analytical HPLC conditions for the separation of lantibiotics (e.g. actagardine) and diaminoalkane derivatised products.

| | |
|---|---|
| Column | Zorbax 5μ C18(2) 150 × 4.6 mm |
| Mobile Phase A | 30% Acetonitrile in 20 mM potassium phosphate buffer pH 7.0 |
| Mobile Phase B | 65% Acetonitrile in 20 mM potassium phosphate buffer pH 7.0 |
| Detection | 210 nm |
| Flow Rate | 1 ml/min |
| Injection volume | 10 μl |

TABLE 7-continued

Analytical HPLC conditions for the separation of lantibiotics (e.g. actagardine) and diaminoalkane derivatised products.

| Time (T) = 0 min | 100% A, 0% B |
|---|---|
| T = 10 min | 0% A, 100% B |
| T = 11 min | 0% A, 100% B |
| T = 11.2 min | 100% A, 0% B |
| Cycle time | 15 min |

Figure 7:
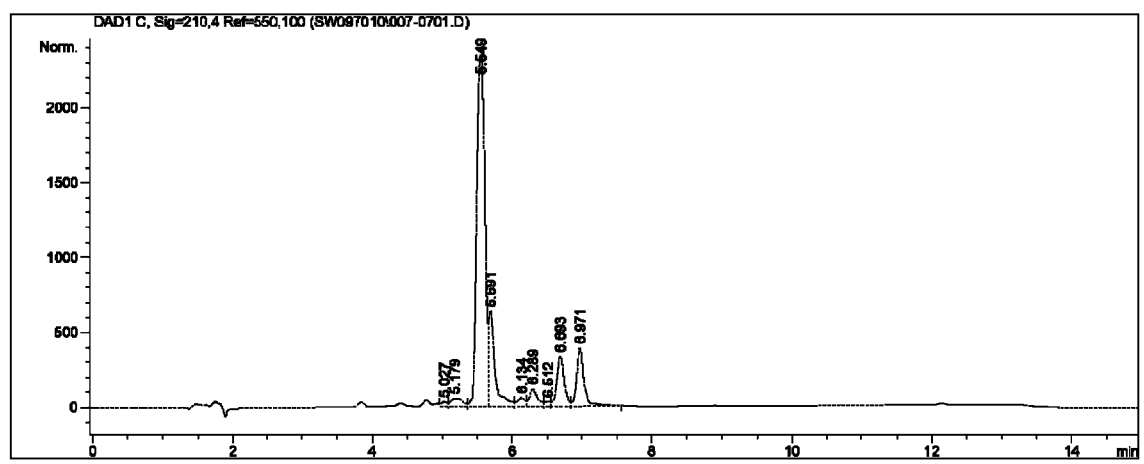
FIG. 7 is a HPLC trace of the completed reaction mixture in the preparation of Compound C, after C18 concentration.

The crude reaction mixture was poured into 30% aqueous methanol and the resulting solution was loaded on to a Varian Bond Elut C18 column (500 mg). The column was then washed sequentially with 50%, 60%, 70%, 80%, 90% aqueous methanol, with most of the desired material eluting in the 70% fraction (FIG. 7) Column chromatography on silica gel (eluent: dichloromethane:ethanol:ammonia 10:8:1) gave material of >90% purity by U.V. at 210 nm. Yield 15 mg (59%). Samples were analysed by LC-MS. Mass calc $(M+2H)^{+2}$ 1001.0, found 1001.02.

Compound CI: Actagardine 1,3-diaminopropane monocarboxamide

Was prepared by coupling actagardine with 1,3-diaminopropane utilising the procedure described for Example 1. Yield 47%. Mass calc $(M+H+Na)^{+2}$ 973.0, found 973.2.

Compound CII: Actagardine 1,4-diaminobutane monocarboxamide

Was prepared by coupling actagardine with 1,4-diaminobutane utilising the procedure described for Example 1. Yield 50%. Mass calc $(M+H+Na)^{+2}$ 990.5, found 989.46.

Example 8

Antibacterial Activity of Actagardine and Derivatives

The compounds of the invention show antimicrobial activity in vitro and are expected to show similar activity in vivo. They are active against *Clostridium difficile* and may have improved activity compared to actagardine.

Suceptibility testing for *Clostridium difficile* strains was performed by two-fold serial antibiotic dilutions in Wilkins-Chalgren Anaerobe agar under anaerobic conditions. Vancomycin was included as a comparator drug. *C. dificile* cultures were inoculated onto pre-reduced Braziers (C.C.E.Y.) agar plates and grown at 37° C. for 48 hours under anaerobic conditions. Two to three colonies of the 48 hours cultures were inoculated into 5 ml of pre-reduced Schaedlers Broth and grown at 37° C. for 24 hours under anaerobic conditions. This culture was diluted with pre-reduced 0.9% NaCl to achieve the turbidity of the 0.5 McFarland standard and applied to the drug containing plates at a final inoculum of 105 cfu/spot. Drug-free growth control plates were included. The plates were incubated in the anaerobic chamber at 37° C. for 48 hours and examined for growth. The MIC was the lowest concentration of drug that completely inhibited growth or caused markedly reduction of growth as compared to growth on the drug-free plates.

TABLE 8

MIC data (µg/ml) for actagardine and derivatives thereof.

| | | Compound Number | | |
|---|---|---|---|---|
| *C. difficile* strain | Actagardine | C | CI | CII |
| 37779 | 4-8 | 4 | 4 | 2-4 |
| 19126 | 4-8 | 4 | 4 | 4 |
| 027Can | ND | 2-4 | 2-4 | 2 |
| 630 | 8 | 2-4 | 2 | 2 |

(The Lower the Value of the Result the Greater the Activity of the Test Compound.)

It will be apparent to those skilled in the art that various modifications and variations can be made in the methods and compositions of the present invention without departing from the spirit or scope of the invention. Thus, it is intended that the present invention cover the modifications and variations of this invention provided they come within the scope of the appended claims and their equivalents.

REFERENCES

The following references are incorporated by reference herein in their entirety:

U.S. Pat. No. 6,022,851
U.S. Pat. No. 5,985,823
WO 91/07949
WO 02/088367
WO 2004/033706
WO 2005/093069
WO 2006/080920
WO 2007/036706
PCT/GB2007/000138 (WO/2007/083112)
EP 0572942
Berge, et al., *J. Pharm. Sci.* 1997, 66, 1-19
Castiglione, et al., *Biochemistry* 2007, 46, 5884-5895.
Dabard, et al., *Appl. Environ. Microbiol.* 2001, 67, 4111
Fukase, et al., *Bull. Chem. Soc. Jpn.* 1992, 65, 2227-2240
Hilger et al, *Clin. Exp. Immunol.* 2001, 123, 387-94
Holtsmark, et al., *Appl. Environ. Microbiol.* 2006, 72, 5814
Louie, et al., *Proceedings of 14th European Congress of Clinical Microbiology and Infectious Diseases, Prague Congress Centre, Prague, Czech Republic*, May 1-4, 2004).
McClerren, et al., *Proc. Nat. Acad. Sci.* 2006, 103, 17243
Rea, et al., *J. Med. Microbiol.* 2002, 56, 940
Rey, et al., *Genome Biology* 2004, 5, R77
Sahl, et al., *Ann. Rev. Microbiology* 1998, 52, 41
Szekat, et al., *Appl. Env. Microbiol.* 2003, 69, 3777-3783
Turner, et al., *Eur. J. Biochem.* 1999, 264, 833
Ugurlu, et al., *Eur. J. Pharm. Biopharm.* 2007, 67, 202
The Use of Nisin in Cheesemaking, *Bull. Int. Dairy Fed.* 1988, 329, 20-23
Merck Novabiochem™ catalogue '*Reagents for Peptide and High-Throughput Synthesis*' (2006/7)
"*Remington: The Science and Practice of Pharmacy*", 20th Edition, 2000, pub. Lippincott, Williams & Wilkins
"Protective Groups in Organic Synthesis" (T. Green and P. Wuts; 3rd Edition; John Wiley and Sons, 1999)

The invention claimed is:

1. A method for the treatment of a microbial infection of the lower intestine or colon in a subject in need there of, the method comprising administering to the subject a type-B lantibiotic of formula (Ia):

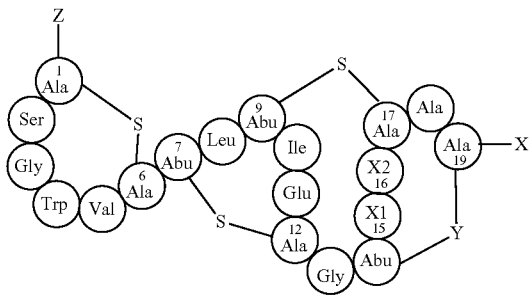

(Ia)

wherein the type-B lantibiotic has antimicrobial activity, and wherein:

X1 represents Leu; Val; or Ile;
X2 represents Leu; Val; or Ile;
X is —OH or —NR$^{1A}$R$^{2A}$, wherein R$^{1A}$ represents hydrogen, or an alkyl or heteroalkyl group, substituted by at least one hydroxyl substituent, and R$^{2A}$ represents hydrogen, or an alkyl or heteroalkyl group, substituted by at least one hydroxyl substituent, or R$^{1A}$ and R$^{2A}$ taken together with the nitrogen atom represent a heterocyclic group having at least one hydroxyl substituent, wherein the heterocyclic group optionally further contains one or more heteroatoms, or R$^{1A}$ and R$^{2A}$ independently represent:

(1) hydrogen;
(2) a group of formula —(CH$_2$)$_n$—NR$^{11}$R$^{12}$, in which n represents an integer from 2 to 12 and R$^{11}$ and R$^{12}$ independently represent hydrogen or (C$_1$-C$_4$) alkyl or R$^{11}$ and R$^{12}$ taken together represent a group —(CH$_2$)$_3$—, —(CH$_2$)$_4$—, —(CH$_2$)$_2$—O—(CH$_2$)$_2$, —(CH$_2$)$_2$—S—(CH$_2$)$_2$—or —(CH$_2$)$_5$—;
or R$^{1A}$ and R$^{2A}$ taken together with the adjacent nitrogen atom represent a piperazine which may be substituted in position 4 with a substituent selected from:

(a) (C$_1$-C$_4$)alkyl;
(b) (C$_5$-C$_2$)-cycloalkyl,
(c) pyridyl,
(d) —(CH$_2$)$_p$—NR$^{13}$R$^{14}$ in which p represents an integer from 1 to 8 and R$^{13}$ and R$^{14}$ independently represent hydrogen or (C$_1$-C$_4$) alkyl;
(e) piperidinyl;
(f) substituted piperidinyl, wherein the substituted piperidinyl bears a N-substituent which is (C$_1$-C$_4$)alkyl;
(g) benzyl; and
(h) substituted benzyl, wherein a phenyl therein bears 1 or 2 substituents selected from chloro, bromo, nitro, (C$_1$-C$_4$)alkyl and (C$_1$-C$_4$)alkoxy;

Z is an amino acid residue,
—NR$^3$R$^4$, —NR$^5$COR$^6$, —NR$^5$C(O)OR$^6$; —NR$^5$SOR$^6$, —NR$^5$SO$_2$R$^6$; —NR$^5$C(S)NR$^6$R$^7$, —NR$^5$C(NR$^8$)NR$^6$R$^7$, or —N=R$^9$, wherein each of these groups represents modifications of the N-terminus of the amino acid at position 1, and where R$^3$, R$^4$, R$^5$, R$^6$, R$^7$, R$^8$ and R$^9$ are independently hydrogen, or a group, optionally substituted, selected from alkyl, heteroalkyl, aryl, heteroaryl, aralkyl and heteroaralkyl, with the proviso that R$^9$ is not hydrogen; and Y is —S— or —S(O)—;
or a variant, derivative, pharmaceutically acceptable salt thereof,
wherein a variant is a compound where 1, 2, 3 or 4 amino acids at positions 2, 3, 4, 5, 8, 10, 11, 13 or 18 are substituted by another amino acid, and the another amino acid is a naturally occurring amino acid or its D-isoform,
and a derivative is a compound where the carboxy function of a side chain of an internal residue, is modified from —COOH to a group —COOR$_9$ in which R$_9$ represents (C$_1$-C$_4$)alkyl or (C$_1$-C$_4$)alkoxy(C$_2$-C$_4$)alkyl.

2. The method of claim 1, comprising orally administering to the subject the type-B lantibiotic.

3. The method of claim 1, wherein the microbial infection is a bacterial infection.

4. The method of claim 3, wherein the bacterial infection is a clostridial infection.

5. The method of claim 4, wherein the clostridial infection is a *Clostridium perfringens*, *Clostridium difficile*, *Clostridium tetani* or *Clostridium botulinum* infection.

6. The method of claim 5, wherein the clostridial infection is a *Clostridium difficile* infection.

7. The method of claim 1, wherein the compound of formula (Ia) is an actagardine compound of formula (Ib):

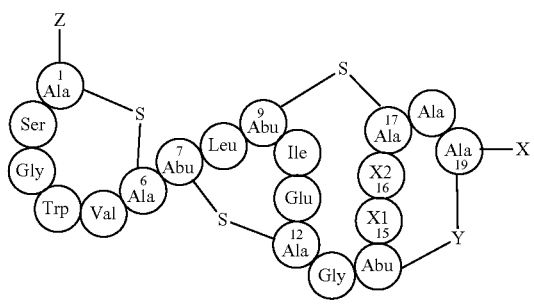

(Ib)

-continued

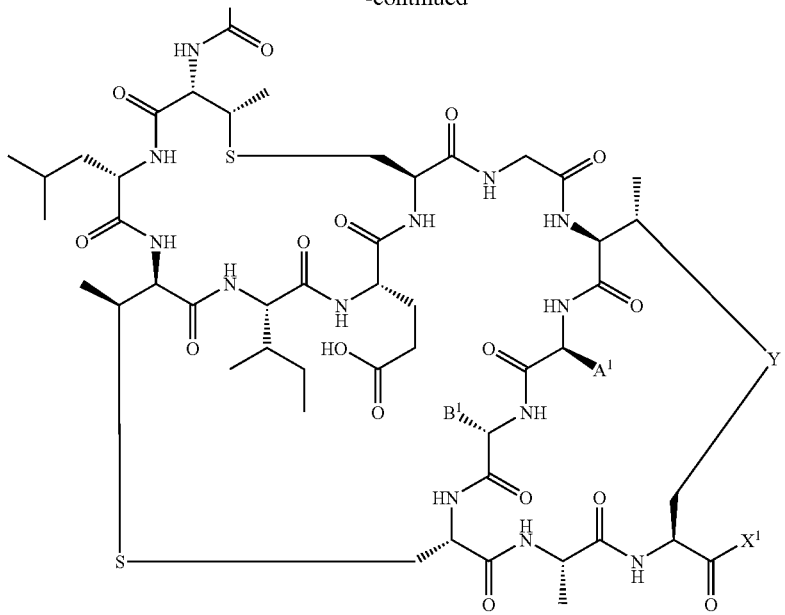

wherein:
X1 represents Leu; Val; or Ile;
X2 represents Leu; Val; or Ile;
X is —NR$^{14}$R$^{24}$;
where R$^{14}$ is a group of formula —(CH$_2$)$_n$—NR$^{11}$R$^{12}$, in which n represents an integer from 2 to 12, and R$^{11}$ and R$^{12}$ are each hydrogen;
R$^{24}$ is hydrogen;
Z is an amino acid residue or a modification to the N-terminus of the amino acid at position 1, —NR$^3$R$^4$, where R$^3$ is hydrogen or C$_{1-4}$ alkyl, and R$^4$ is hydrogen or C$_{1-4}$ alkyl; and
Y is —S(O)—;
or a pharmaceutically acceptable salt thereof.

8. The method of claim 7, wherein X1 represents Val or Leu.

9. The method of claim 8, wherein X1 represents Val.

10. The method of claim 7, wherein X2 represents Val or Ile.

11. The method of claim 10, wherein X2 represents Ile.

12. The method of claim 7, wherein Z is the L or D isomer form of alanine.

13. The method of claim 7, wherein X1 represents Val and X2 represents Ile.

14. The method of claim 7, wherein n is 2, 3, 4, 5, 6, 7, 8, 9, 10, 11 or 12.

15. The method of claim 14, wherein n is 2, 3, 7, 9 or 12.

16. The method of claim 15, wherein n is 7, 9 or 12.

17. The method of claim 7, wherein Z is NH$_2$.

18. The method of claim 7, wherein the compound of formula (Ib) is actagardine (7-amino-1-heptylamide monocarboxamide) or a pharmaceutically acceptable salt thereof.

* * * * *

SEQUENCE LISTING

<160> NUMBER OF SEQ ID NOS: 34

<210> SEQ ID NO 1
<211> LENGTH: 19
<212> TYPE: PRT
<213> ORGANISM: Artificial sequence
<220> FEATURE:
<223> OTHER INFORMATION: Synthetic sequence: Actagardine compound of
      Formula I
<220> FEATURE:
<221> NAME/KEY: THIOETH
<222> LOCATION: (1)..(6)
<220> FEATURE:
<221> NAME/KEY: MOD_RES
<222> LOCATION: 7, 9, 14
<223> OTHER INFORMATION: Xaa is 4Abu
<220> FEATURE:
<221> NAME/KEY: THIOETH
<222> LOCATION: (7)..(12)
<220> FEATURE:
<221> NAME/KEY: THIOETH
<222> LOCATION: (9)..(17)
<220> FEATURE:
<221> NAME/KEY: THIOETH
<222> LOCATION: (14)..(19)
<223> OTHER INFORMATION: Linked by Y, where Y is -S- or -S(O)-

<400> SEQUENCE: 1

Ala Ser Gly Trp Val Ala Xaa Leu Xaa Ile Glu Ala Gly Xaa Leu Leu
1               5                   10                  15

Ala Ala Ala

<210> SEQ ID NO 2
<211> LENGTH: 19
<212> TYPE: PRT
<213> ORGANISM: Artificial sequence
<220> FEATURE:
<223> OTHER INFORMATION: Synthetic sequence: Actagardine compound of
      Formula I
<220> FEATURE:
<221> NAME/KEY: THIOETH
<222> LOCATION: (1)..(6)
<220> FEATURE:
<221> NAME/KEY: MOD_RES
<222> LOCATION: 7, 9, 14
<223> OTHER INFORMATION: Xaa is 4Abu
<220> FEATURE:
<221> NAME/KEY: THIOETH
<222> LOCATION: (7)..(12)
<220> FEATURE:
<221> NAME/KEY: THIOETH
<222> LOCATION: (9)..(17)
<220> FEATURE:
<221> NAME/KEY: THIOETH
<222> LOCATION: (14)..(19)
<223> OTHER INFORMATION: Linked by Y, where Y is -S- or -S(O)-

<400> SEQUENCE: 2

Ala Ser Gly Trp Val Ala Xaa Leu Xaa Ile Glu Ala Gly Xaa Leu Val
1               5                   10                  15

Ala Ala Ala

<210> SEQ ID NO 3
<211> LENGTH: 19
<212> TYPE: PRT
<213> ORGANISM: Artificial sequence
<220> FEATURE:
<223> OTHER INFORMATION: Synthetic sequence: Actagardine compound of
      Formula I
<220> FEATURE:
<221> NAME/KEY: THIOETH

```
<222> LOCATION: (1)..(6)
<220> FEATURE:
<221> NAME/KEY: MOD_RES
<222> LOCATION: 7, 9, 14
<223> OTHER INFORMATION: Xaa is 4Abu
<220> FEATURE:
<221> NAME/KEY: THIOETH
<222> LOCATION: (7)..(12)
<220> FEATURE:
<221> NAME/KEY: THIOETH
<222> LOCATION: (9)..(17)
<220> FEATURE:
<221> NAME/KEY: THIOETH
<222> LOCATION: (14)..(19)
<223> OTHER INFORMATION: Linked by Y, where Y is -S- or -S(O)-

<400> SEQUENCE: 3

Ala Ser Gly Trp Val Ala Xaa Leu Xaa Ile Glu Ala Gly Xaa Leu Ile
1               5                   10                  15

Ala Ala Ala

<210> SEQ ID NO 4
<211> LENGTH: 19
<212> TYPE: PRT
<213> ORGANISM: Artificial sequence
<220> FEATURE:
<223> OTHER INFORMATION: Synthetic sequence: Actagardine compound of
      Formula I
<220> FEATURE:
<221> NAME/KEY: THIOETH
<222> LOCATION: (1)..(6)
<220> FEATURE:
<221> NAME/KEY: MOD_RES
<222> LOCATION: 7, 9, 14
<223> OTHER INFORMATION: Xaa is 4Abu
<220> FEATURE:
<221> NAME/KEY: THIOETH
<222> LOCATION: (7)..(12)
<220> FEATURE:
<221> NAME/KEY: THIOETH
<222> LOCATION: (9)..(17)
<220> FEATURE:
<221> NAME/KEY: THIOETH
<222> LOCATION: (14)..(19)
<223> OTHER INFORMATION: Linked by Y, where Y is -S- or -S(O)-

<400> SEQUENCE: 4

Ala Ser Gly Trp Val Ala Xaa Leu Xaa Ile Glu Ala Gly Xaa Val Leu
1               5                   10                  15

Ala Ala Ala

<210> SEQ ID NO 5
<211> LENGTH: 19
<212> TYPE: PRT
<213> ORGANISM: Artificial sequence
<220> FEATURE:
<223> OTHER INFORMATION: Synthetic sequence: Actagardine compound of
      Formula I
<220> FEATURE:
<221> NAME/KEY: THIOETH
<222> LOCATION: (1)..(6)
<220> FEATURE:
<221> NAME/KEY: MOD_RES
<222> LOCATION: 7, 9, 14
<223> OTHER INFORMATION: Xaa is 4Abu
<220> FEATURE:
<221> NAME/KEY: THIOETH
<222> LOCATION: (7)..(12)
<220> FEATURE:
<221> NAME/KEY: THIOETH
<222> LOCATION: (9)..(17)
<220> FEATURE:
<221> NAME/KEY: THIOETH
<222> LOCATION: (14)..(19)
```

```
<223> OTHER INFORMATION: Linked by Y, where Y is -S- or -S(O)-

<400> SEQUENCE: 5

Ala Ser Gly Trp Val Ala Xaa Leu Xaa Ile Glu Ala Gly Xaa Val Val
1               5                   10                  15

Ala Ala Ala

<210> SEQ ID NO 6
<211> LENGTH: 19
<212> TYPE: PRT
<213> ORGANISM: Artificial sequence
<220> FEATURE:
<223> OTHER INFORMATION: Synthetic sequence: Actagardine compound of
      Formula I
<220> FEATURE:
<221> NAME/KEY: THIOETH
<222> LOCATION: (1)..(6)
<220> FEATURE:
<221> NAME/KEY: MOD_RES
<222> LOCATION: 7, 9, 14
<223> OTHER INFORMATION: Xaa is 4Abu
<220> FEATURE:
<221> NAME/KEY: THIOETH
<222> LOCATION: (7)..(12)
<220> FEATURE:
<221> NAME/KEY: THIOETH
<222> LOCATION: (9)..(17)
<220> FEATURE:
<221> NAME/KEY: THIOETH
<222> LOCATION: (14)..(19)
<223> OTHER INFORMATION: Linked by Y, where Y is -S- or -S(O)-

<400> SEQUENCE: 6

Ala Ser Gly Trp Val Ala Xaa Leu Xaa Ile Glu Ala Gly Xaa Val Ile
1               5                   10                  15

Ala Ala Ala

<210> SEQ ID NO 7
<211> LENGTH: 19
<212> TYPE: PRT
<213> ORGANISM: Artificial sequence
<220> FEATURE:
<223> OTHER INFORMATION: Synthetic sequence: Actagardine compound of
      Formula I
<220> FEATURE:
<221> NAME/KEY: THIOETH
<222> LOCATION: (1)..(6)
<220> FEATURE:
<221> NAME/KEY: MOD_RES
<222> LOCATION: 7, 9, 14
<223> OTHER INFORMATION: Xaa is 4Abu
<220> FEATURE:
<221> NAME/KEY: THIOETH
<222> LOCATION: (7)..(12)
<220> FEATURE:
<221> NAME/KEY: THIOETH
<222> LOCATION: (9)..(17)
<220> FEATURE:
<221> NAME/KEY: THIOETH
<222> LOCATION: (14)..(19)
<223> OTHER INFORMATION: Linked by Y, where Y is -S- or -S(O)-

<400> SEQUENCE: 7

Ala Ser Gly Trp Val Ala Xaa Leu Xaa Ile Glu Ala Gly Xaa Ile Leu
1               5                   10                  15

Ala Ala Ala

<210> SEQ ID NO 8
<211> LENGTH: 19
<212> TYPE: PRT
<213> ORGANISM: Artificial sequence
```

```
<220> FEATURE:
<223> OTHER INFORMATION: Synthetic sequence: Actagardine compound of
      Formula I
<220> FEATURE:
<221> NAME/KEY: THIOETH
<222> LOCATION: (1)..(6)
<220> FEATURE:
<221> NAME/KEY: MOD_RES
<222> LOCATION: 7, 9, 14
<223> OTHER INFORMATION: Xaa is 4Abu
<220> FEATURE:
<221> NAME/KEY: THIOETH
<222> LOCATION: (7)..(12)
<220> FEATURE:
<221> NAME/KEY: THIOETH
<222> LOCATION: (9)..(17)
<220> FEATURE:
<221> NAME/KEY: THIOETH
<222> LOCATION: (14)..(19)
<223> OTHER INFORMATION: Linked by Y, where Y is -S- or -S(O)-

<400> SEQUENCE: 8

Ala Ser Gly Trp Val Ala Xaa Leu Xaa Ile Glu Ala Gly Xaa Ile Val
1               5                   10                  15

Ala Ala Ala

<210> SEQ ID NO 9
<211> LENGTH: 19
<212> TYPE: PRT
<213> ORGANISM: Artificial sequence
<220> FEATURE:
<223> OTHER INFORMATION: Synthetic sequence: Actagardine compound of
      Formula I
<220> FEATURE:
<221> NAME/KEY: THIOETH
<222> LOCATION: (1)..(6)
<220> FEATURE:
<221> NAME/KEY: MOD_RES
<222> LOCATION: 7, 9, 14
<223> OTHER INFORMATION: Xaa is 4Abu
<220> FEATURE:
<221> NAME/KEY: THIOETH
<222> LOCATION: (7)..(12)
<220> FEATURE:
<221> NAME/KEY: THIOETH
<222> LOCATION: (9)..(17)
<220> FEATURE:
<221> NAME/KEY: THIOETH
<222> LOCATION: (14)..(19)
<223> OTHER INFORMATION: Linked by Y, where Y is -S- or -S(O)-

<400> SEQUENCE: 9

Ala Ser Gly Trp Val Ala Xaa Leu Xaa Ile Glu Ala Gly Xaa Ile Ile
1               5                   10                  15

Ala Ala Ala

<210> SEQ ID NO 10
<211> LENGTH: 20
<212> TYPE: PRT
<213> ORGANISM: Artificial sequence
<220> FEATURE:
<223> OTHER INFORMATION: Synthetic sequence: Actagardine compound of
      Formula I
<220> FEATURE:
<221> NAME/KEY: VARIANT
<222> LOCATION: (1)..(1)
<223> OTHER INFORMATION: Xaa is an amino acid residue
<220> FEATURE:
<221> NAME/KEY: SITE
<222> LOCATION: (1)..(2)
<223> OTHER INFORMATION: Xaa is linked to Ala via an amide bond
<220> FEATURE:
<221> NAME/KEY: THIOETH
<222> LOCATION: (2)..(7)
```

```
-continued

<220> FEATURE:
<221> NAME/KEY: THIOETH
<222> LOCATION: (8)..(13)
<220> FEATURE:
<221> NAME/KEY: MOD_RES
<222> LOCATION: 8, 10, 15
<223> OTHER INFORMATION: Xaa is 4Abu
<220> FEATURE:
<221> NAME/KEY: THIOETH
<222> LOCATION: (10)..(18)
<220> FEATURE:
<221> NAME/KEY: THIOETH
<222> LOCATION: (15)..(20)
<223> OTHER INFORMATION: Linked by Y, where Y is -S- or -S(O)-

<400> SEQUENCE: 10

Xaa Ala Ser Gly Trp Val Ala Xaa Leu Xaa Ile Glu Ala Gly Xaa Leu
1               5                   10                  15

Leu Ala Ala Ala
            20

<210> SEQ ID NO 11
<211> LENGTH: 20
<212> TYPE: PRT
<213> ORGANISM: Artificial sequence
<220> FEATURE:
<223> OTHER INFORMATION: Synthetic sequence: Actagardine compound of
      Formula I
<220> FEATURE:
<221> NAME/KEY: VARIANT
<222> LOCATION: (1)..(1)
<223> OTHER INFORMATION: Xaa is an amino acid residue
<220> FEATURE:
<221> NAME/KEY: SITE
<222> LOCATION: (1)..(2)
<223> OTHER INFORMATION: Xaa is linked to Ala via an amide bond
<220> FEATURE:
<221> NAME/KEY: THIOETH
<222> LOCATION: (2)..(7)
<220> FEATURE:
<221> NAME/KEY: THIOETH
<222> LOCATION: (8)..(13)
<220> FEATURE:
<221> NAME/KEY: MOD_RES
<222> LOCATION: 8, 10, 15
<223> OTHER INFORMATION: Xaa is 4Abu
<220> FEATURE:
<221> NAME/KEY: THIOETH
<222> LOCATION: (10)..(18)
<220> FEATURE:
<221> NAME/KEY: THIOETH
<222> LOCATION: (15)..(20)
<223> OTHER INFORMATION: Linked by Y, where Y is -S- or -S(O)-

<400> SEQUENCE: 11

Xaa Ala Ser Gly Trp Val Ala Xaa Leu Xaa Ile Glu Ala Gly Xaa Leu
1               5                   10                  15

Val Ala Ala Ala
            20

<210> SEQ ID NO 12
<211> LENGTH: 20
<212> TYPE: PRT
<213> ORGANISM: Artificial sequence
<220> FEATURE:
<223> OTHER INFORMATION: Synthetic sequence: Actagardine compound of
      Formula I
<220> FEATURE:
<221> NAME/KEY: VARIANT
<222> LOCATION: (1)..(1)
<223> OTHER INFORMATION: Xaa is an amino acid residue
<220> FEATURE:
<221> NAME/KEY: SITE
<222> LOCATION: (1)..(2)
```

```
<223> OTHER INFORMATION: Xaa is linked to Ala via an amide bond
<220> FEATURE:
<221> NAME/KEY: THIOETH
<222> LOCATION: (2)..(7)
<220> FEATURE:
<221> NAME/KEY: THIOETH
<222> LOCATION: (8)..(13)
<220> FEATURE:
<221> NAME/KEY: MOD_RES
<222> LOCATION: 8, 10, 15
<223> OTHER INFORMATION: Xaa is 4Abu
<220> FEATURE:
<221> NAME/KEY: THIOETH
<222> LOCATION: (10)..(18)
<220> FEATURE:
<221> NAME/KEY: THIOETH
<222> LOCATION: (15)..(20)
<223> OTHER INFORMATION: Linked by Y, where Y is -S- or -S(O)-

<400> SEQUENCE: 12

Xaa Ala Ser Gly Trp Val Ala Xaa Leu Xaa Ile Glu Ala Gly Xaa Leu
1               5                   10                  15

Ile Ala Ala Ala
            20

<210> SEQ ID NO 13
<211> LENGTH: 20
<212> TYPE: PRT
<213> ORGANISM: Artificial sequence
<220> FEATURE:
<223> OTHER INFORMATION: Synthetic sequence: Actagardine compound of
      Formula I
<220> FEATURE:
<221> NAME/KEY: VARIANT
<222> LOCATION: (1)..(1)
<223> OTHER INFORMATION: Xaa is an amino acid residue
<220> FEATURE:
<221> NAME/KEY: SITE
<222> LOCATION: (1)..(2)
<223> OTHER INFORMATION: Xaa is linked to Ala via an amide bond
<220> FEATURE:
<221> NAME/KEY: THIOETH
<222> LOCATION: (2)..(7)
<220> FEATURE:
<221> NAME/KEY: THIOETH
<222> LOCATION: (8)..(13)
<220> FEATURE:
<221> NAME/KEY: MOD_RES
<222> LOCATION: 8, 10, 15
<223> OTHER INFORMATION: Xaa is 4Abu
<220> FEATURE:
<221> NAME/KEY: THIOETH
<222> LOCATION: (10)..(18)
<220> FEATURE:
<221> NAME/KEY: THIOETH
<222> LOCATION: (15)..(20)
<223> OTHER INFORMATION: Linked by Y, where Y is -S- or -S(O)-

<400> SEQUENCE: 13

Xaa Ala Ser Gly Trp Val Ala Xaa Leu Xaa Ile Glu Ala Gly Xaa Val
1               5                   10                  15

Leu Ala Ala Ala
            20

<210> SEQ ID NO 14
<211> LENGTH: 20
<212> TYPE: PRT
<213> ORGANISM: Artificial sequence
<220> FEATURE:
<223> OTHER INFORMATION: Synthetic sequence: Actagardine compound of
      Formula I
<220> FEATURE:
<221> NAME/KEY: VARIANT
<222> LOCATION: (1)..(1)
```

-continued

```
<223> OTHER INFORMATION: Xaa is an amino acid residue
<220> FEATURE:
<221> NAME/KEY: SITE
<222> LOCATION: (1)..(2)
<223> OTHER INFORMATION: Xaa is linked to Ala via an amide bond
<220> FEATURE:
<221> NAME/KEY: THIOETH
<222> LOCATION: (2)..(7)
<220> FEATURE:
<221> NAME/KEY: THIOETH
<222> LOCATION: (8)..(13)
<220> FEATURE:
<221> NAME/KEY: MOD_RES
<222> LOCATION: 8, 10, 15
<223> OTHER INFORMATION: Xaa is 4Abu
<220> FEATURE:
<221> NAME/KEY: THIOETH
<222> LOCATION: (10)..(18)
<220> FEATURE:
<221> NAME/KEY: THIOETH
<222> LOCATION: (15)..(20)
<223> OTHER INFORMATION: Linked by Y, where Y is -S- or -S(O)-

<400> SEQUENCE: 14

Xaa Ala Ser Gly Trp Val Ala Xaa Leu Xaa Ile Glu Ala Gly Xaa Val
1               5                   10                  15

Val Ala Ala Ala
        20

<210> SEQ ID NO 15
<211> LENGTH: 20
<212> TYPE: PRT
<213> ORGANISM: Artificial sequence
<220> FEATURE:
<223> OTHER INFORMATION: Synthetic sequence: Actagardine compound of
      Formula I
<220> FEATURE:
<221> NAME/KEY: VARIANT
<222> LOCATION: (1)..(1)
<223> OTHER INFORMATION: Xaa is an amino acid residue
<220> FEATURE:
<221> NAME/KEY: SITE
<222> LOCATION: (1)..(2)
<223> OTHER INFORMATION: Xaa is linked to Ala via an amide bond
<220> FEATURE:
<221> NAME/KEY: THIOETH
<222> LOCATION: (2)..(7)
<220> FEATURE:
<221> NAME/KEY: THIOETH
<222> LOCATION: (8)..(13)
<220> FEATURE:
<221> NAME/KEY: MOD_RES
<222> LOCATION: 8, 10, 15
<223> OTHER INFORMATION: Xaa is 4Abu
<220> FEATURE:
<221> NAME/KEY: THIOETH
<222> LOCATION: (10)..(18)
<220> FEATURE:
<221> NAME/KEY: THIOETH
<222> LOCATION: (15)..(20)
<223> OTHER INFORMATION: Linked by Y, where Y is -S- or -S(O)-

<400> SEQUENCE: 15

Xaa Ala Ser Gly Trp Val Ala Xaa Leu Xaa Ile Glu Ala Gly Xaa Val
1               5                   10                  15

Ile Ala Ala Ala
        20

<210> SEQ ID NO 16
<211> LENGTH: 20
<212> TYPE: PRT
<213> ORGANISM: Artificial sequence
<220> FEATURE:
<223> OTHER INFORMATION: Synthetic sequence: Actagardine compound of
```

```
                         Formula I
<220> FEATURE:
<221> NAME/KEY: VARIANT
<222> LOCATION: (1)..(1)
<223> OTHER INFORMATION: Xaa is an amino acid residue
<220> FEATURE:
<221> NAME/KEY: SITE
<222> LOCATION: (1)..(2)
<223> OTHER INFORMATION: Xaa is linked to Ala via an amide bond
<220> FEATURE:
<221> NAME/KEY: THIOETH
<222> LOCATION: (2)..(7)
<220> FEATURE:
<221> NAME/KEY: THIOETH
<222> LOCATION: (8)..(13)
<220> FEATURE:
<221> NAME/KEY: MOD_RES
<222> LOCATION: 8, 10, 15
<223> OTHER INFORMATION: Xaa is 4Abu
<220> FEATURE:
<221> NAME/KEY: THIOETH
<222> LOCATION: (10)..(18)
<220> FEATURE:
<221> NAME/KEY: THIOETH
<222> LOCATION: (15)..(20)
<223> OTHER INFORMATION: Linked by Y, where Y is -S- or -S(O)-

<400> SEQUENCE: 16

Xaa Ala Ser Gly Trp Val Ala Xaa Leu Xaa Ile Glu Ala Gly Xaa Ile
1               5                   10                  15

Leu Ala Ala Ala
            20

<210> SEQ ID NO 17
<211> LENGTH: 20
<212> TYPE: PRT
<213> ORGANISM: Artificial sequence
<220> FEATURE:
<223> OTHER INFORMATION: Synthetic sequence: Actagardine compound of
      Formula I
<220> FEATURE:
<221> NAME/KEY: VARIANT
<222> LOCATION: (1)..(1)
<223> OTHER INFORMATION: Xaa is an amino acid residue
<220> FEATURE:
<221> NAME/KEY: SITE
<222> LOCATION: (1)..(2)
<223> OTHER INFORMATION: Xaa is linked to Ala via an amide bond
<220> FEATURE:
<221> NAME/KEY: THIOETH
<222> LOCATION: (2)..(7)
<220> FEATURE:
<221> NAME/KEY: THIOETH
<222> LOCATION: (8)..(13)
<220> FEATURE:
<221> NAME/KEY: MOD_RES
<222> LOCATION: 8, 10, 15
<223> OTHER INFORMATION: Xaa is 4Abu
<220> FEATURE:
<221> NAME/KEY: THIOETH
<222> LOCATION: (10)..(18)
<220> FEATURE:
<221> NAME/KEY: THIOETH
<222> LOCATION: (15)..(20)
<223> OTHER INFORMATION: Linked by Y, where Y is -S- or -S(O)-

<400> SEQUENCE: 17

Xaa Ala Ser Gly Trp Val Ala Xaa Leu Xaa Ile Glu Ala Gly Xaa Ile
1               5                   10                  15

Val Ala Ala Ala
            20

<210> SEQ ID NO 18
<211> LENGTH: 20
```

```
<212> TYPE: PRT
<213> ORGANISM: Artificial sequence
<220> FEATURE:
<223> OTHER INFORMATION: Synthetic sequence: Actagardine compound of
      Formula I
<220> FEATURE:
<221> NAME/KEY: VARIANT
<222> LOCATION: (1)..(1)
<223> OTHER INFORMATION: Xaa is an amino acid residue
<220> FEATURE:
<221> NAME/KEY: SITE
<222> LOCATION: (1)..(2)
<223> OTHER INFORMATION: Xaa is linked to Ala via an amide bond
<220> FEATURE:
<221> NAME/KEY: THIOETH
<222> LOCATION: (2)..(7)
<220> FEATURE:
<221> NAME/KEY: THIOETH
<222> LOCATION: (8)..(13)
<220> FEATURE:
<221> NAME/KEY: MOD_RES
<222> LOCATION: 8, 10, 15
<223> OTHER INFORMATION: Xaa is 4Abu
<220> FEATURE:
<221> NAME/KEY: THIOETH
<222> LOCATION: (10)..(18)
<220> FEATURE:
<221> NAME/KEY: THIOETH
<222> LOCATION: (15)..(20)
<223> OTHER INFORMATION: Linked by Y, where Y is -S- or -S(O)-

<400> SEQUENCE: 18

Xaa Ala Ser Gly Trp Val Ala Xaa Leu Xaa Ile Glu Ala Gly Xaa Ile
1               5                   10                  15

Ile Ala Ala Ala
            20

<210> SEQ ID NO 19
<211> LENGTH: 19
<212> TYPE: PRT
<213> ORGANISM: Artificial sequence
<220> FEATURE:
<223> OTHER INFORMATION: Synthetic sequence: Actagardine compound of
      Formula Ia
<220> FEATURE:
<221> NAME/KEY: THIOETH
<222> LOCATION: (1)..(6)
<220> FEATURE:
<221> NAME/KEY: MOD_RES
<222> LOCATION: 7, 9, 14
<223> OTHER INFORMATION: Xaa is 4Abu
<220> FEATURE:
<221> NAME/KEY: THIOETH
<222> LOCATION: (7)..(12)
<220> FEATURE:
<221> NAME/KEY: THIOETH
<222> LOCATION: (9)..(17)
<220> FEATURE:
<221> NAME/KEY: THIOETH
<222> LOCATION: (14)..(19)
<223> OTHER INFORMATION: Linked by Y, where Y is -S- or -S(O)-
<220> FEATURE:
<221> NAME/KEY: Variant
<222> LOCATION: 15
<223> OTHER INFORMATION: Xaa is -C1-4 alkyl
<220> FEATURE:
<221> NAME/KEY: Variant
<222> LOCATION: 16
<223> OTHER INFORMATION: Xaa is -C1-4 alkyl

<400> SEQUENCE: 19

Ala Ser Gly Trp Val Ala Xaa Leu Xaa Ile Glu Ala Gly Xaa Xaa Xaa
1               5                   10                  15

Ala Ala Ala
```

```
<210> SEQ ID NO 20
<211> LENGTH: 20
<212> TYPE: PRT
<213> ORGANISM: Artificial sequence
<220> FEATURE:
<223> OTHER INFORMATION: Synthetic sequence: Actagardine compound of
      Formula Ia
<220> FEATURE:
<221> NAME/KEY: VARIANT
<222> LOCATION: (1)..(1)
<223> OTHER INFORMATION: Xaa is an amino acid residue
<220> FEATURE:
<221> NAME/KEY: SITE
<222> LOCATION: (1)..(2)
<223> OTHER INFORMATION: Xaa is linked to Ala via an amide bond
<220> FEATURE:
<221> NAME/KEY: THIOETH
<222> LOCATION: (2)..(7)
<220> FEATURE:
<221> NAME/KEY: THIOETH
<222> LOCATION: (8)..(13)
<220> FEATURE:
<221> NAME/KEY: MOD_RES
<222> LOCATION: 8, 10, 15
<223> OTHER INFORMATION: Xaa is 4Abu
<220> FEATURE:
<221> NAME/KEY: THIOETH
<222> LOCATION: (10)..(18)
<220> FEATURE:
<221> NAME/KEY: THIOETH
<222> LOCATION: (15)..(20)
<223> OTHER INFORMATION: Linked by Y, where Y is -S- or -S(O)-
<220> FEATURE:
<221> NAME/KEY: Variant
<222> LOCATION: 16
<223> OTHER INFORMATION: Xaa is -C1-4 alkyl
<220> FEATURE:
<221> NAME/KEY: Variant
<222> LOCATION: 17
<223> OTHER INFORMATION: Xaa is -C1-4 alkyl

<400> SEQUENCE: 20

Xaa Ala Ser Gly Trp Val Ala Xaa Leu Xaa Ile Glu Ala Gly Xaa Xaa
1               5                   10                  15

Xaa Ala Ala Ala
            20

<210> SEQ ID NO 21
<211> LENGTH: 20
<212> TYPE: PRT
<213> ORGANISM: Artificial sequence
<220> FEATURE:
<223> OTHER INFORMATION: Synthetic sequence: Mersacidin compound of
      Formula (II)
<220> FEATURE:
<221> NAME/KEY: THIOETH
<222> LOCATION: (1)..(2)
<220> FEATURE:
<221> NAME/KEY: MOD_RES
<222> LOCATION: 2, 4, 13, 15
<223> OTHER INFORMATION: Xaa is Abu
<220> FEATURE:
<221> NAME/KEY: THIOETH
<222> LOCATION: (4)..(12)
<220> FEATURE:
<221> NAME/KEY: THIOETH
<222> LOCATION: (13)..(18)
<220> FEATURE:
<221> NAME/KEY: THIOETH
<222> LOCATION: (15)..(20)
<220> FEATURE:
<221> NAME/KEY: MISC_FEATURE
<222> LOCATION: (16)..(16)
<223> OTHER INFORMATION: Xaa is dehydroalanine, Dha

<400> SEQUENCE: 21
```

```
Ala Xaa Phe Xaa Leu Pro Gly Gly Gly Gly Val Ala Xaa Leu Xaa Xaa
1               5                   10                  15

Glu Ala Ile Thr
            20
```

<210> SEQ ID NO 22
<211> LENGTH: 21
<212> TYPE: PRT
<213> ORGANISM: Artificial sequence
<220> FEATURE:
<223> OTHER INFORMATION: Synthetic sequence: Mersacidin compound of
      Formula (II)
<220> FEATURE:
<221> NAME/KEY: VARIANT
<222> LOCATION: (1)..(1)
<223> OTHER INFORMATION: Xaa is an amino acid residue
<220> FEATURE:
<221> NAME/KEY: SITE
<222> LOCATION: (1)..(2)
<223> OTHER INFORMATION: Xaa is linked to Ala via an amide bond
<220> FEATURE:
<221> NAME/KEY: THIOETH
<222> LOCATION: (2)..(3)
<220> FEATURE:
<221> NAME/KEY: MOD_RES
<222> LOCATION: 3, 5, 14, 16
<223> OTHER INFORMATION: Xaa is Abu
<220> FEATURE:
<221> NAME/KEY: THIOETH
<222> LOCATION: (5)..(13)
<220> FEATURE:
<221> NAME/KEY: THIOETH
<222> LOCATION: (14)..(19)
<220> FEATURE:
<221> NAME/KEY: THIOETH
<222> LOCATION: (16)..(21)
<220> FEATURE:
<221> NAME/KEY: MISC_FEATURE
<222> LOCATION: (17)..(17)
<223> OTHER INFORMATION: Xaa is dehydroalanine, Dha

<400> SEQUENCE: 22

```
Xaa Ala Xaa Phe Xaa Leu Pro Gly Gly Gly Gly Val Ala Xaa Leu Xaa
1               5                   10                  15

Xaa Glu Ala Ile Thr
                20
```

<210> SEQ ID NO 23
<211> LENGTH: 27
<212> TYPE: PRT
<213> ORGANISM: Lactobacillus plantarum
<220> FEATURE:
<221> NAME/KEY: THIOETH
<222> LOCATION: (7)..(27)
<220> FEATURE:
<221> NAME/KEY: THIOETH
<222> LOCATION: (12)..(15)
<220> FEATURE:
<221> NAME/KEY: MOD_RES
<222> LOCATION: 13, 15, 23
<223> OTHER INFORMATION: Abu
<220> FEATURE:
<221> NAME/KEY: THIOETH
<222> LOCATION: (13)..(18)
<220> FEATURE:
<221> NAME/KEY: MISC_FEATURE
<222> LOCATION: (16)..(16)
<223> OTHER INFORMATION: Xaa is dehydroalanine
<220> FEATURE:
<221> NAME/KEY: THIOETH
<222> LOCATION: (23)..(26)

<400> SEQUENCE: 23

```
Lys Lys Thr Lys Lys Asn Ala Ser Gly Asp Ile Ala Xaa Leu Xaa Xaa
1               5                   10                  15

Glu Ala Asp His Leu Ala Xaa Trp Val Ala Ala
            20                  25

<210> SEQ ID NO 24
<211> LENGTH: 24
<212> TYPE: PRT
<213> ORGANISM: Planomonospora sp.
<220> FEATURE:
<221> NAME/KEY: MISC_FEATURE
<222> LOCATION: (2)..(2)
<223> OTHER INFORMATION: Xaa is dehydrobutyrine
<220> FEATURE:
<221> NAME/KEY: THIOETH
<222> LOCATION: (3)..(11)
<220> FEATURE:
<221> NAME/KEY: MISC_FEATURE
<222> LOCATION: (5)..(5)
<223> OTHER INFORMATION: Xaa is dehydroalanine
<220> FEATURE:
<221> NAME/KEY: THIOETH
<222> LOCATION: (7)..(18)
<220> FEATURE:
<221> NAME/KEY: THIOETH
<222> LOCATION: (8)..(9)
<220> FEATURE:
<221> NAME/KEY: MOD_RES
<222> LOCATION: (8)..(8)
<223> OTHER INFORMATION: Xaa is Abu
<220> FEATURE:
<221> NAME/KEY: THIOETH
<222> LOCATION: (16)..(21)
<220> FEATURE:
<221> NAME/KEY: THIOETH
<222> LOCATION: (19)..(22)

<400> SEQUENCE: 24

Ile Xaa Ala Val Xaa Trp Ala Xaa Ala Thr Ala Glu Gly Gly Gly Ala
1               5                   10                  15

Gly Ala Ala His Ala Ala Pro Gly
            20

<210> SEQ ID NO 25
<211> LENGTH: 24
<212> TYPE: PRT
<213> ORGANISM: Ruminococcus gnavus
<220> FEATURE:
<221> NAME/KEY: MISC_FEATURE
<222> LOCATION: 7, 16
<223> OTHER INFORMATION: Xaa is dehydrobutyrine
<220> FEATURE:
<221> NAME/KEY: THIOETH
<222> LOCATION: (9)..(23)
<220> FEATURE:
<221> NAME/KEY: THIOETH
<222> LOCATION: (22)..(24)

<400> SEQUENCE: 25

Gly Asn Gly Val Leu Lys Xaa Ile Ser His Glu Cys Asn Met Asn Xaa
1               5                   10                  15

Trp Gln Phe Leu Phe Thr Cys Cys
            20

<210> SEQ ID NO 26
<211> LENGTH: 28
<212> TYPE: PRT
<213> ORGANISM: Bacillus halodurans
<220> FEATURE:
<221> NAME/KEY: DISULFID
<222> LOCATION: (1)..(8)
<220> FEATURE:
```

```
<221> NAME/KEY: THIOETH
<222> LOCATION: (7)..(17)
<220> FEATURE:
<221> NAME/KEY: MOD_RES
<222> LOCATION: 18, 20
<223> OTHER INFORMATION: Abu
<220> FEATURE:
<221> NAME/KEY: THIOETH
<222> LOCATION: (18)..(23)
<220> FEATURE:
<221> NAME/KEY: THIOETH
<222> LOCATION: (20)..(27)

<400> SEQUENCE: 26

Cys Ala Trp Tyr Asn Ile Ala Cys Arg Leu Gly Asn Lys Gly Ala Tyr
1               5                   10                  15

Ala Xaa Leu Xaa Val Glu Ala Met Pro Ser Ala Asn
            20                  25

<210> SEQ ID NO 27
<211> LENGTH: 24
<212> TYPE: PRT
<213> ORGANISM: Microbispora sp.
<220> FEATURE:
<221> NAME/KEY: MISC_FEATURE
<222> LOCATION: (2)..(2)
<223> OTHER INFORMATION: Xaa is dehydrobutyrine
<220> FEATURE:
<221> NAME/KEY: THIOETH
<222> LOCATION: (3)..(7)
<223> OTHER INFORMATION: Linked by Y, where Y is selected from the
      group consisting of S, S-O, S=O, O-S=O and O=S=O
<220> FEATURE:
<221> NAME/KEY: MISC_FEATURE
<222> LOCATION: (4)..(4)
<223> OTHER INFORMATION: Trp may be a modified Trp residue - the
      aromatic ring may be substituted with X where X is selected
      from the group consisting of F, Cl, Br and I
<220> FEATURE:
<221> NAME/KEY: MISC_FEATURE
<222> LOCATION: (5)..(5)
<223> OTHER INFORMATION: Xaa is dehydroalanine
<220> FEATURE:
<221> NAME/KEY: THIOETH
<222> LOCATION: (8)..(11)
<223> OTHER INFORMATION: Linked by Y, where Y is selected from the
      group consisting of S, S-O, S=O, O-S=O and O=S=O
<220> FEATURE:
<221> NAME/KEY: SITE
<222> LOCATION: 9, 14
<223> OTHER INFORMATION: Pro residue may be substituted at any of the
      ring carbon atoms with OH, alkyl or aryl
<220> FEATURE:
<221> NAME/KEY: THIOETH
<222> LOCATION: (13)..(20)
<223> OTHER INFORMATION: Linked by Y, where Y is selected from the
      group consisting of S, S-O, S=O, O-S=O and O=S=O
<220> FEATURE:
<221> NAME/KEY: THIOETH
<222> LOCATION: (18)..(23)
<223> OTHER INFORMATION: Linked by Y, where Y is selected from the
      group consisting of S, S-O, S=O, O-S=O and O=S=O
<220> FEATURE:
<221> NAME/KEY: THIOETH
<222> LOCATION: (21)..(24)
<223> OTHER INFORMATION: Linked by Y, where Y is selected from the
      group consisting of S, S-O, S=O, O-S=O and O=S=O

<400> SEQUENCE: 27

Val Xaa Ala Trp Xaa Leu Ala Thr Pro Gly Cys Thr Ala Pro Gly Gly
1               5                   10                  15

Gly Ala Gln Ala Ala Phe Ala Ala
            20
```

```
<210> SEQ ID NO 28
<211> LENGTH: 21
<212> TYPE: PRT
<213> ORGANISM: Clavibacter michiganensis
<220> FEATURE:
<221> NAME/KEY: THIOETH
<222> LOCATION: (2)..(7)
<220> FEATURE:
<221> NAME/KEY: MISC_FEATURE
<222> LOCATION: (8)..(8)
<223> OTHER INFORMATION: Xaa is Dhb
<220> FEATURE:
<221> NAME/KEY: THIOETH
<222> LOCATION: (10)..(18)
<220> FEATURE:
<221> NAME/KEY: MOD_RES
<222> LOCATION: 10, 15
<223> OTHER INFORMATION: Abu
<220> FEATURE:
<221> NAME/KEY: THIOETH
<222> LOCATION: (15)..(20)

<400> SEQUENCE: 28

Ser Ala Ser Gly Trp Leu Ala Xaa Leu Xaa Ile Glu Cys Gly Xaa Ile
1               5                   10                  15

Ile Ala Ala Ala Arg
            20

<210> SEQ ID NO 29
<211> LENGTH: 20
<212> TYPE: PRT
<213> ORGANISM: Artificial sequence
<220> FEATURE:
<223> OTHER INFORMATION: Synthetic sequence: Deoxy-actagardine B
      compound XXXII
<220> FEATURE:
<221> NAME/KEY: THIOETH
<222> LOCATION: (2)..(7)
<220> FEATURE:
<221> NAME/KEY: THIOETH
<222> LOCATION: (8)..(13)
<220> FEATURE:
<221> NAME/KEY: MOD_RES
<222> LOCATION: 8, 10, 15
<223> OTHER INFORMATION: Xaa is 4Abu
<220> FEATURE:
<221> NAME/KEY: THIOETH
<222> LOCATION: (10)..(18)
<220> FEATURE:
<221> NAME/KEY: THIOETH
<222> LOCATION: (15)..(20)

<400> SEQUENCE: 29

Ile Ala Ser Gly Trp Val Ala Xaa Leu Xaa Ile Glu Ala Gly Xaa Leu
1               5                   10                  15

Val Ala Ala Ala
            20

<210> SEQ ID NO 30
<211> LENGTH: 20
<212> TYPE: PRT
<213> ORGANISM: Artificial sequence
<220> FEATURE:
<223> OTHER INFORMATION: Synthetic sequence: Deoxy-actagardine B
      compound XXXIII
<220> FEATURE:
<221> NAME/KEY: THIOETH
<222> LOCATION: (2)..(7)
<220> FEATURE:
<221> NAME/KEY: THIOETH
<222> LOCATION: (8)..(13)
<220> FEATURE:
<221> NAME/KEY: MOD_RES
<222> LOCATION: 8, 10, 15
```

```
<223> OTHER INFORMATION: Xaa is 4Abu
<220> FEATURE:
<221> NAME/KEY: THIOETH
<222> LOCATION: (10)..(18)
<220> FEATURE:
<221> NAME/KEY: THIOETH
<222> LOCATION: (15)..(20)

<400> SEQUENCE: 30

Val Ala Ser Gly Trp Val Ala Xaa Leu Xaa Ile Glu Ala Gly Xaa Leu
1               5                   10                  15

Val Ala Ala Ala
            20

<210> SEQ ID NO 31
<211> LENGTH: 20
<212> TYPE: PRT
<213> ORGANISM: Artificial sequence
<220> FEATURE:
<223> OTHER INFORMATION: Synthetic sequence: Deoxy-actagardine B
      compound V
<220> FEATURE:
<221> NAME/KEY: THIOETH
<222> LOCATION: (2)..(7)
<220> FEATURE:
<221> NAME/KEY: THIOETH
<222> LOCATION: (8)..(13)
<220> FEATURE:
<221> NAME/KEY: MOD_RES
<222> LOCATION: 8, 10, 15
<223> OTHER INFORMATION: Xaa is 4Abu
<220> FEATURE:
<221> NAME/KEY: THIOETH
<222> LOCATION: (10)..(18)
<220> FEATURE:
<221> NAME/KEY: THIOETH
<222> LOCATION: (15)..(20)

<400> SEQUENCE: 31

Phe Ala Ser Gly Trp Val Ala Xaa Leu Xaa Ile Glu Ala Gly Xaa Leu
1               5                   10                  15

Val Ala Ala Ala
            20

<210> SEQ ID NO 32
<211> LENGTH: 20
<212> TYPE: PRT
<213> ORGANISM: Artificial sequence
<220> FEATURE:
<223> OTHER INFORMATION: Synthetic sequence: Deoxy-actagardine B
      compound XXXIV
<220> FEATURE:
<221> NAME/KEY: THIOETH
<222> LOCATION: (2)..(7)
<220> FEATURE:
<221> NAME/KEY: THIOETH
<222> LOCATION: (8)..(13)
<220> FEATURE:
<221> NAME/KEY: MOD_RES
<222> LOCATION: 8, 10, 15
<223> OTHER INFORMATION: Xaa is 4Abu
<220> FEATURE:
<221> NAME/KEY: THIOETH
<222> LOCATION: (10)..(18)
<220> FEATURE:
<221> NAME/KEY: THIOETH
<222> LOCATION: (15)..(20)

<400> SEQUENCE: 32

Lys Ala Ser Gly Trp Val Ala Xaa Leu Xaa Ile Glu Ala Gly Xaa Leu
1               5                   10                  15

Val Ala Ala Ala
```

```
<210> SEQ ID NO 33
<211> LENGTH: 20
<212> TYPE: PRT
<213> ORGANISM: Artificial sequence
<220> FEATURE:
<223> OTHER INFORMATION: Synthetic sequence: Deoxy-actagardine B
      compound XXXV
<220> FEATURE:
<221> NAME/KEY: THIOETH
<222> LOCATION: (2)..(7)
<220> FEATURE:
<221> NAME/KEY: THIOETH
<222> LOCATION: (8)..(13)
<220> FEATURE:
<221> NAME/KEY: MOD_RES
<222> LOCATION: 8, 10, 15
<223> OTHER INFORMATION: Xaa is 4Abu
<220> FEATURE:
<221> NAME/KEY: THIOETH
<222> LOCATION: (10)..(18)
<220> FEATURE:
<221> NAME/KEY: THIOETH
<222> LOCATION: (15)..(20)

<400> SEQUENCE: 33

Trp Ala Ser Gly Trp Val Ala Xaa Leu Xaa Ile Glu Ala Gly Xaa Leu
1               5                   10                  15

Val Ala Ala Ala
            20

<210> SEQ ID NO 34
<211> LENGTH: 20
<212> TYPE: PRT
<213> ORGANISM: Artificial sequence
<220> FEATURE:
<223> OTHER INFORMATION: Synthetic sequence: Actagardine compound of
      Formula Ib
<220> FEATURE:
<221> NAME/KEY: THIOETH
<222> LOCATION: (2)..(7)
<220> FEATURE:
<221> NAME/KEY: THIOETH
<222> LOCATION: (8)..(13)
<220> FEATURE:
<221> NAME/KEY: MOD_RES
<222> LOCATION: 8, 10, 15
<223> OTHER INFORMATION: Xaa is 4Abu
<220> FEATURE:
<221> NAME/KEY: THIOETH
<222> LOCATION: (10)..(18)
<220> FEATURE:
<221> NAME/KEY: THIOETH
<222> LOCATION: (15)..(20)
<223> OTHER INFORMATION: Linked by -S(O)-
<220> FEATURE:
<221> NAME/KEY: Variant
<222> LOCATION: 16
<223> OTHER INFORMATION: Xaa is -C1-4 alkyl
<220> FEATURE:
<221> NAME/KEY: Variant
<222> LOCATION: 17
<223> OTHER INFORMATION: Xaa is -C1-4 alkyl

<400> SEQUENCE: 34

Ala Ala Ser Gly Trp Val Ala Xaa Leu Xaa Ile Glu Ala Gly Xaa Xaa
1               5                   10                  15

Xaa Ala Ala Ala
            20
```